United States Patent
Henderson et al.

(10) Patent No.: US 11,678,925 B2
(45) Date of Patent: Jun. 20, 2023

(54) METHOD FOR CONTROLLING AN ENERGY MODULE OUTPUT

(71) Applicant: Cilag GmbH International, Zug (CH)

(72) Inventors: Joshua Henderson, Cincinnati, OH (US); Joshua P. Morgan, Loveland, OH (US); Eitan T. Wiener, Cincinnati, OH (US); John E. Hein, Neenah, WI (US); James R. Hoch, Appleton, WI (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 497 days.

(21) Appl. No.: 16/562,135

(22) Filed: Sep. 5, 2019

(65) Prior Publication Data

US 2020/0078076 A1     Mar. 12, 2020

Related U.S. Application Data

(60) Provisional application No. 62/728,480, filed on Sep. 7, 2018, provisional application No. 62/826,587, filed
(Continued)

(51) Int. Cl.
*A61B 18/12*     (2006.01)
*A61B 18/00*     (2006.01)
(Continued)

(52) U.S. Cl.
CPC ............ *A61B 18/00* (2013.01); *A61B 17/072* (2013.01); *A61B 17/320068* (2013.01);
(Continued)

(58) Field of Classification Search
CPC ............ A61B 2018/1273; A61B 90/90; A61B 18/1233; A61B 2018/00994;
(Continued)

(56) References Cited

U.S. PATENT DOCUMENTS 4,171,700 A   10/1979  Farin
4,849,752 A    7/1989  Bryant
(Continued)

FOREIGN PATENT DOCUMENTS

EP    0408160 A1    1/1991
EP    0473987 A1    3/1992
(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.
(Continued)

*Primary Examiner* — Joanne M Rodden
*Assistant Examiner* — Sean W Collins

(57) ABSTRACT

A method for controlling an output of an energy module of a modular energy system. The energy module can comprise a plurality of amplifiers configured to generate a drive signal at a frequency range and a plurality of ports coupled to the plurality of amplifiers. The method includes determining to which port of the plurality of ports the surgical instrument is connected, selectively coupling an amplifier of the plurality of amplifiers to the port of the plurality of ports to which the surgical instrument is connected, and controlling the amplifier to deliver the drive signal for driving the energy modality to the surgical instrument through the port.

15 Claims, 63 Drawing Sheets

Related U.S. Application Data on Mar. 29, 2019, provisional application No. 62/826,592, filed on Mar. 29, 2019, provisional application No. 62/826,584, filed on Mar. 29, 2019, provisional application No. 62/826,588, filed on Mar. 29, 2019.

(51) Int. Cl.

| | | |
|---|---|---|
| *A61B 34/35* | (2016.01) | |
| *A61B 34/20* | (2016.01) | |
| *A61B 90/00* | (2016.01) | |
| *A61B 34/00* | (2016.01) | |
| *A61B 17/32* | (2006.01) | |
| *G16H 20/40* | (2018.01) | |
| *A61B 18/14* | (2006.01) | |
| *H04L 49/25* | (2022.01) | |
| *H04L 9/40* | (2022.01) | |
| *H04L 67/10* | (2022.01) | |
| *H04L 67/12* | (2022.01) | |
| *A61B 18/16* | (2006.01) | |
| *H04B 5/00* | (2006.01) | |
| *H01R 43/26* | (2006.01) | |
| *A61B 90/90* | (2016.01) | |
| *H05K 5/00* | (2006.01) | |
| *H04M 1/72406* | (2021.01) | |
| *G06F 8/65* | (2018.01) | |
| *A61B 17/072* | (2006.01) | |
| *A61B 17/00* | (2006.01) | |
| *A61B 90/30* | (2016.01) | |
| *A61B 34/30* | (2016.01) | |
| *H04L 27/04* | (2006.01) | |
| *A61B 34/37* | (2016.01) | |
| *H05K 7/02* | (2006.01) | |

(52) U.S. Cl.
CPC .. *A61B 17/320092* (2013.01); *A61B 18/1206* (2013.01); *A61B 18/1233* (2013.01); *A61B 18/1445* (2013.01); *A61B 18/16* (2013.01); *A61B 34/20* (2016.02); *A61B 34/25* (2016.02); *A61B 34/35* (2016.02); *A61B 34/74* (2016.02); *A61B 90/361* (2016.02); *A61B 90/90* (2016.02); *G06F 8/65* (2013.01); *G16H 20/40* (2018.01); *H01R 43/26* (2013.01); *H04B 5/0031* (2013.01); *H04L 49/25* (2013.01); *H04L 63/0245* (2013.01); *H04L 67/10* (2013.01); *H04L 67/12* (2013.01); *H04M 1/72406* (2021.01); *H05K 5/0021* (2013.01); *A61B 34/37* (2016.02); *A61B 90/30* (2016.02); *A61B 90/37* (2016.02); *A61B 2017/00026* (2013.01); *A61B 2017/00199* (2013.01); *A61B 2017/00221* (2013.01); *A61B 2017/00225* (2013.01); *A61B 2017/00398* (2013.01); *A61B 2017/00477* (2013.01); *A61B 2017/00526* (2013.01); *A61B 2017/00973* (2013.01); *A61B 2017/07257* (2013.01); *A61B 2017/07271* (2013.01); *A61B 2017/07285* (2013.01); *A61B 2017/320074* (2017.08); *A61B 2018/0063* (2013.01); *A61B 2018/0072* (2013.01); *A61B 2018/0094* (2013.01); *A61B 2018/00178* (2013.01); *A61B 2018/00208* (2013.01); *A61B 2018/00601* (2013.01); *A61B 2018/00642* (2013.01); *A61B 2018/00702* (2013.01); *A61B 2018/00708* (2013.01); *A61B 2018/00732* (2013.01); *A61B 2018/00767* (2013.01); *A61B 2018/00845* (2013.01); *A61B 2018/00875* (2013.01); *A61B 2018/00916* (2013.01); *A61B 2018/00958* (2013.01); *A61B 2018/00994* (2013.01); *A61B 2018/126* (2013.01); *A61B 2018/128* (2013.01); *A61B 2018/1253* (2013.01); *A61B 2018/1273* (2013.01); *A61B 2018/1286* (2013.01); *A61B 2018/165* (2013.01); *A61B 2034/2048* (2016.02); *A61B 2034/2055* (2016.02); *A61B 2034/305* (2016.02); *A61B 2090/371* (2016.02); *A61B 2090/378* (2016.02); *A61B 2218/002* (2013.01); *A61B 2218/007* (2013.01); *A61B 2218/008* (2013.01); *A61B 2560/0443* (2013.01); *A61B 2560/0456* (2013.01); *H01R 2201/12* (2013.01); *H04L 27/04* (2013.01); *H05K 5/0026* (2013.01); *H05K 5/0065* (2013.01); *H05K 7/023* (2013.01)

(58) Field of Classification Search
CPC .. A61B 2018/00916; A61B 2018/0094; A61B 2018/1253
See application file for complete search history.

(56) References Cited

U.S. PATENT DOCUMENTS

| | | |
|---|---|---|
| D303,787 S | 10/1989 | Messenger et al. |
| D327,061 S | 6/1992 | Soren et al. |
| 5,189,277 A | 2/1993 | Boisvert et al. |
| 5,204,669 A | 4/1993 | Dorfe et al. |
| 5,318,563 A | 6/1994 | Malis et al. |
| 5,325,270 A | 6/1994 | Wenger et al. |
| 5,425,375 A | 6/1995 | Chin et al. |
| D379,346 S | 5/1997 | Mieki |
| 5,690,504 A | 11/1997 | Scanlan et al. |
| 5,693,042 A | 12/1997 | Boiarski et al. |
| 5,724,468 A | 3/1998 | Leone et al. |
| 6,049,467 A | 4/2000 | Tamarkin et al. |
| 6,055,458 A | 4/2000 | Cochran et al. |
| D431,811 S | 10/2000 | Nishio et al. |
| 6,179,136 B1 | 1/2001 | Kluge et al. |
| 6,269,411 B1 | 7/2001 | Reasoner |
| 6,288,606 B1 | 9/2001 | Ekman et al. |
| 6,416,471 B1 | 7/2002 | Kumar et al. |
| 6,546,270 B1 | 4/2003 | Goldin et al. |
| 6,584,358 B2 | 6/2003 | Carter et al. |
| 6,611,793 B1 | 8/2003 | Burnside et al. |
| 6,731,514 B2 | 5/2004 | Evans |
| 6,760,218 B2 | 7/2004 | Fan |
| 6,839,238 B2 | 1/2005 | Derr et al. |
| 6,843,657 B2 | 1/2005 | Driscoll et al. |
| 6,913,471 B2 | 7/2005 | Smith |
| 7,009,511 B2 | 3/2006 | Mazar et al. |
| 7,044,949 B2 | 5/2006 | Orszulak et al. |
| 7,074,205 B1 | 7/2006 | Duffy et al. |
| 7,134,994 B2 | 11/2006 | Alpert et al. |
| 7,171,784 B2 | 2/2007 | Eenigenburg |
| 7,217,269 B2 | 5/2007 | El-Galley et al. |
| 7,252,664 B2 | 8/2007 | Nasab et al. |
| 7,344,532 B2 | 3/2008 | Goble et al. |
| 7,353,068 B2 | 4/2008 | Tanaka et al. |
| 7,408,439 B2 | 8/2008 | Wang et al. |
| D579,876 S | 11/2008 | Novotney et al. |
| D583,328 S | 12/2008 | Chiang |
| 7,496,418 B2 | 2/2009 | Kim et al. |
| D589,447 S | 3/2009 | Sasada et al. |
| 7,500,747 B2 | 3/2009 | Howell et al. |
| 7,518,502 B2 | 4/2009 | Austin et al. |
| 7,563,259 B2 | 7/2009 | Takahashi |
| 7,601,149 B2 | 10/2009 | DiCarlo et al. |
| 7,637,907 B2 | 12/2009 | Blaha |
| 7,656,671 B2 | 2/2010 | Liu et al. |
| 7,757,028 B2 | 7/2010 | Druke et al. |
| D631,252 S | 1/2011 | Leslie |
| 7,932,826 B2 | 4/2011 | Fritchie et al. |
| 7,945,065 B2 | 5/2011 | Menzl et al. |
| 7,945,342 B2 | 5/2011 | Tsai et al. |
| 7,982,776 B2 | 7/2011 | Dunki-Jacobs et al. |

(56) References Cited

U.S. PATENT DOCUMENTS

| | | |
|---|---|---|
| 7,995,045 B2 | 8/2011 | Dunki-Jacobs |
| 8,019,094 B2 | 9/2011 | Hsieh et al. |
| D655,678 S | 3/2012 | Kobayashi et al. |
| D657,368 S | 4/2012 | Magee et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,504,136 B1 | 8/2013 | Sun et al. |
| 8,540,709 B2 | 9/2013 | Allen |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| D716,333 S | 10/2014 | Chotin et al. |
| 8,917,513 B1 | 12/2014 | Hazzard |
| 8,920,186 B2 | 12/2014 | Shishikura |
| 8,923,012 B2 | 12/2014 | Kaufman et al. |
| 8,968,296 B2 | 3/2015 | McPherson |
| 8,986,288 B2 | 3/2015 | Konishi |
| D729,267 S | 5/2015 | Yoo et al. |
| 9,055,870 B2 | 6/2015 | Meador et al. |
| 9,065,394 B2 | 6/2015 | Lim et al. |
| 9,129,054 B2 | 9/2015 | Nawana et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,320,646 B2 | 4/2016 | Todd et al. |
| 9,345,481 B2 | 5/2016 | Hall et al. |
| 9,345,900 B2 | 5/2016 | Wu et al. |
| 9,351,653 B1 | 5/2016 | Harrison |
| 9,427,255 B2 | 8/2016 | Griffith et al. |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,532,827 B2 | 1/2017 | Morgan et al. |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| 9,867,670 B2 | 1/2018 | Brannan et al. |
| 9,907,196 B2 | 2/2018 | Susini et al. |
| 9,971,395 B2 | 4/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 11,000,270 B2 | 5/2021 | Scheib et al. |
| D924,139 S | 7/2021 | Jayme |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,083,489 B2 | 8/2021 | Fujii et al. |
| 11,116,587 B2 | 9/2021 | Wolf et al. |
| D939,545 S | 12/2021 | Oberkircher et al. |
| 11,218,822 B2 | 1/2022 | Morgan et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,298,128 B2 | 4/2022 | Messerly et al. |
| 11,304,763 B2 | 4/2022 | Shelton, IV et al. |
| 11,314,846 B1 | 4/2022 | Colin et al. |
| 11,350,978 B2 | 6/2022 | Henderson et al. |
| 11,369,366 B2 | 6/2022 | Scheib et al. |
| 11,419,604 B2 | 8/2022 | Scheib et al. |
| 11,424,027 B2 | 8/2022 | Shelton, IV |
| 11,504,192 B2 | 11/2022 | Shelton, IV et al. |
| 2001/0029315 A1* | 10/2001 | Sakurai .......... A61B 17/320068 600/101 |
| 2003/0078631 A1 | 4/2003 | Nelson et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0256516 A1 | 11/2006 | Cho |
| 2007/0076363 A1 | 4/2007 | Liang et al. |
| 2007/0282321 A1 | 12/2007 | Shah et al. |

(56) References Cited

U.S. PATENT DOCUMENTS

| | | |
|---|---|---|
| 2008/0072896 A1 | 3/2008 | Setzer et al. |
| 2008/0129465 A1 | 6/2008 | Rao |
| 2008/0249377 A1 | 10/2008 | Molducci et al. |
| 2009/0036884 A1 | 2/2009 | Gregg et al. |
| 2009/0131929 A1* | 5/2009 | Shimizu ............ A61B 18/1445 606/34 |
| 2009/0216091 A1 | 8/2009 | Arndt |
| 2009/0234352 A1 | 9/2009 | Behnke et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Selig |
| 2011/0125149 A1 | 5/2011 | El-Galley et al. |
| 2011/0130689 A1 | 6/2011 | Cohen et al. |
| 2011/0245630 A1 | 10/2011 | St. Pierre et al. |
| 2011/0273465 A1 | 11/2011 | Konishi et al. |
| 2011/0288451 A1* | 11/2011 | Sanai ................ A61B 18/1445 601/2 |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2013/0031201 A1 | 1/2013 | Kagan et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0155721 A1 | 6/2014 | Hauck et al. |
| 2014/0194683 A1 | 7/2014 | Nakaguchi |
| 2014/0226572 A1 | 8/2014 | Thota et al. |
| 2014/0262598 A1 | 9/2014 | Miki et al. |
| 2014/0263552 A1 | 9/2014 | Hall et al. |
| 2015/0190189 A1 | 7/2015 | Yates et al. |
| 2015/0289929 A1 | 10/2015 | Toth et al. |
| 2016/0045247 A1 | 2/2016 | Heim et al. |
| 2016/0058286 A1 | 3/2016 | Joshua et al. |
| 2016/0074096 A1 | 3/2016 | Lieu |
| 2016/0120591 A1 | 5/2016 | Smith et al. |
| 2016/0287312 A1 | 10/2016 | Tegg et al. |
| 2017/0000553 A1 | 1/2017 | Wiener et al. |
| 2017/0090507 A1 | 3/2017 | Wiener et al. |
| 2017/0189096 A1 | 7/2017 | Danziger et al. |
| 2017/0202595 A1 | 7/2017 | Shelton, IV |
| 2017/0251305 A1 | 8/2017 | Fathollahi |
| 2017/0252091 A1* | 9/2017 | Honda ............... A61B 18/1445 |
| 2017/0296213 A1 | 10/2017 | Swensgard et al. |
| 2017/0319259 A1* | 11/2017 | Dunning ............ A61B 18/1482 |
| 2018/0042659 A1 | 2/2018 | Rupp et al. |
| 2018/0065248 A1 | 3/2018 | Barral et al. |
| 2018/0082480 A1 | 3/2018 | White et al. |
| 2018/0099161 A1 | 4/2018 | Honda |
| 2018/0221005 A1 | 8/2018 | Hamel et al. |
| 2018/0228528 A1* | 8/2018 | Fraasch ............. A61B 18/1206 |
| 2018/0262916 A1 | 9/2018 | Polley et al. |
| 2018/0263557 A1 | 9/2018 | Kahlman |
| 2018/0333207 A1 | 11/2018 | Moctezuma De la Barrera |
| 2019/0069957 A1 | 3/2019 | Barral et al. |
| 2019/0200906 A1 | 7/2019 | Shelton, IV et al. |
| 2019/0200981 A1 | 7/2019 | Harris et al. |
| 2019/0201046 A1 | 7/2019 | Shelton, IV et al. |
| 2019/0201102 A1 | 7/2019 | Shelton, IV et al. |
| 2019/0201137 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0206562 A1 | 7/2019 | Shelton, IV et al. |
| 2019/0224434 A1 | 7/2019 | Silver et al. |
| 2019/0247141 A1 | 8/2019 | Batchelor et al. |
| 2019/0278262 A1 | 9/2019 | Taylor et al. |
| 2019/0279524 A1 | 9/2019 | Stoyanov et al. |
| 2020/0004487 A1 | 1/2020 | Hanajima et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015902 A1 | 1/2020 | Scheib et al. |
| 2020/0015907 A1 | 1/2020 | Scheib |
| 2020/0015924 A1 | 1/2020 | Scheib et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078083 A1 | 3/2020 | Sprinkle et al. |
| 2020/0078089 A1 | 3/2020 | Henderson et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0268472 A1 | 8/2020 | Wolf et al. |
| 2020/0305924 A1 | 10/2020 | Carroll |
| 2020/0305945 A1 | 10/2020 | Morgan et al. |
| 2021/0196383 A1 | 7/2021 | Shelton, IV et al. |
| 2021/0203889 A1 | 7/2021 | Fung et al. |
| 2021/0212717 A1 | 7/2021 | Yates et al. |
| 2021/0236755 A1 | 8/2021 | King et al. |
| 2021/0385889 A1 | 12/2021 | Patel |
| 2022/0032442 A1 | 2/2022 | Sheffield et al. |
| 2022/0151704 A1 | 5/2022 | Nikou |
| 2022/0261056 A1 | 8/2022 | Motoi et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0338049 A1 | 10/2022 | Ross et al. |

FOREIGN PATENT DOCUMENTS

| | | |
|---|---|---|
| EP | 0929263 B1 | 7/1999 |
| EP | 1006892 B1 | 6/2009 |
| EP | 2942023 A2 | 11/2015 |
| JP | 2001029353 A | 2/2001 |
| WO | WO-0112089 A1 | 2/2001 |
| WO | WO-2008053485 A1 | 5/2008 |
| WO | WO-2014031800 A1 | 2/2014 |
| WO | WO-2014071184 A1 | 5/2014 |
| WO | WO-2015047693 A1 | 4/2015 |
| WO | WO-2017058617 | 4/2017 |
| WO | WO-2018116247 A1 | 6/2018 |

(56) References Cited

FOREIGN PATENT DOCUMENTS

WO    WO-2019215354 A1    11/2019
WO    WO-2021044136 A1    3/2021

OTHER PUBLICATIONS

IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Zhu et al. "Haptic-feedback smart glove as a creative human-machine interface (HMI) for virtual/augmented reality applications," Sci. Adv, vol. 6, No. 19, May 8, 2020.
Qian, et al., "A Review of Augmented Reality in Robotic-Assisted Surgery", IEEE Transactions on Medical Robotics and Bionics, IEEE, vol. 2, No. 1, pp. 1-16, Feb. 2020.

\* cited by examiner

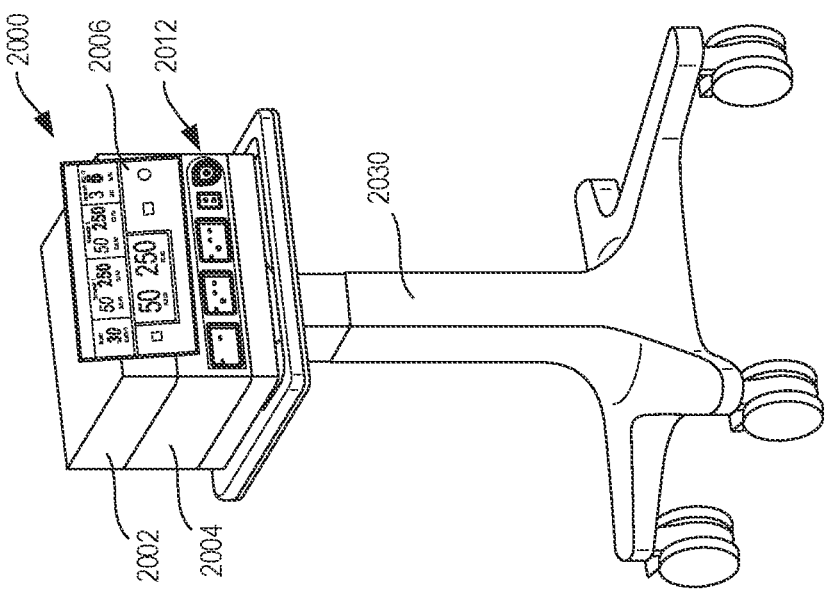
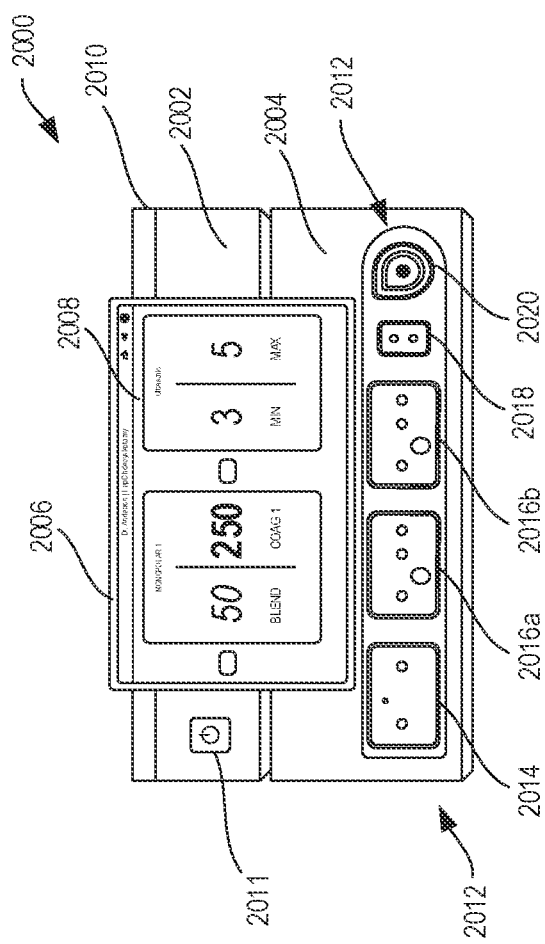
FIG. 25B
FIG. 25A

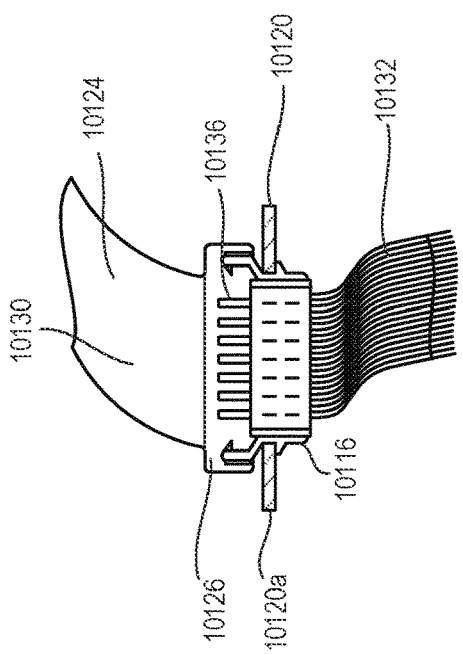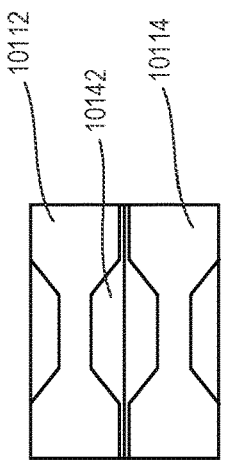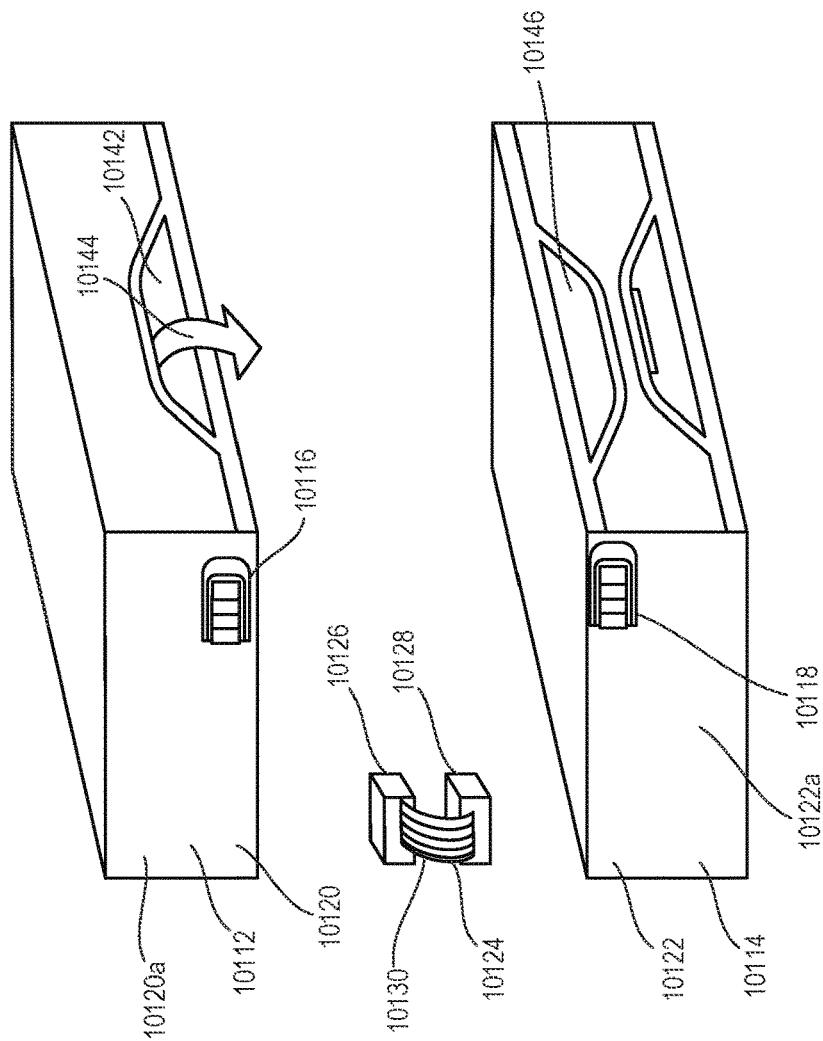

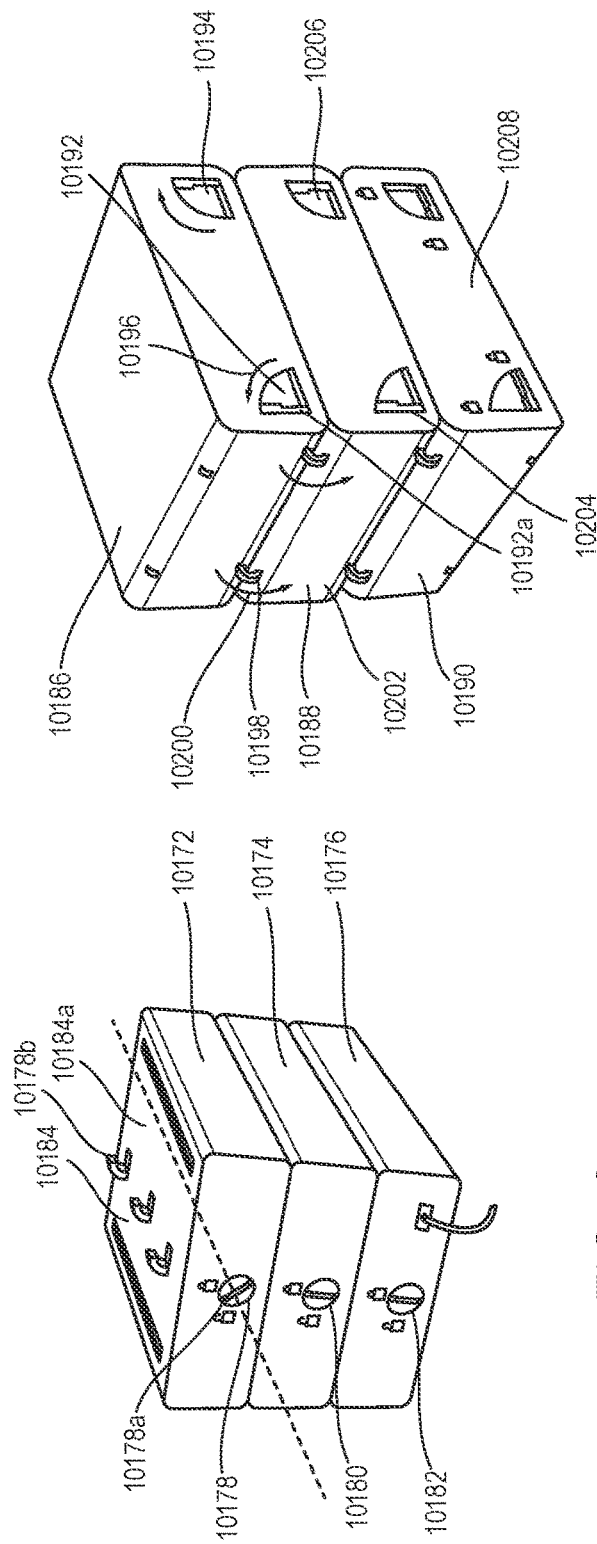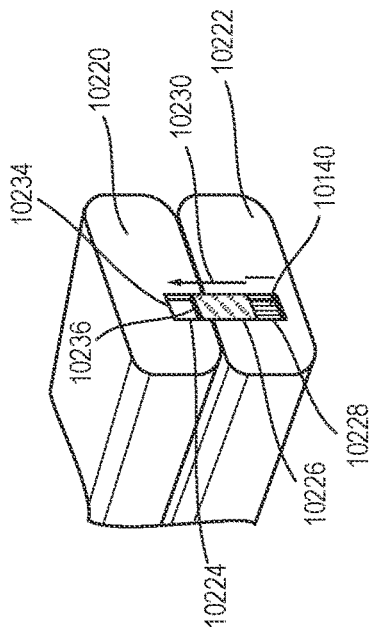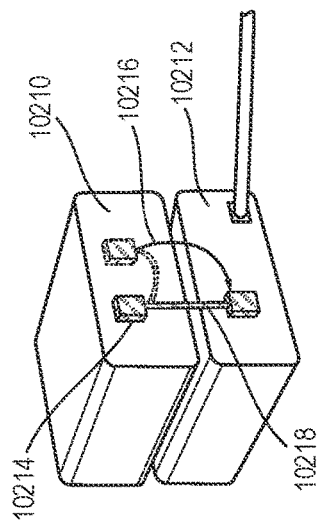

METHOD FOR CONTROLLING AN ENERGY MODULE OUTPUT

CROSS-REFERENCE TO RELATED APPLICATIONS

The present application claims priority under 35 U.S.C. § 119(e) to U.S. Provisional Patent Application Ser. No. 62/826,584, titled MODULAR SURGICAL PLATFORM ELECTRICAL ARCHITECTURE, filed Mar. 29, 2019, the disclosure of which is herein incorporated by reference in its entirety.

The present application claims priority under 35 U.S.C. § 119(e) to U.S. Provisional Patent Application Ser. No. 62/826,587, titled MODULAR ENERGY SYSTEM CONNECTIVITY, filed Mar. 29, 2019, the disclosure of which is herein incorporated by reference in its entirety.

The present application claims priority under 35 U.S.C. § 119(e) to U.S. Provisional Patent Application Ser. No. 62/826,588, titled MODULAR ENERGY SYSTEM INSTRUMENT COMMUNICATION TECHNIQUES, filed Mar. 29, 2019, the disclosure of which is herein incorporated by reference in its entirety.

The present application claims priority under 35 U.S.C. § 119(e) to U.S. Provisional Patent Application Ser. No. 62/826,592, titled MODULAR ENERGY DELIVERY SYSTEM, filed Mar. 29, 2019, the disclosure of which is herein incorporated by reference in its entirety.

The present application claims priority under 35 U.S.C. § 119(e) to U.S. Provisional Patent Application Ser. No. 62/728,480, titled MODULAR ENERGY SYSTEM AND USER INTERFACE, filed Sep. 7, 2018, the disclosure of which is herein incorporated by reference in its entirety.

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

SUMMARY

In one general aspect, a method for controlling an output of an energy module of a modular energy system. The energy module can comprise a plurality of amplifiers and a plurality of ports coupled to the plurality of amplifiers. Each of the plurality of amplifiers can be configured to generate a drive signal at a frequency range. Each of the plurality of ports can be configured to drive an energy modality for a surgical instrument connected thereto according to each drive signal. The method can comprise: determining to which port of the plurality of ports the surgical instrument is connected; selectively coupling an amplifier of the plurality of amplifiers to the port of the plurality of ports to which the surgical instrument is connected; and controlling the amplifier to deliver the drive signal for driving the energy modality to the surgical instrument through the port.

In another general aspect, a method for controlling an output of an energy module of a modular energy system. The energy module can comprise a plurality of amplifiers, a plurality of ports coupled to the plurality of amplifiers, and a relay assembly, each of the plurality of amplifiers configured to generate a drive signal at a frequency range, each of the plurality of ports configured to drive an energy modality for a surgical instrument connected thereto according to each drive signal, the method comprising: controlling a first amplifier of the plurality of amplifiers to deliver a first drive signal to the surgical instrument connected to a port; controlling the relay assembly to couple a second amplifier of the plurality of amplifiers to the port; and controlling the second amplifier to deliver a second drive signal to the surgical instrument connected to the port.

FIGURES

The various aspects described herein, both as to organization and methods of operation, together with further objects and advantages thereof, may best be understood by reference to the following description, taken in conjunction with the accompanying drawings as follows.

FIG. 25A is a first illustrative modular energy system configuration including a header module and a display screen that renders a graphical user interface (GUI) for relaying information regarding modules connected to the header module, in accordance with at least one aspect of the present disclosure.

FIG. 25B is the modular energy system shown in FIG. 25A mounted to a cart, in accordance with at least one aspect of the present disclosure.

FIG. 60 illustrates a modular energy system, in accordance with at least one aspect of the present disclosure.

FIG. 61 illustrates a side view of the modular energy system of FIG. 60.

FIG. 65 illustrates a modular energy system comprising a latch assembly, in accordance with at least one aspect of the present disclosure.

FIG. 66 illustrates a modular energy system comprising a latch assembly, in accordance with at least one aspect of the present disclosure.

FIG. 67 illustrates a modular energy system comprising a cord assembly, in accordance with at least one aspect of the present disclosure.

FIG. 68 illustrates a modular energy system comprising a plug, in accordance with at least one aspect of the present disclosure.

FIG. 69 illustrates various electrical connections in the modular energy system of FIG. 60.

DESCRIPTION

Figure 1:
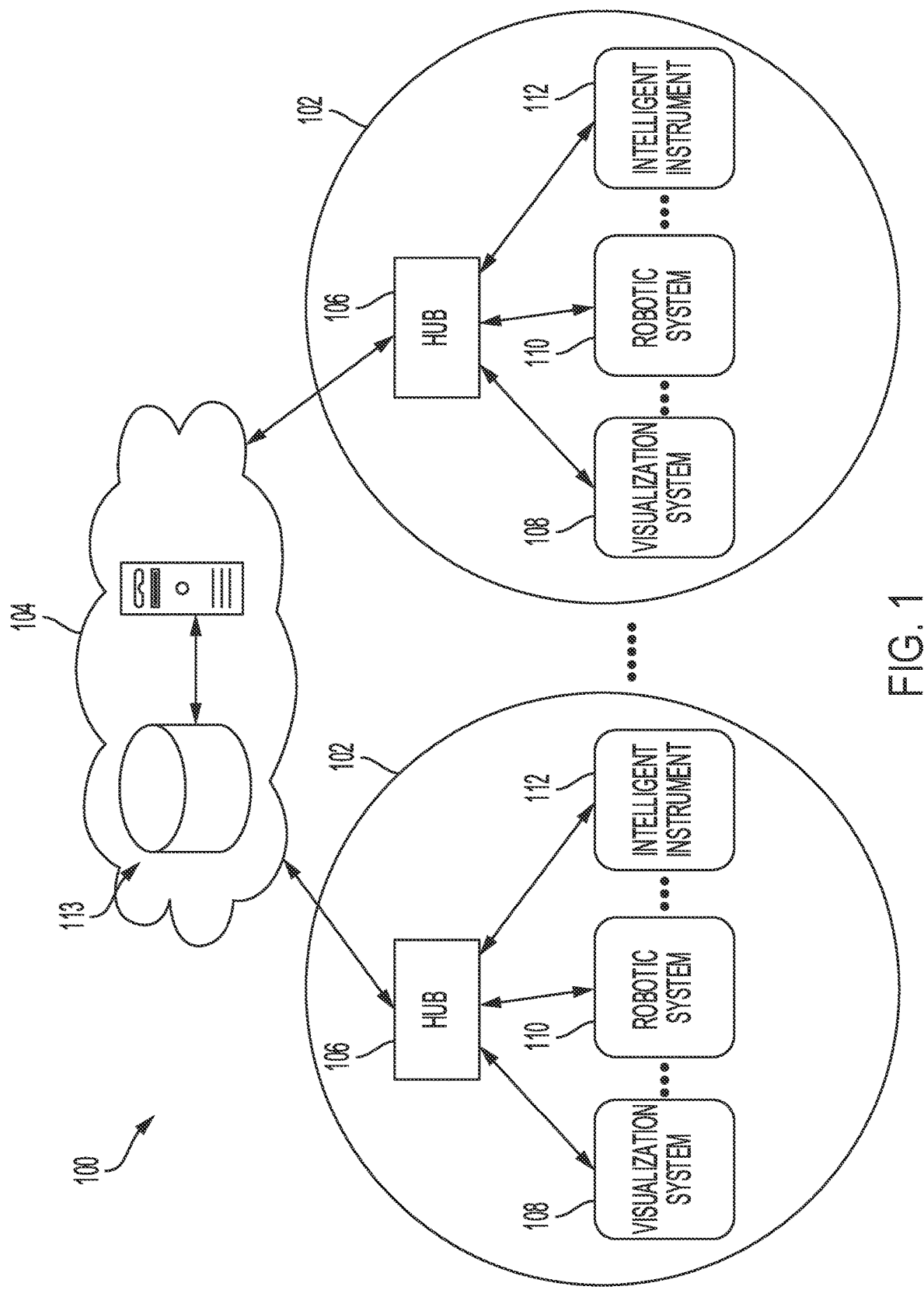
FIG. 1 is a block diagram of a computer-implemented interactive surgical system, in accordance with at least one aspect of the present disclosure.

Applicant of the present application owns the following U.S. patent applications filed concurrently herewith, the disclosure of each of which is herein incorporated by reference in its entirety:

- U.S. patent application Ser. No. 16/562,123, titled METHOD FOR CONSTRUCTING AND USING A MODULAR SURGICAL ENERGY SYSTEM WITH MULTIPLE DEVICES;
- U.S. patent application Ser. No. 16/562,142, titled METHOD FOR ENERGY DISTRIBUTION IN A SURGICAL MODULAR ENERGY SYSTEM;
- U.S. patent application Ser. No. 16/562,169, titled SURGICAL MODULAR ENERGY SYSTEM WITH A SEGMENTED BACKPLANE;
- U.S. patent application Ser. No. 16/562,185, titled SURGICAL MODULAR ENERGY SYSTEM WITH FOOTER MODULE;
- U.S. patent application Ser. No. 16/562,203, titled POWER AND COMMUNICATION MITIGATION ARRANGEMENT FOR MODULAR SURGICAL ENERGY SYSTEM;
- U.S. patent application Ser. No. 16/562,212, titled MODULAR SURGICAL ENERGY SYSTEM WITH MODULE POSITIONAL AWARENESS SENSING WITH VOLTAGE DETECTION;
- U.S. patent application Ser. No. 16/562,234, titled MODULAR SURGICAL ENERGY SYSTEM WITH MODULE POSITIONAL AWARENESS SENSING WITH TIME COUNTER;
- U.S. patent application Ser. No. 16/562,243, titled MODULAR SURGICAL ENERGY SYSTEM WITH MODULE POSITIONAL AWARENESS WITH DIGITAL LOGIC;
- U.S. patent application Ser. No. 16/562,135, titled METHOD FOR CONTROLLING AN ENERGY MODULE OUTPUT;
- U.S. patent application Ser. No. 16/562,180, titled ENERGY MODULE FOR DRIVING MULTIPLE ENERGY MODALITIES;
- U.S. patent application Ser. No. 16/562,184, titled GROUNDING ARRANGEMENT OF ENERGY MODULES;
- U.S. patent application Ser. No. 16/562,188, titled BACKPLANE CONNECTOR DESIGN TO CONNECT STACKED ENERGY MODULES;
- U.S. patent application Ser. No. 16/562,195, titled ENERGY MODULE FOR DRIVING MULTIPLE ENERGY MODALITIES THROUGH A PORT;
- U.S. patent application Ser. No. 16/562,202 titled SURGICAL INSTRUMENT UTILIZING DRIVE SIGNAL TO POWER SECONDARY FUNCTION;

U.S. patent application Ser. No. 16/562,144, titled METHOD FOR CONTROLLING A MODULAR ENERGY SYSTEM USER INTERFACE;

U.S. patent application Ser. No. 16/562,151, titled PASSIVE HEADER MODULE FOR A MODULAR ENERGY SYSTEM;

U.S. patent application Ser. No. 16/562,157, titled CONSOLIDATED USER INTERFACE FOR MODULAR ENERGY SYSTEM;

U.S. patent application Ser. No. 16/562,159, titled AUDIO TONE CONSTRUCTION FOR AN ENERGY MODULE OF A MODULAR ENERGY SYSTEM;

U.S. patent application Ser. No. 16/562,163, titled ADAPTABLY CONNECTABLE AND REASSIGNABLE SYSTEM ACCESSORIES FOR MODULAR ENERGY SYSTEM;

U.S. patent application Ser. No. 16/562,125, titled METHOD FOR COMMUNICATING BETWEEN MODULES AND DEVICES IN A MODULAR SURGICAL SYSTEM;

U.S. patent application Ser. No. 16/562,137, titled FLEXIBLE HAND-SWITCH CIRCUIT;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT;

U.S. patent application Ser. No. 16/562,148, titled FLEXIBLE NEUTRAL ELECTRODE;

U.S. patent application Ser. No. 16/562,154, titled SMART RETURN PAD SENSING THROUGH MODULATION OF NEAR FIELD COMMUNICATION AND CONTACT QUALITY MONITORING SIGNALS;

U.S. patent application Ser. No. 16/562,162, titled AUTOMATIC ultrasonic ENERGY ACTIVATION CIRCUIT DESIGN FOR MODULAR SURGICAL SYSTEMS;

U.S. patent application Ser. No. 16/562,167, titled COORDINATED ENERGY OUTPUTS OF SEPARATE BUT CONNECTED MODULES;

U.S. patent application Ser. No. 16/562,170, titled MANAGING SIMULTANEOUS MONOPOLAR OUTPUTS USING DUTY CYCLE AND SYNCHRONIZATION;

U.S. patent application Ser. No. 16/562,172, titled PORT PRESENCE DETECTION SYSTEM FOR MODULAR ENERGY SYSTEM;

U.S. patent application Ser. No. 16/562,175, titled INSTRUMENT TRACKING ARRANGEMENT BASED ON REAL TIME CLOCK INFORMATION;

U.S. patent application Ser. No. 16/562,177, titled REGIONAL LOCATION TRACKING OF COMPONENTS OF A MODULAR ENERGY SYSTEM;

U.S. Design patent application Ser. No. 29/704,610, titled ENERGY MODULE;

U.S. Design patent application Ser. No. 29/704,614, titled ENERGY MODULE MONOPOLAR PORT WITH FOURTH SOCKET AMONG THREE OTHER SOCKETS;

U.S. Design patent application Ser. No. 29/704,616, titled BACKPLANE CONNECTOR FOR ENERGY MODULE; and U.S. Design patent application Ser. No. 29/704,617, titled ALERT SCREEN FOR ENERGY MODULE.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
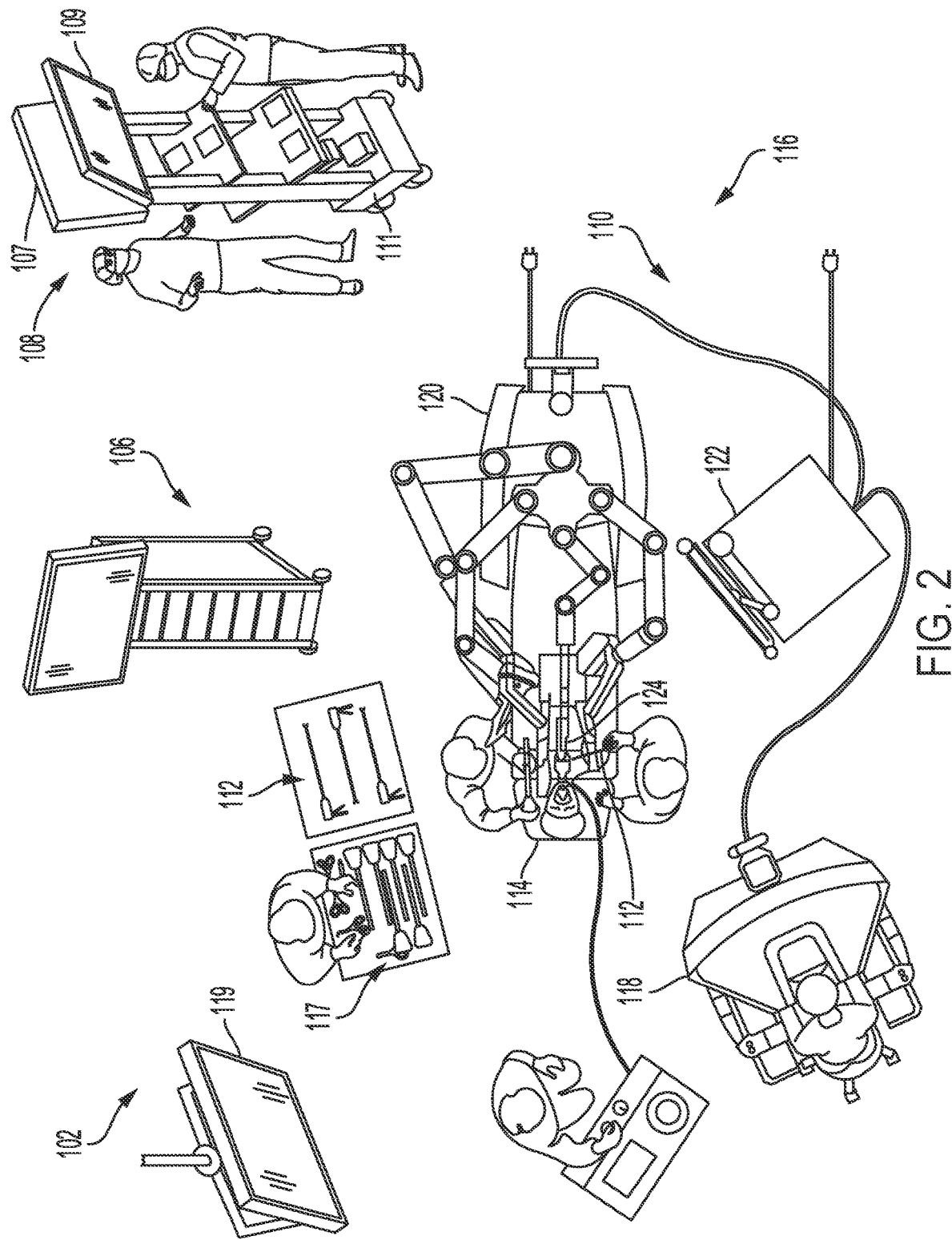
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area. In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
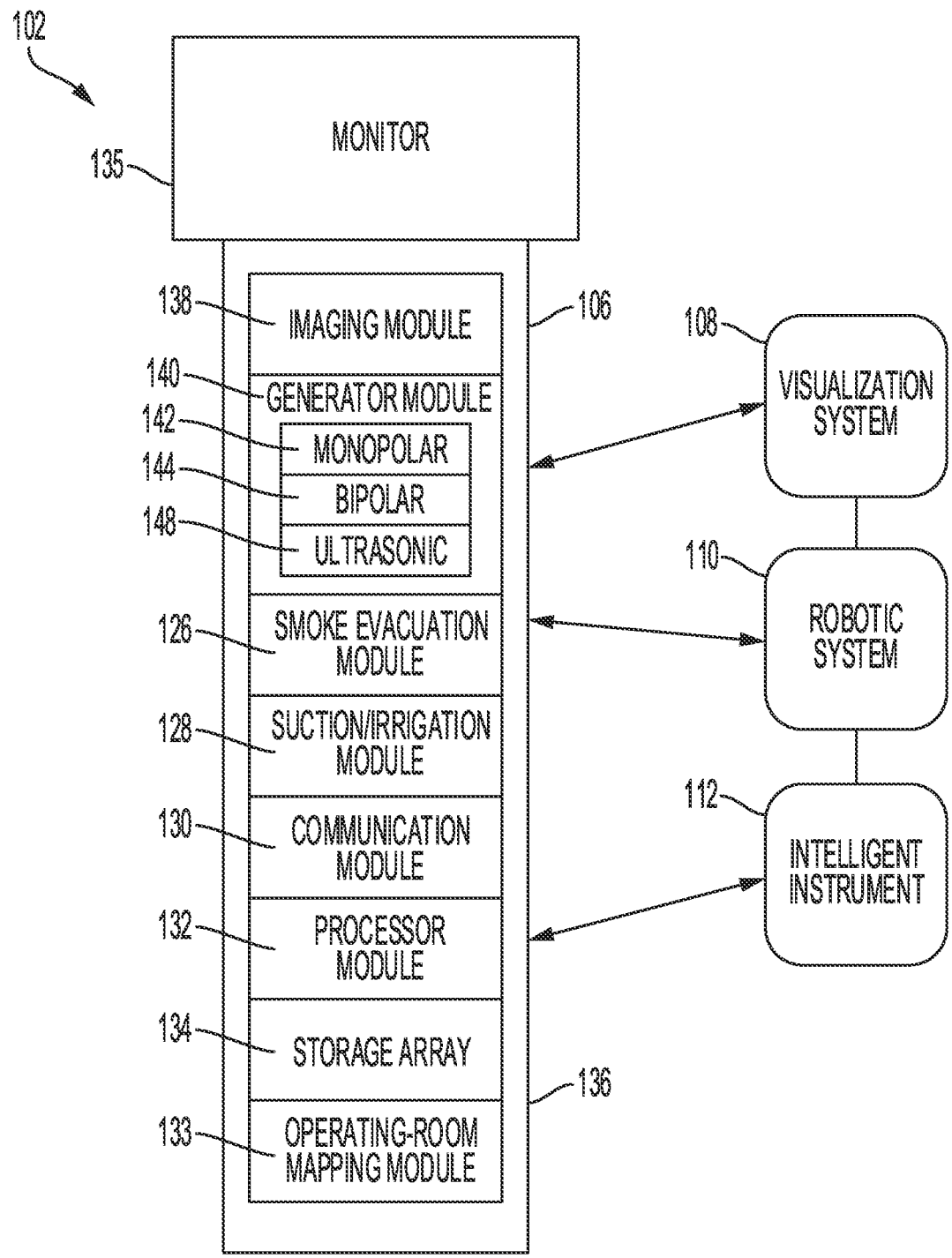
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 4:
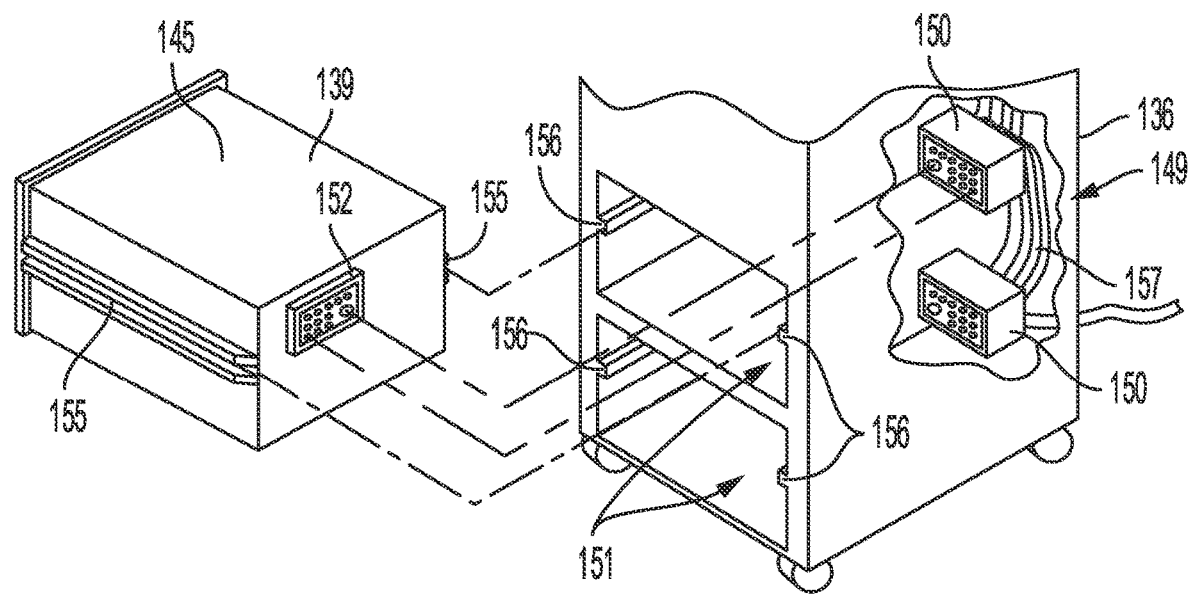
FIG. 4 is a partial perspective view of a surgical hub enclosure, and of a combo generator module slidably receivable in a drawer of the surgical hub enclosure, in accordance with at least one aspect of the present disclosure.
Figure 5:
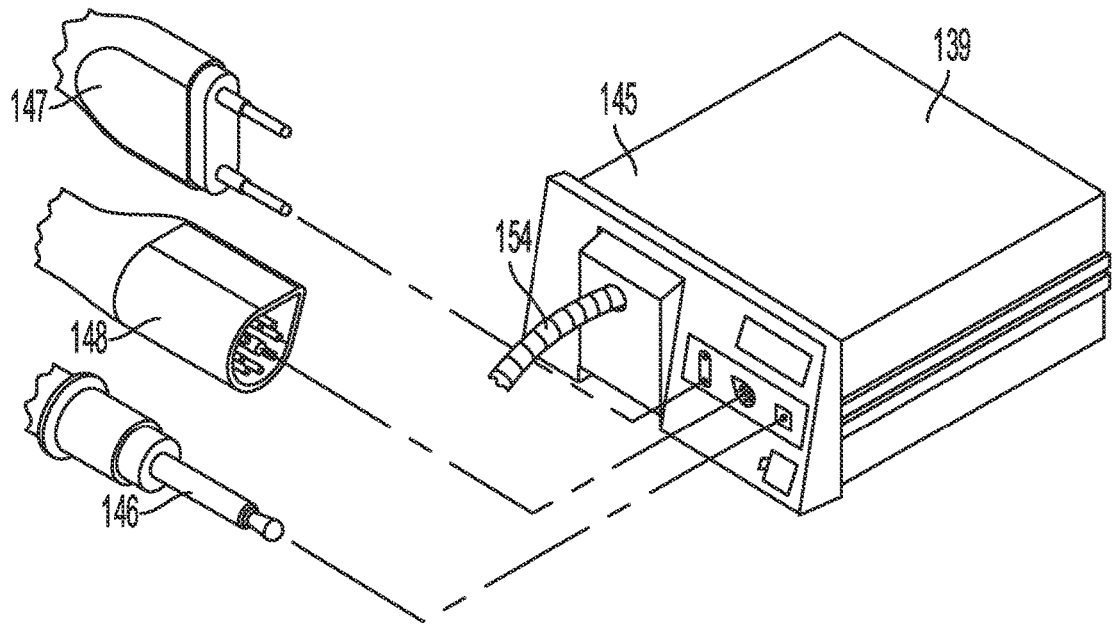
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
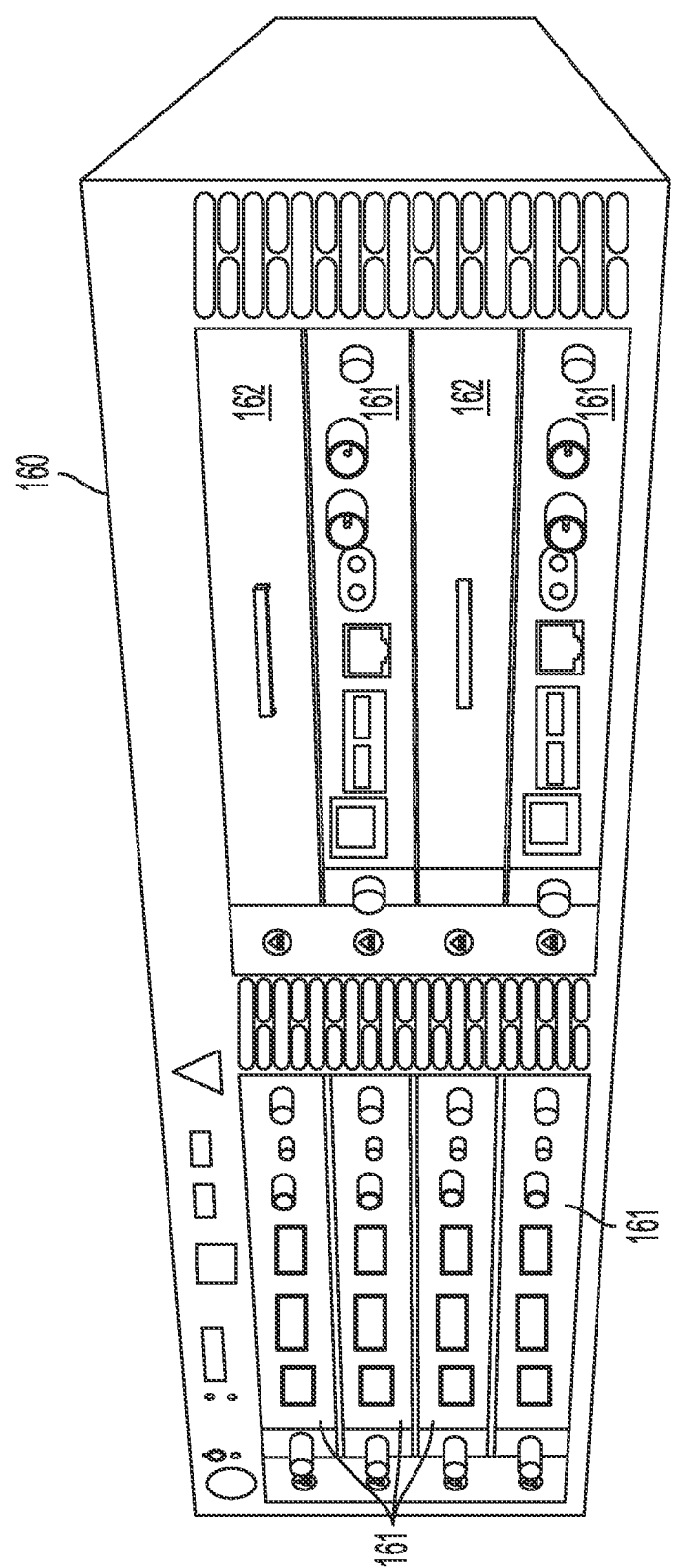
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
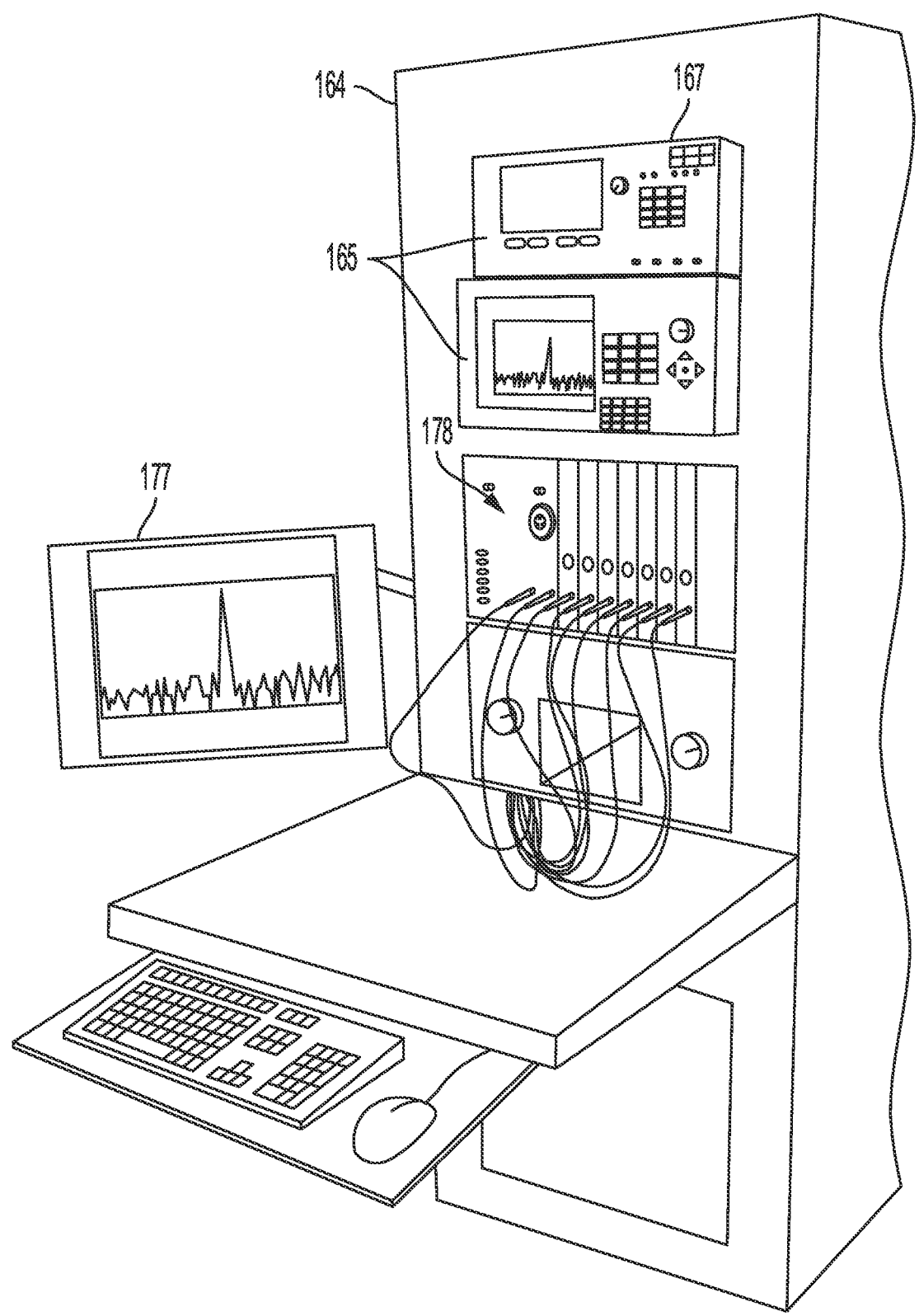
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
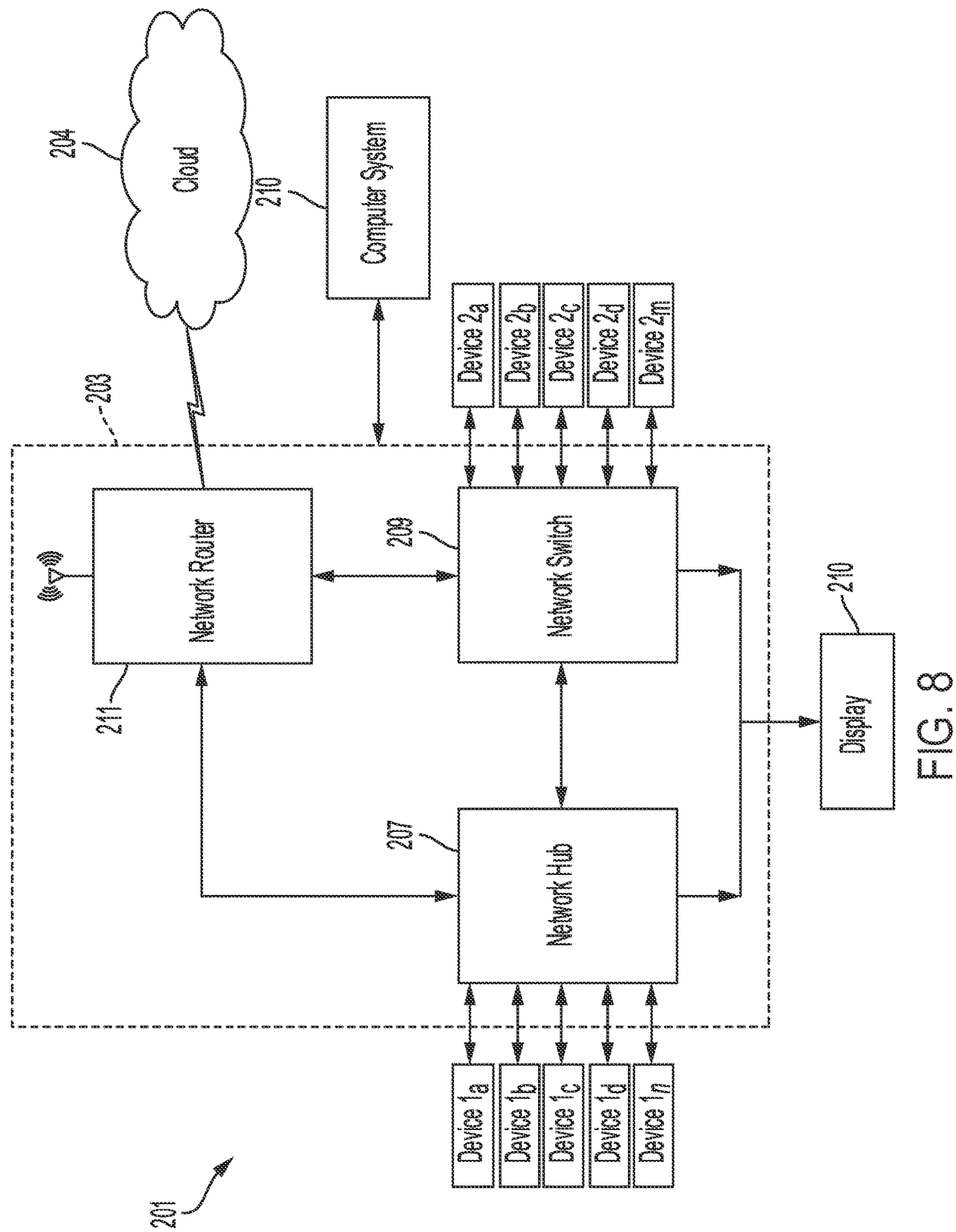
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as W-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
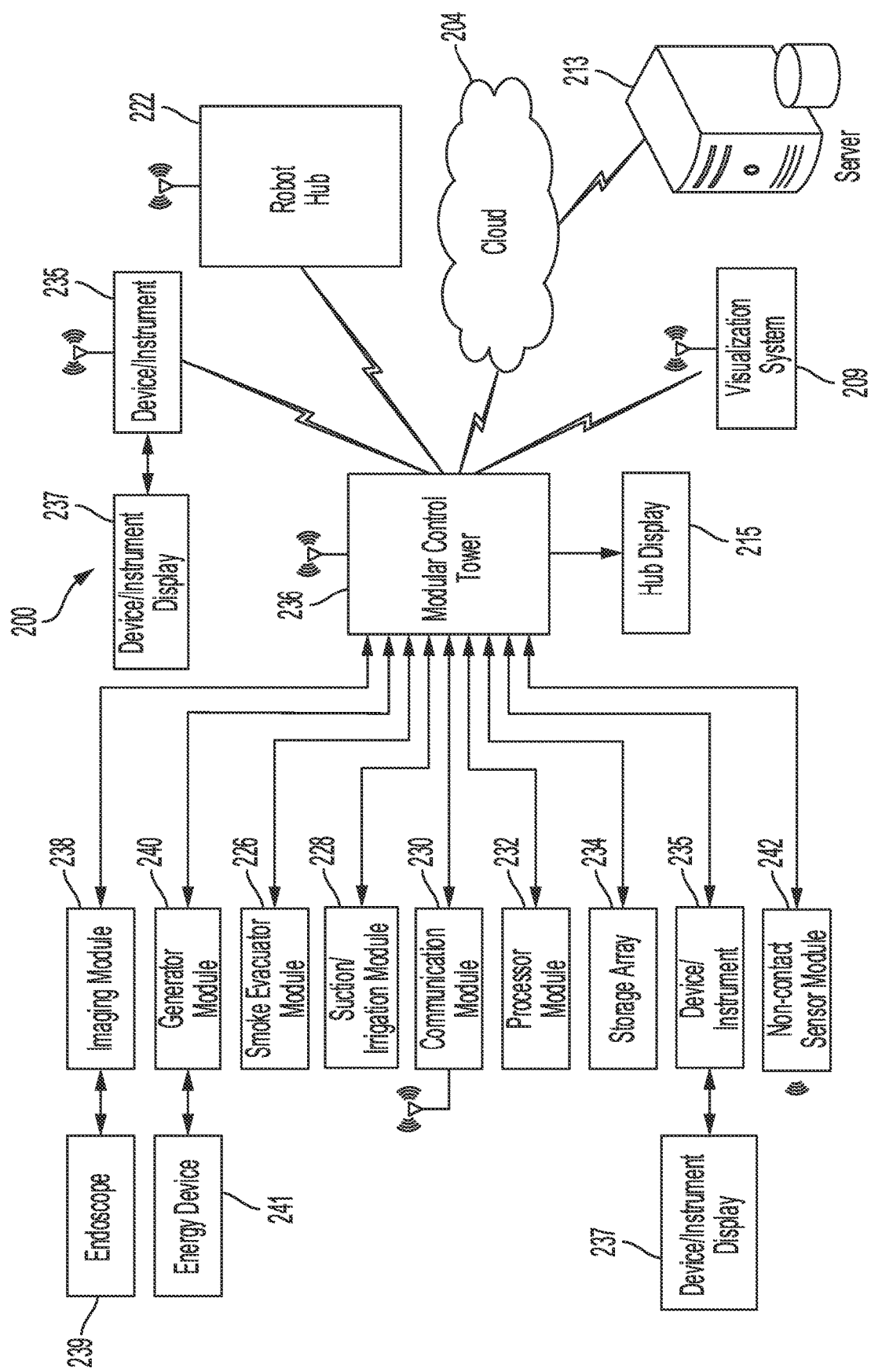
FIG. 9 illustrates a computer-implemented interactive surgical system, in accordance with at least one aspect of the present disclosure.
Figure 10:
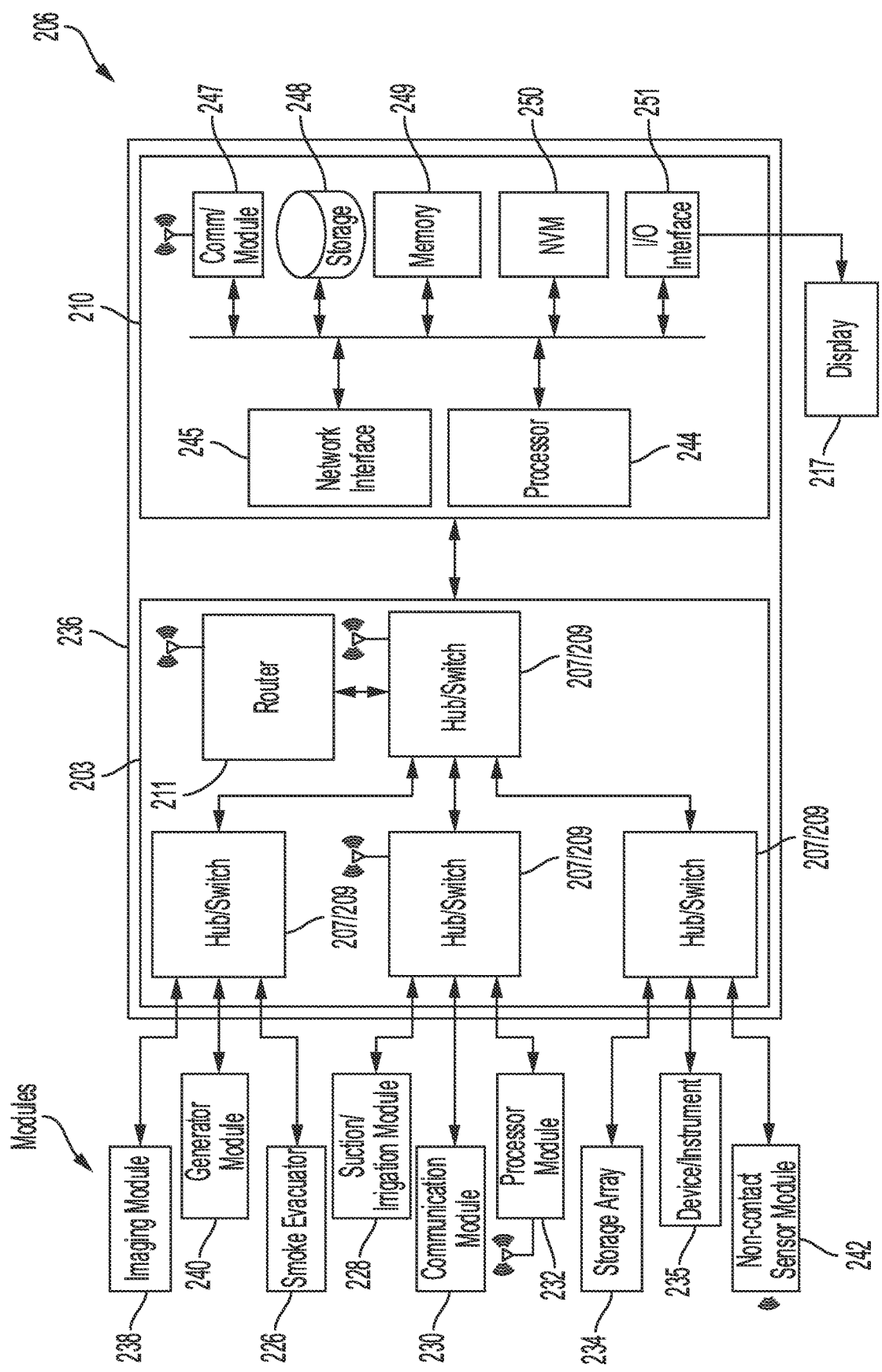
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
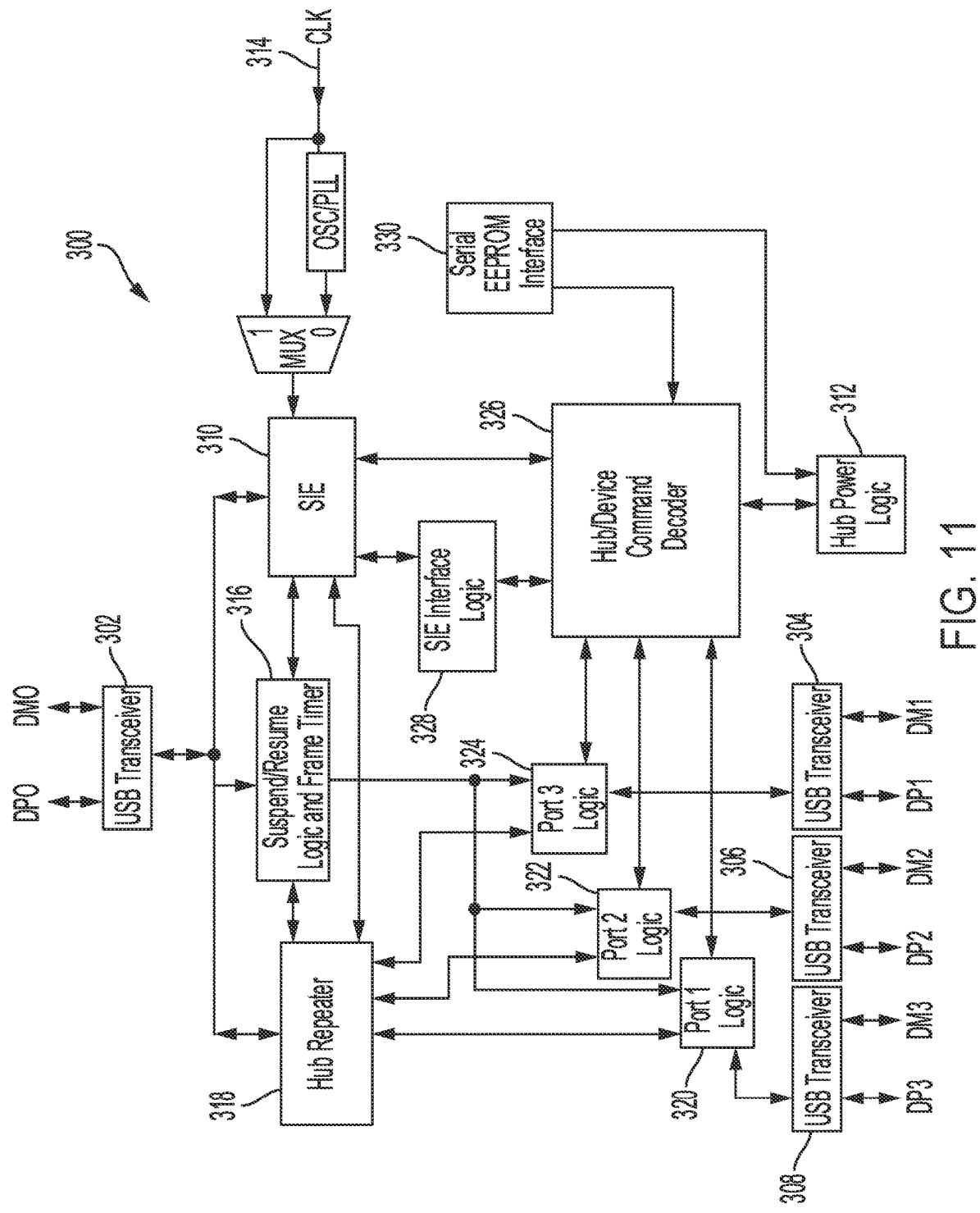
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
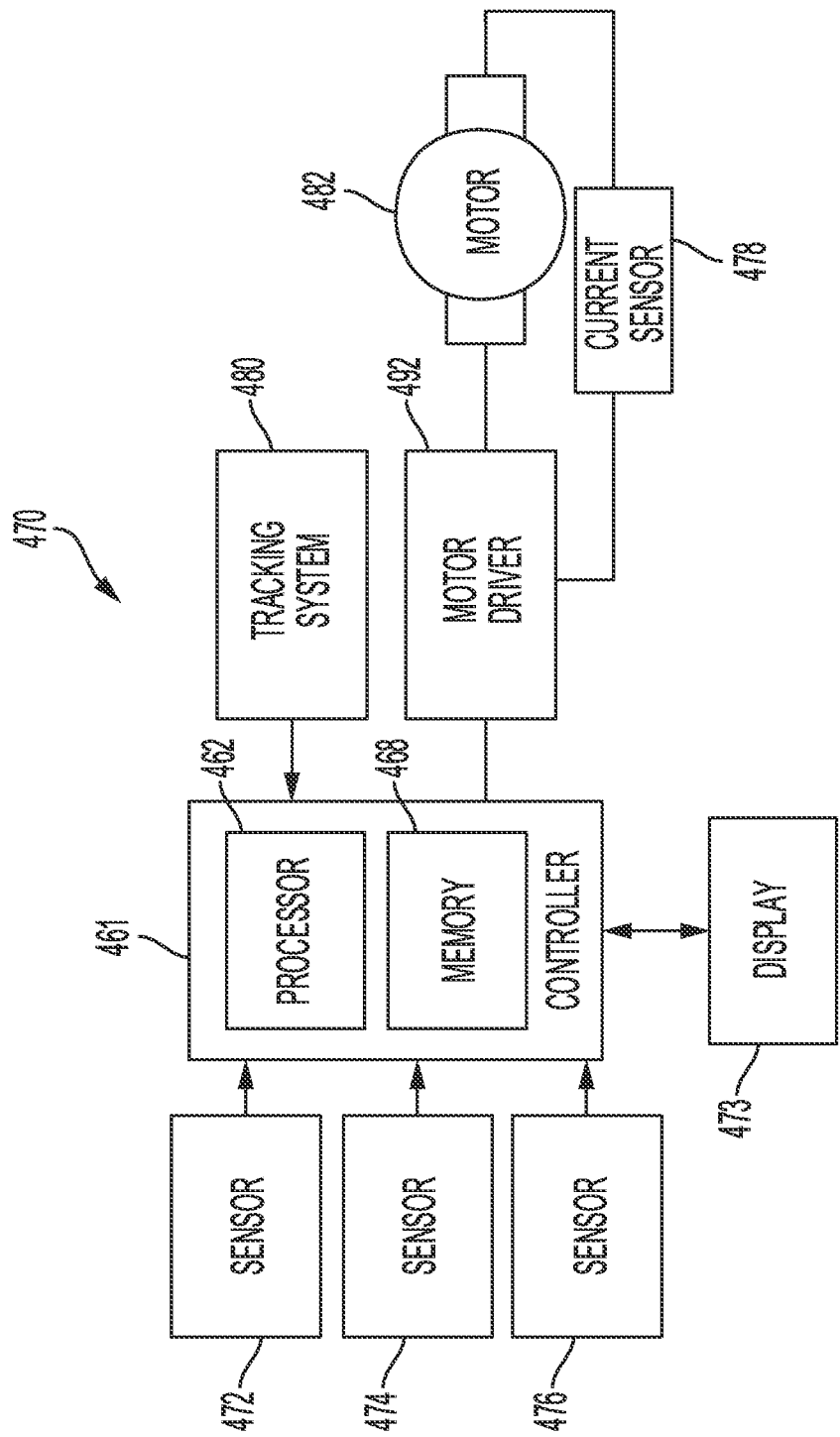
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive a clamp arm closure member. A tracking system 480 is configured to determine the position of the longitudinally movable displacement member. The position information is provided to the processor 462, which can be programmed or configured to determine the position of the longitudinally movable drive member as well as the position of the closure member. Additional motors may be provided at the tool driver interface to control closure tube travel, shaft rotation, articulation, or clamp arm closure, or a combination of the above. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife, articulation systems, clamp arm, or a combination of the above. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable battery cells. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a longitudinal displacement member to open and close a clamp arm, which can be adapted and configured to include a rack of drive teeth. In other aspects, the displacement member represents a clamp arm closure member configured to close and to open a clamp arm of a stapler, ultrasonic, or electrosurgical device, or combinations of the above. Accordingly, as used herein, the term displacement member is used generically to refer to any movable member of the surgical instrument or tool such as the drive member, the clamp arm, or any element that can be displaced. Accordingly, the absolute positioning system can, in effect, track the displacement of the clamp arm by tracking the linear displacement of the longitudinally movable drive member. In other aspects, the absolute positioning system can be configured to track the position of a clamp arm in the process of closing or opening. In various other aspects, the displacement member may be coupled to any position sensor 472 suitable for measuring linear displacement. Thus, the longitudinally movable drive member, or clamp arm, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member to open and close a clamp arm.

A single revolution of the sensor element associated with the position sensor 472 is equivalent to a longitudinal linear displacement $d_1$ of the displacement member, where $d_1$ is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement $d_1+d_2+ \ldots d_n$ of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertia, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil in a stapler or a clamp arm in an ultrasonic or electrosurgical instrument. The sensor 476, such as, for example, a load sensor, can measure the firing force applied to a closure member coupled to a clamp arm of the surgical instrument or tool or the force applied by a clamp arm to tissue located in the jaws of an ultrasonic or electrosurgical instrument. Alternatively, a current sensor 478 can be employed to measure the current drawn by the motor 482. The displacement member also may be configured to engage a clamp arm to open or close the clamp arm. The force sensor may be configured to measure the clamping force on tissue. The force required to advance the displacement member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A load sensor 476 can measure the force used to operate the clamp arm element, for example, to capture tissue between the clamp arm and an ultrasonic blade or to capture tissue between the clamp arm and a jaw of an electrosurgical instrument. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
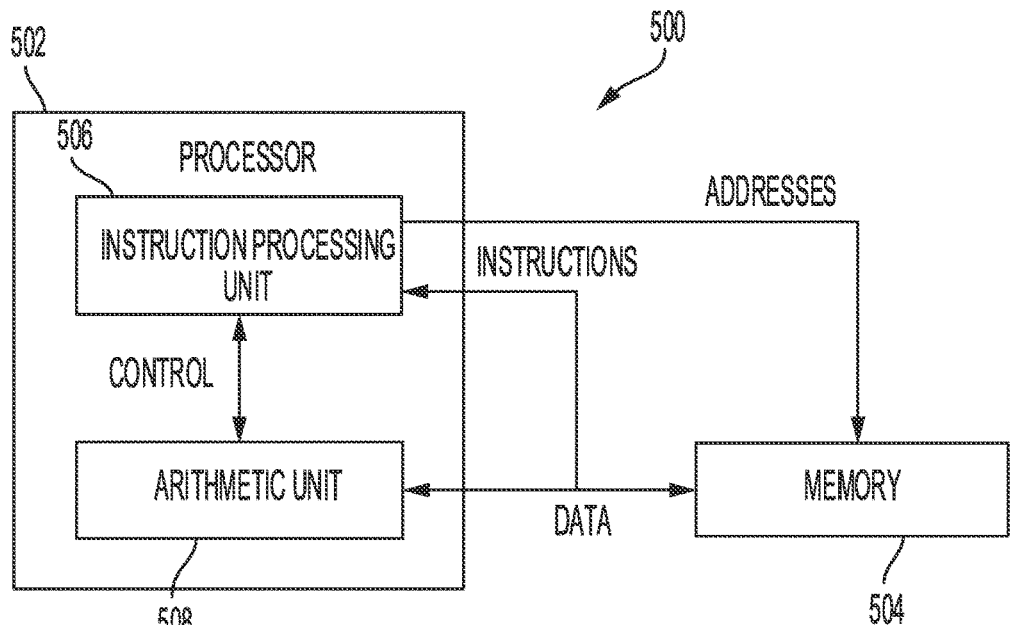
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
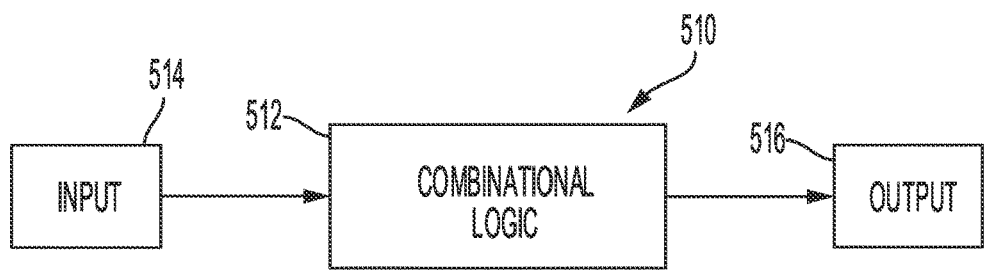
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
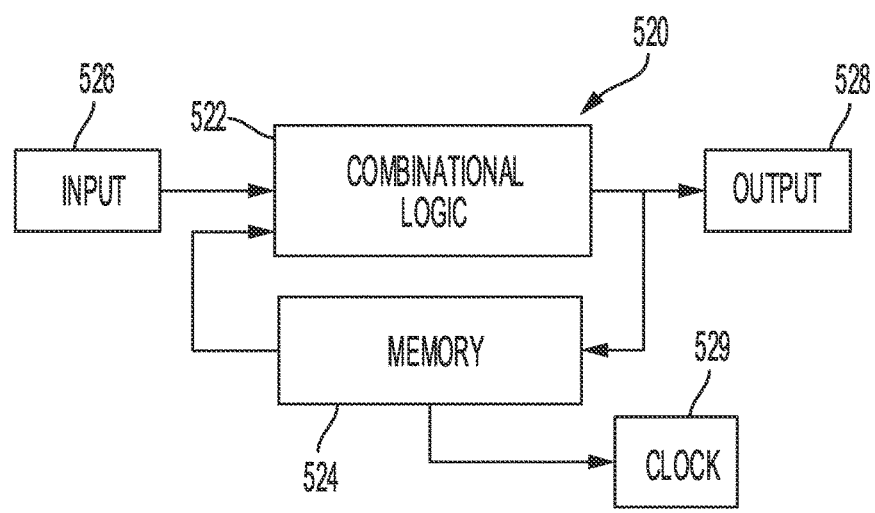
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
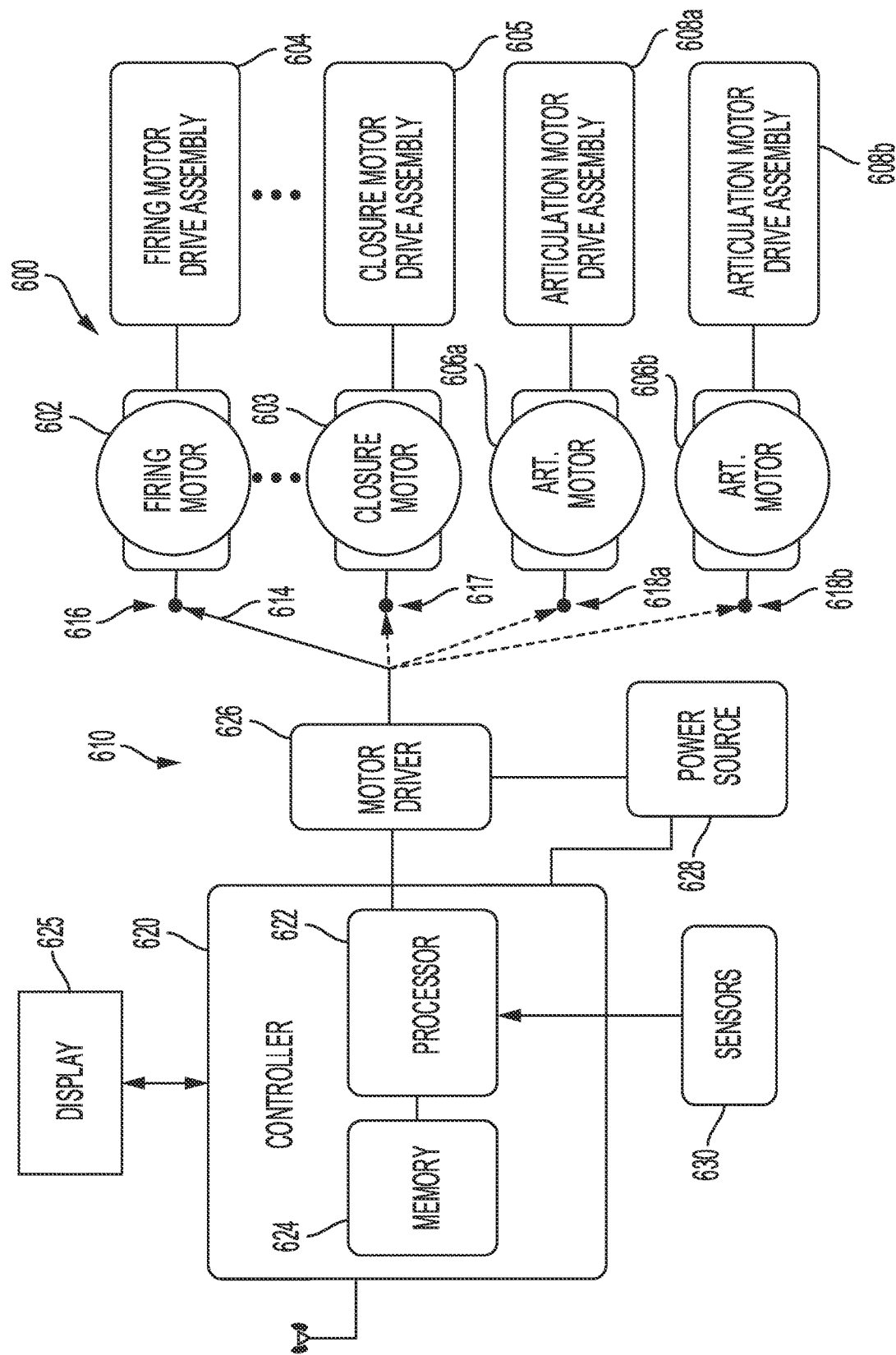
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the clamp arm closure member. The closure member may be retracted by reversing the direction of the motor 602, which also causes the clamp arm to open.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motor 603 may be operably coupled to a closure motor drive assembly 605 which can be configured to transmit closure motions, generated by the motor 603 to the end effector, in particular to displace a closure tube to close the clamp arm and compress tissue between the clamp arm and either an ultrasonic blade or jaw member of an electrosurgical device. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube or closure member to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example. In various aspects, the microcontroller 620 may communicate over a wired or wireless channel, or combinations thereof.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 622 is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the closure member coupled to the clamp arm of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
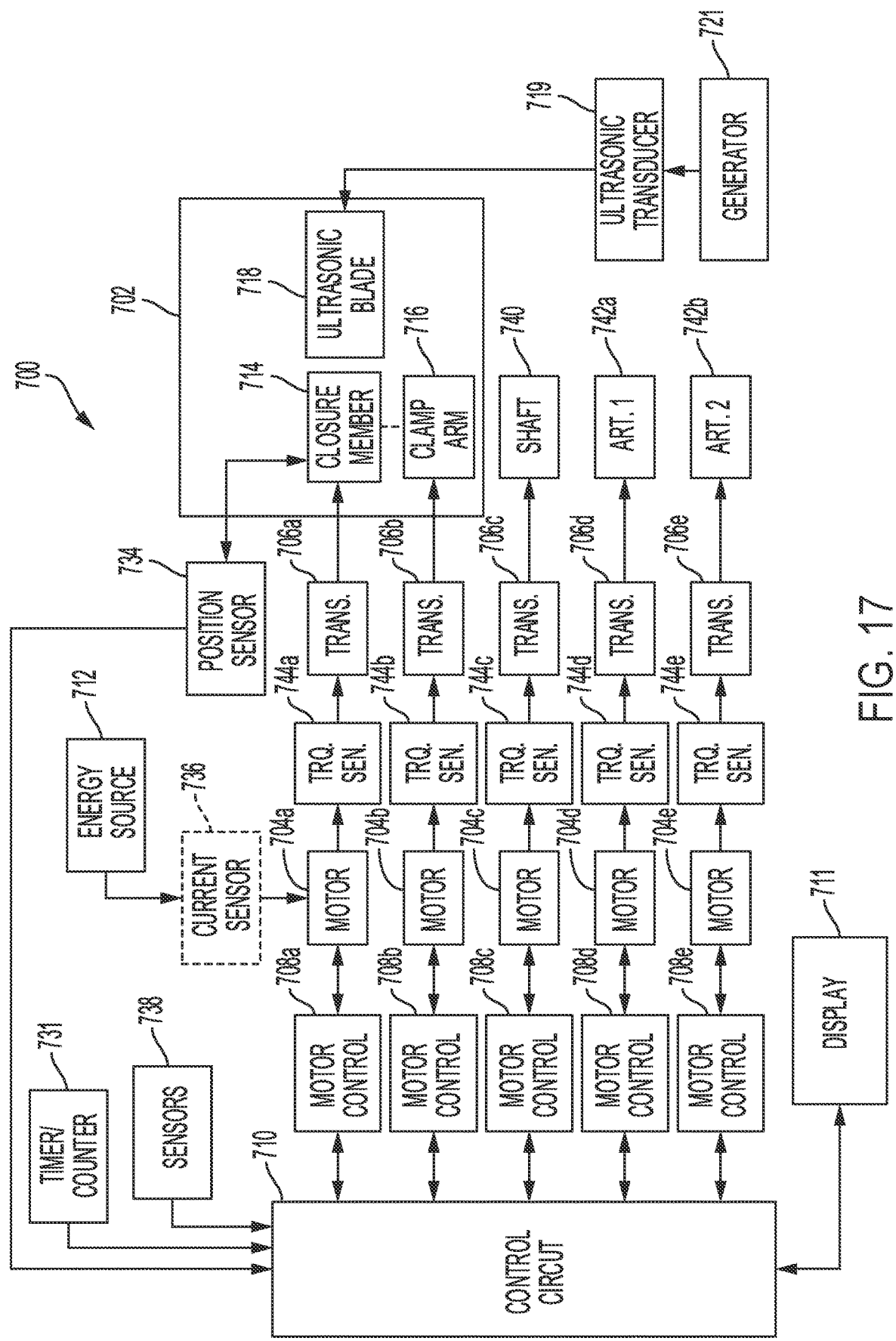
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, or one or more articulation members, or combinations thereof. The surgical instrument 700 comprises a control circuit 710 configured to control motor-driven firing members, closure members, shaft members, or one or more articulation members, or combinations thereof.

In one aspect, the robotic surgical instrument 700 comprises a control circuit 710 configured to control a clamp arm 716 and a closure member 714 portion of an end effector 702, an ultrasonic blade 718 coupled to an ultrasonic transducer 719 excited by an ultrasonic generator 721, a shaft 740, and one or more articulation members 742a, 742b via a plurality of motors 704a-704e. A position sensor 734 may be configured to provide position feedback of the closure member 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the closure member 714 as determined by the position sensor 734 with the output of the timer/counter 731 such that the control circuit 710 can determine the position of the closure member 714 at a specific time (t) relative to a starting position or the time (t) when the closure member 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the clamp arm 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the closure member 714, clamp arm 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the closure member 714. The position sensor 734 may be or include any type of sensor that is capable of generating position data that indicate a position of the closure member 714. In some examples, the position sensor 734 may include an encoder configured to provide a series of pulses to the control circuit 710 as the closure member 714 translates distally and proximally. The control circuit 710 may track the pulses to determine the position of the closure member 714. Other suitable position sensors may be used, including, for example, a proximity sensor. Other types of position sensors may provide other signals indicating motion of the closure member 714. Also, in some examples, the position sensor 734 may be omitted. Where any of the motors 704a-704e is a stepper motor, the control circuit 710 may track the position of the closure member 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the closure member 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the closure member 714. The transmission 706a comprises movable mechanical elements such as rotating elements and a firing member to control the movement of the closure member 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the closure member 714. A position sensor 734 may be configured to provide the position of the closure member 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the closure member 714 translates distally, the clamp arm 716 closes towards the ultrasonic blade 718.

In one aspect, the control circuit 710 is configured to drive a closure member such as the clamp arm 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the clamp arm 716. The transmission 706b comprises movable mechanical elements such as rotating elements and a closure member to control the movement of the clamp arm 716 from the open and closed positions. In one aspect, the motor 704b is coupled to a closure gear assembly, which includes a closure reduction gear set that is supported in meshing engagement with the closure spur gear. The torque sensor 744*b* provides a closure force feedback signal to the control circuit 710. The closure force feedback signal represents the closure force applied to the clamp arm 716. The position sensor 734 may be configured to provide the position of the closure member as a feedback signal to the control circuit 710. Additional sensors 738 in the end effector 702 may provide the closure force feedback signal to the control circuit 710. The pivotable clamp arm 716 is positioned opposite the ultrasonic blade 718. When ready to use, the control circuit 710 may provide a closure signal to the motor control 708*b*. In response to the closure signal, the motor 704*b* advances a closure member to grasp tissue between the clamp arm 716 and the ultrasonic blade 718.

In one aspect, the control circuit 710 is configured to rotate a shaft member such as the shaft 740 to rotate the end effector 702. The control circuit 710 provides a motor set point to a motor control 708*c*, which provides a drive signal to the motor 704*c*. The output shaft of the motor 704*c* is coupled to a torque sensor 744*c*. The torque sensor 744*c* is coupled to a transmission 706*c* which is coupled to the shaft 740. The transmission 706*c* comprises movable mechanical elements such as rotating elements to control the rotation of the shaft 740 clockwise or counterclockwise up to and over 360°. In one aspect, the motor 704*c* is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744*c* provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708*d*, which provides a drive signal to the motor 704*d*. The output shaft of the motor 704*d* is coupled to a torque sensor 744*d*. The torque sensor 744*d* is coupled to a transmission 706*d* which is coupled to an articulation member 742*a*. The transmission 706*d* comprises movable mechanical elements such as articulation elements to control the articulation of the end effector 702±65°. In one aspect, the motor 704*d* is coupled to an articulation nut, which is rotatably journaled on the proximal end portion of the distal spine portion and is rotatably driven thereon by an articulation gear assembly. The torque sensor 744*d* provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742*a*, 742*b*. These articulation members 742*a*, 742*b* are driven by separate disks on the robot interface (the rack) which are driven by the two motors 708*d*, 708*e*. When the separate firing motor 704*a* is provided, each of articulation links 742*a*, 742*b* can be antagonistically driven with respect to the other link in order to provide a resistive holding motion and a load to the head when it is not moving and to provide an articulation motion as the head is articulated. The articulation members 742*a*, 742*b* attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704*a*-704*e* may comprise a brushed DC motor with a gearbox and mechanical links to a firing member, closure member, or articulation member. Another example includes electric motors 704*a*-704*e* that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704*a*-704*e*. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the clamp arm 716 to determine tissue location using segmented electrodes. The torque sensors 744*a*-744*e* may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the ultrasonic blade 718 has tissue on it, and (4) the load and position on both articulation rods.

In one aspect, the one or more sensors 738 may comprise a strain gauge, such as a micro-strain gauge, configured to measure the magnitude of the strain in the clamp arm 716 during a clamped condition. The strain gauge provides an electrical signal whose amplitude varies with the magnitude of the strain. The sensors 738 may comprise a pressure sensor configured to detect a pressure generated by the presence of compressed tissue between the clamp arm 716 and the ultrasonic blade 718. The sensors 738 may be configured to detect impedance of a tissue section located between the clamp arm 716 and the ultrasonic blade 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the clamp arm 716 by the closure drive system. For example, one or more sensors 738 can be at an interaction point between the closure tube and the clamp arm 716 to detect the closure forces applied by the closure tube to the clamp arm 716. The forces exerted on the clamp arm 716 can be representative of the tissue compression experienced by the tissue section captured between the clamp arm 716 and the ultrasonic blade 718. The one or more sensors 738 can be positioned at various interaction points along the closure drive system to detect the closure forces applied to the clamp arm 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the clamp arm 716.

In one aspect, a current sensor 736 can be employed to measure the current drawn by each of the motors 704a-704e. The force required to advance any of the movable mechanical elements such as the closure member 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move the closure member 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
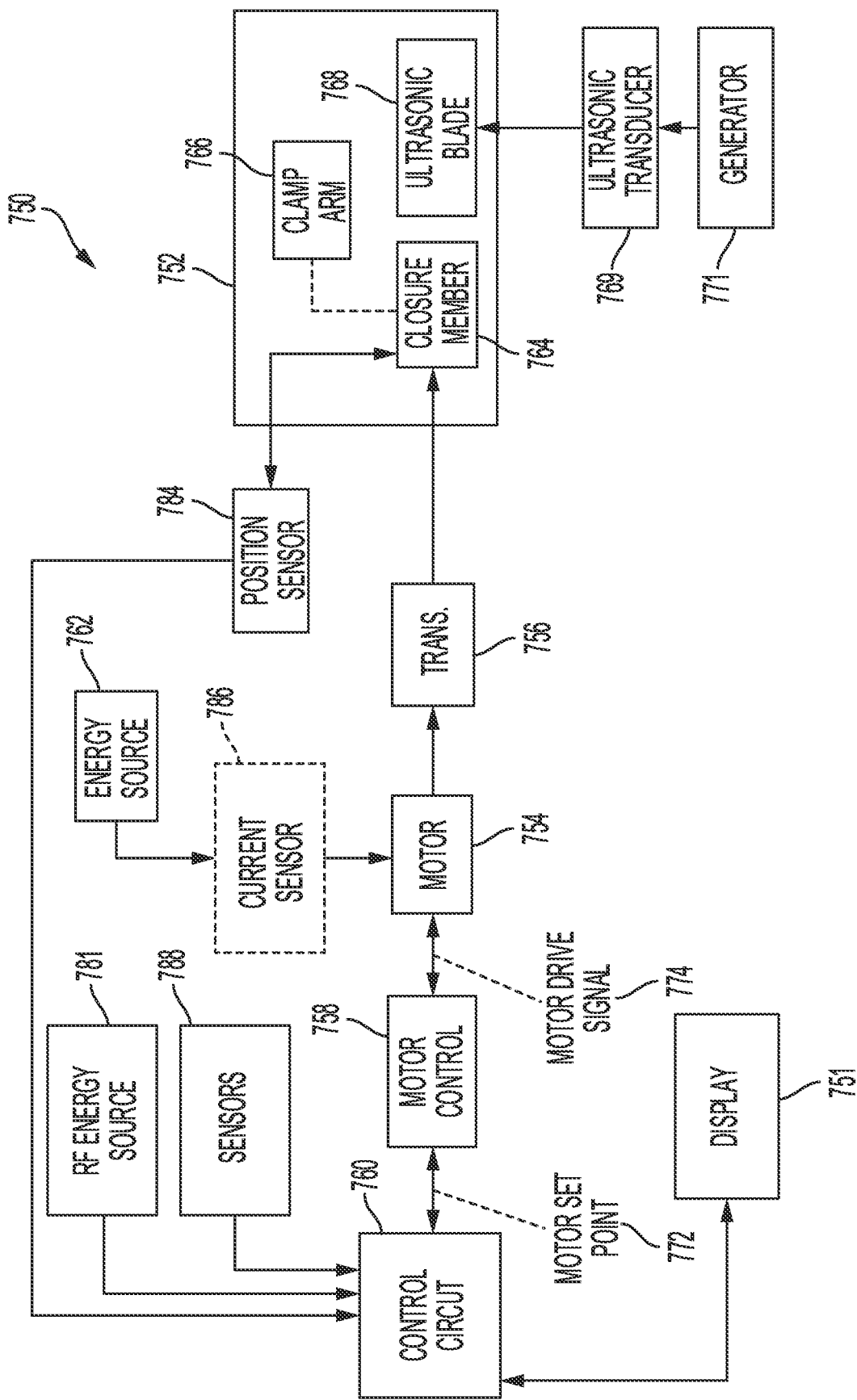
FIG. 18 illustrates a block diagram of a surgical instrument programmed to control the distal translation of a displacement member, in accordance with at least one aspect of the present disclosure.

FIG. 18 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
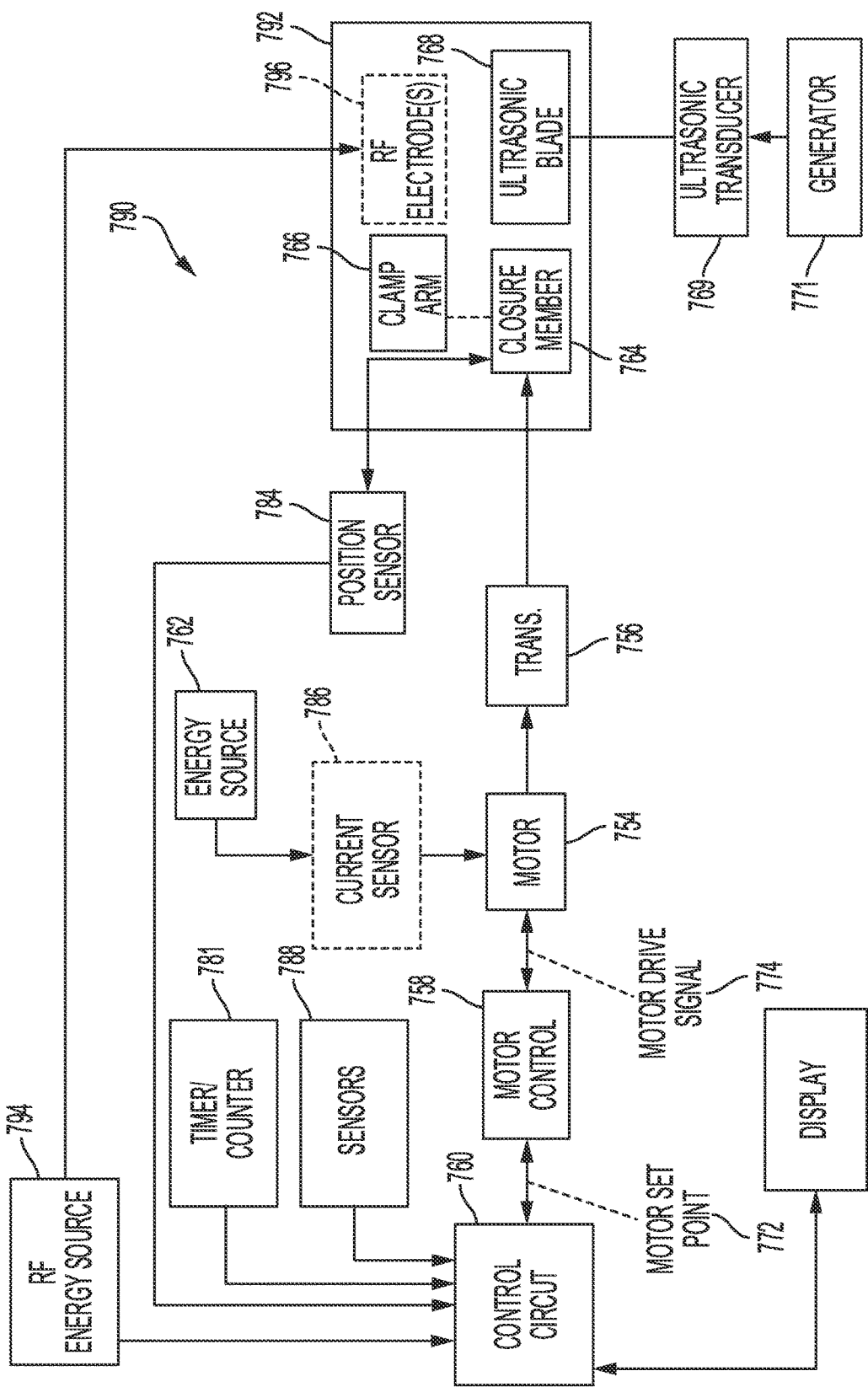
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the closure member 764. The surgical instrument 790 comprises an end effector 792 that may comprise a clamp arm 766, a closure member 764, and an ultrasonic blade 768 which may be interchanged with or work in conjunction with one or more RF electrodes 796 (shown in dashed line). The ultrasonic blade 768 is coupled to an ultrasonic transducer 769 driven by an ultrasonic generator 771.

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In some examples, the position sensor 784 may be omitted. Where the motor 754 is a stepper motor, the control circuit 760 may track the position of the closure member 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

An RF energy source 794 is coupled to the end effector 792 and is applied to the RF electrode 796 when the RF electrode 796 is provided in the end effector 792 in place of the ultrasonic blade 768 or to work in conjunction with the ultrasonic blade 768. For example, the ultrasonic blade is made of electrically conductive metal and may be employed as the return path for electrosurgical RF current. The control circuit 760 controls the delivery of the RF energy to the RF electrode 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Generator Hardware

In various aspects smart ultrasonic energy devices may comprise adaptive algorithms to control the operation of the ultrasonic blade. In one aspect, the ultrasonic blade adaptive control algorithms are configured to identify tissue type and adjust device parameters. In one aspect, the ultrasonic blade control algorithms are configured to parameterize tissue type. An algorithm to detect the collagen/elastic ratio of tissue to tune the amplitude of the distal tip of the ultrasonic blade is described in the following section of the present disclosure. Various aspects of smart ultrasonic energy devices are described herein in connection with FIGS. 12-19, for example. Accordingly, the following description of adaptive ultrasonic blade control algorithms should be read in conjunction with FIGS. 12-19 and the description associated therewith.

In certain surgical procedures it would be desirable to employ adaptive ultrasonic blade control algorithms. In one aspect, adaptive ultrasonic blade control algorithms may be employed to adjust the parameters of the ultrasonic device based on the type of tissue in contact with the ultrasonic blade. In one aspect, the parameters of the ultrasonic device may be adjusted based on the location of the tissue within the jaws of the ultrasonic end effector, for example, the location of the tissue between the clamp arm and the ultrasonic blade. The impedance of the ultrasonic transducer may be employed to differentiate what percentage of the tissue is located in the distal or proximal end of the end effector. The reactions of the ultrasonic device may be based on the tissue type or compressibility of the tissue. In another aspect, the parameters of the ultrasonic device may be adjusted based on the identified tissue type or parameterization. For example, the mechanical displacement amplitude of the distal tip of the ultrasonic blade may be tuned based on the ration of collagen to elastin tissue detected during the tissue identification procedure. The ratio of collagen to elastin tissue may be detected used a variety of techniques including infrared (IR) surface reflectance and emissivity. The force applied to the tissue by the clamp arm and/or the stroke of the clamp arm to produce gap and compression. Electrical continuity across a jaw equipped with electrodes may be employed to determine what percentage of the jaw is covered with tissue.

Figure 20:
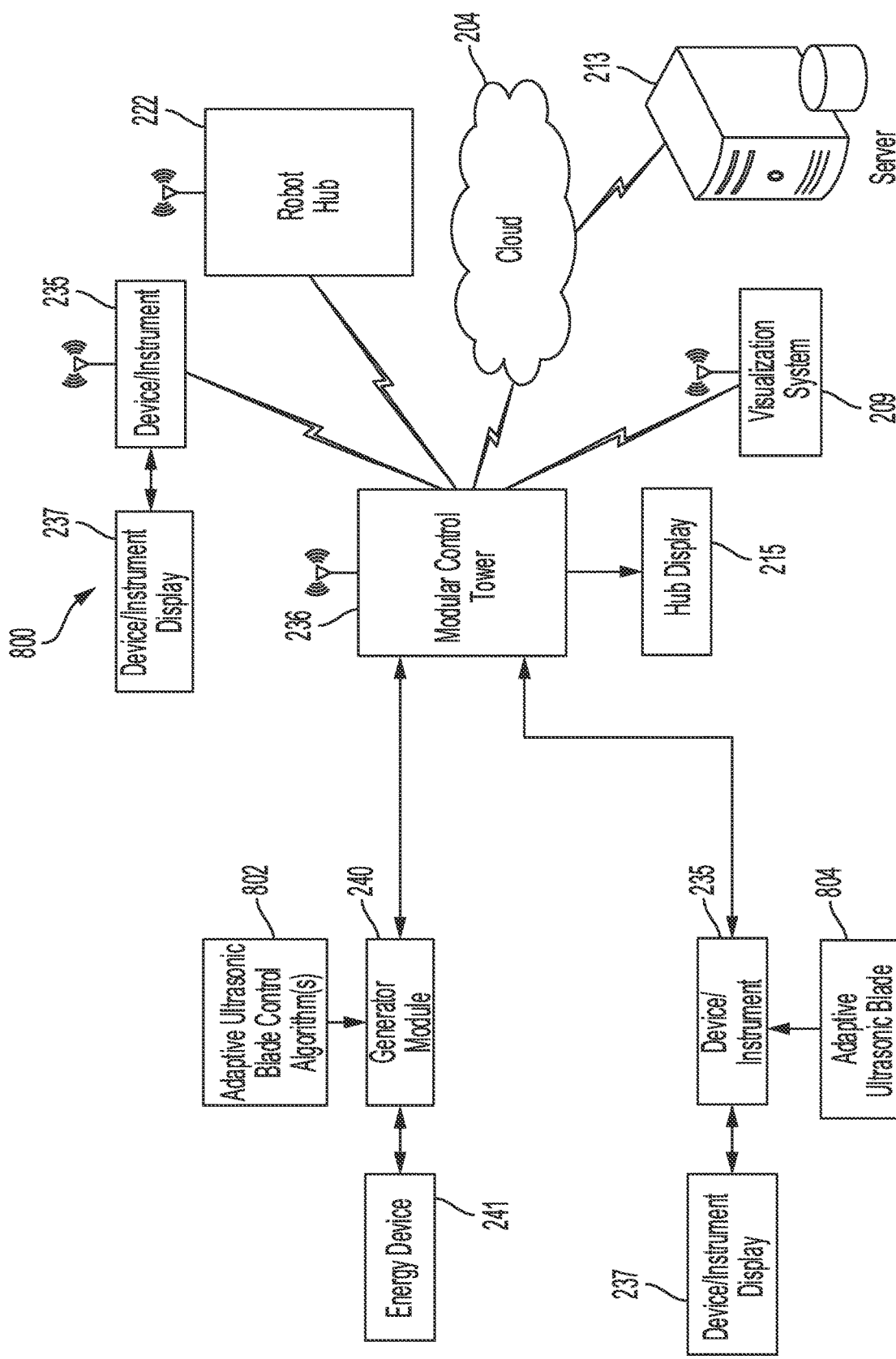
FIG. 20 is a system configured to execute adaptive ultrasonic blade control algorithms in a surgical data network comprising a modular communication hub, in accordance with at least one aspect of the present disclosure.

FIG. 20 is a system 800 configured to execute adaptive ultrasonic blade control algorithms in a surgical data network comprising a modular communication hub, in accordance with at least one aspect of the present disclosure. In one aspect, the generator module 240 is configured to execute the adaptive ultrasonic blade control algorithm(s) 802. In another aspect, the device/instrument 235 is configured to execute the adaptive ultrasonic blade control algorithm(s) 804. In another aspect, both the generator module 240 and the device/instrument 235 are configured to execute the adaptive ultrasonic blade control algorithms 802, 804.

The generator module 240 may comprise a patient isolated stage in communication with a non-isolated stage via a power transformer. A secondary winding of the power transformer is contained in the isolated stage and may comprise a tapped configuration (e.g., a center-tapped or a non-center-tapped configuration) to define drive signal outputs for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, the drive signal outputs may output an ultrasonic drive signal (e.g., a 420V root-mean-square (RMS) drive signal) to an ultrasonic surgical instrument 241, and the drive signal outputs may output an RF electrosurgical drive signal (e.g., a 100V RMS drive signal) to an RF electrosurgical instrument 241. Aspects of the generator module 240 are described herein with reference to FIGS. 21-22.

The generator module 240 or the device/instrument 235 or both are coupled the modular control tower 236 connected to multiple operating theater devices such as, for example, intelligent surgical instruments, robots, and other computerized devices located in the operating theater, as described with reference to FIGS. 8-11, for example.

Figure 21:
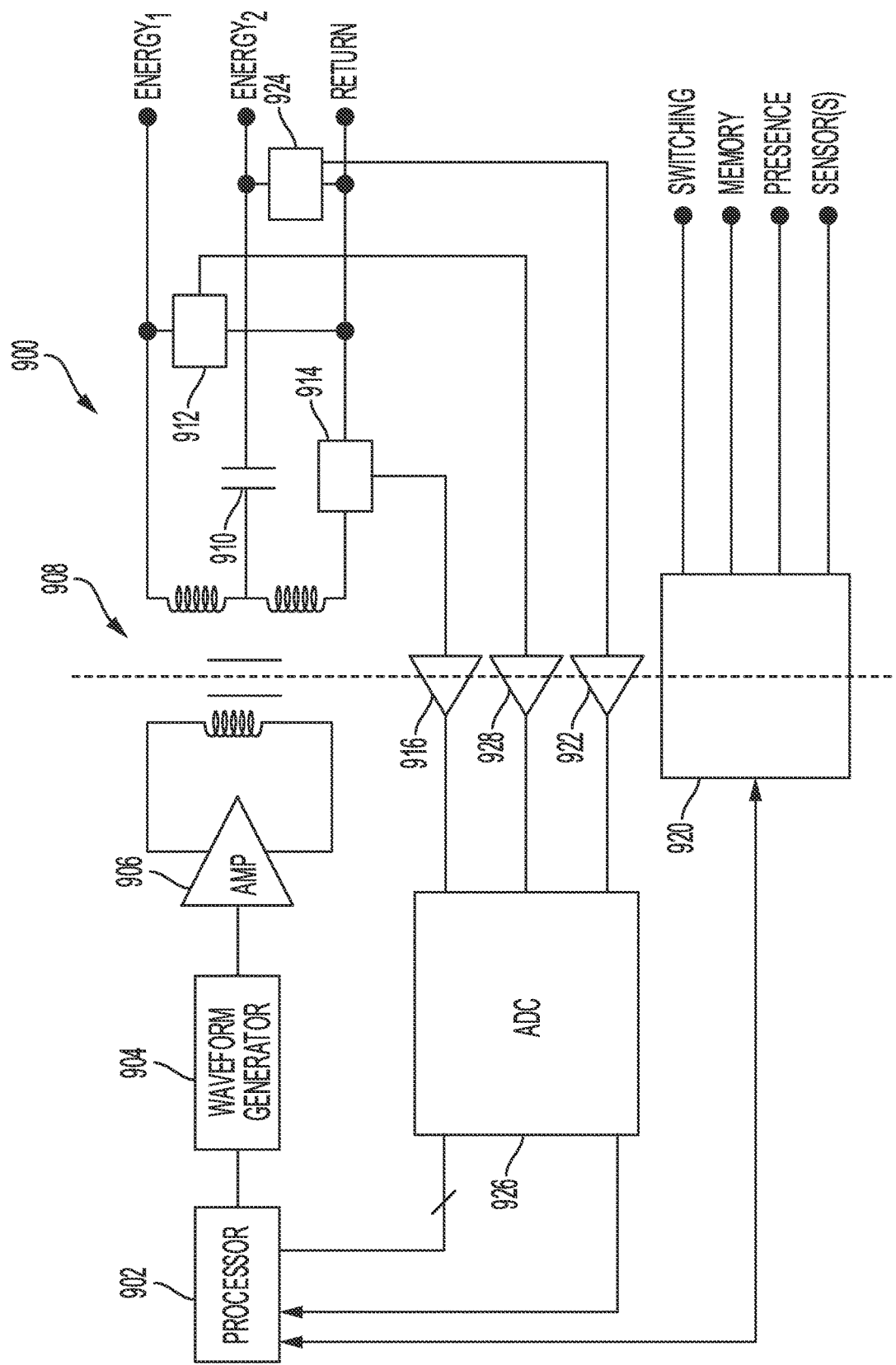
FIG. 21 illustrates an example of a generator, in accordance with at least one aspect of the present disclosure.

FIG. 21 illustrates an example of a generator 900, which is one form of a generator configured to couple to an ultrasonic instrument and further configured to execute adaptive ultrasonic blade control algorithms in a surgical data network comprising a modular communication hub as shown in FIG. 20. The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY$_1$ and RETURN. A second signal of a second energy modality is coupled across a capacitor 910 and is provided to the surgical instrument between the terminals labeled ENERGY$_2$ and RETURN. It will be appreciated that more than two energy modalities may be output and thus the subscript "n" may be used to designate that up to n ENERGY$_n$ terminals may be provided, where n is a positive integer greater than 1. It also will be appreciated that up to "n" return paths RETURN$_n$ may be provided without departing from the scope of the present disclosure.

A first voltage sensing circuit 912 is coupled across the terminals labeled ENERGY$_1$ and the RETURN path to measure the output voltage therebetween. A second voltage sensing circuit 924 is coupled across the terminals labeled ENERGY$_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY$_1$/RETURN or the second voltage sensing circuit 924 coupled across the terminals labeled ENERGY$_2$/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY$_1$ may be ultrasonic energy and the second energy modality ENERGY$_2$ may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURN$_n$ may be provided for each energy modality ENERGY$_n$. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY$_1$ and RETURN as shown in FIG. 21. In one example, a connection of RF bipolar electrodes to the generator 900 output would be preferably located between the output labeled ENERGY$_2$ and RETURN. In the case of monopolar output, the preferred connections would be active electrode (e.g., pencil or other probe) to the ENERGY$_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to W-Fi (IEEE 802.11 family), WMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 22:
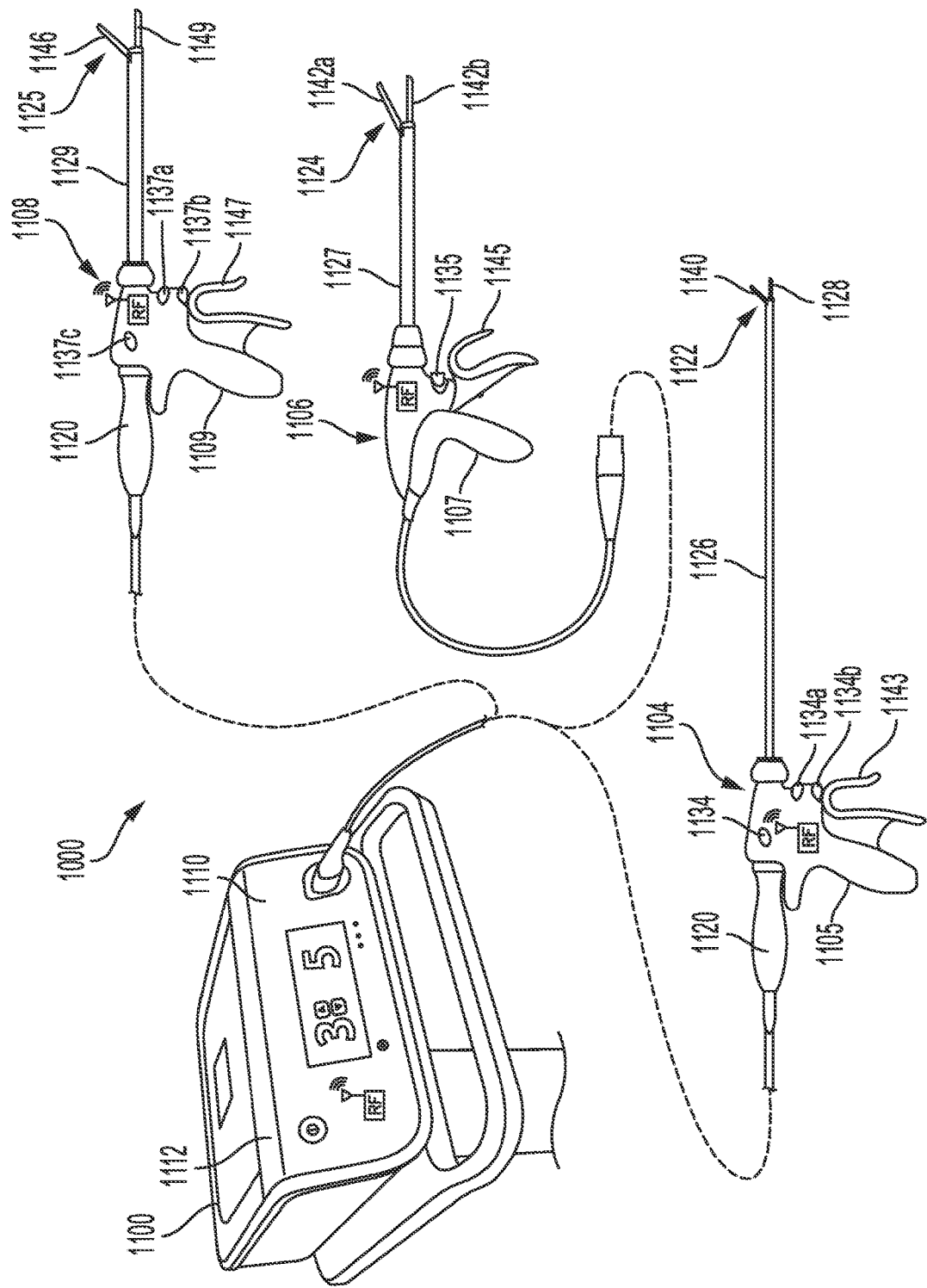
FIG. 22 is a surgical system comprising a generator and various surgical instruments usable therewith, in accordance with at least one aspect of the present disclosure.

FIG. 22 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 22 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1134a, 1134b, 1134c to energize and drive the ultrasonic blade 1128 or other function. The toggle buttons 1134a, 1134b, 1134c can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1142a, 1142b and return through an electrical conductor portion of the shaft 1127. The electrodes are coupled to and energized by a bipolar energy source within the generator 1100. The handpiece 1107 comprises a trigger 1145 to operate the clamp arms 1142a, 1142b and an energy button 1135 to actuate an energy switch to energize the electrodes in the end effector 1124.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 1137a, 1137b, 1137c to energize and drive the ultrasonic blade 1149 or other function. The toggle buttons 1137a, 1137b, 1137c can be configured to energize the ultrasonic transducer 1120 with the generator 1100 and energize the ultrasonic blade 1149 with a bipolar energy source also contained within the generator 1100.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 22 the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in US patent publication US-2017-0086914-A1, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 23:
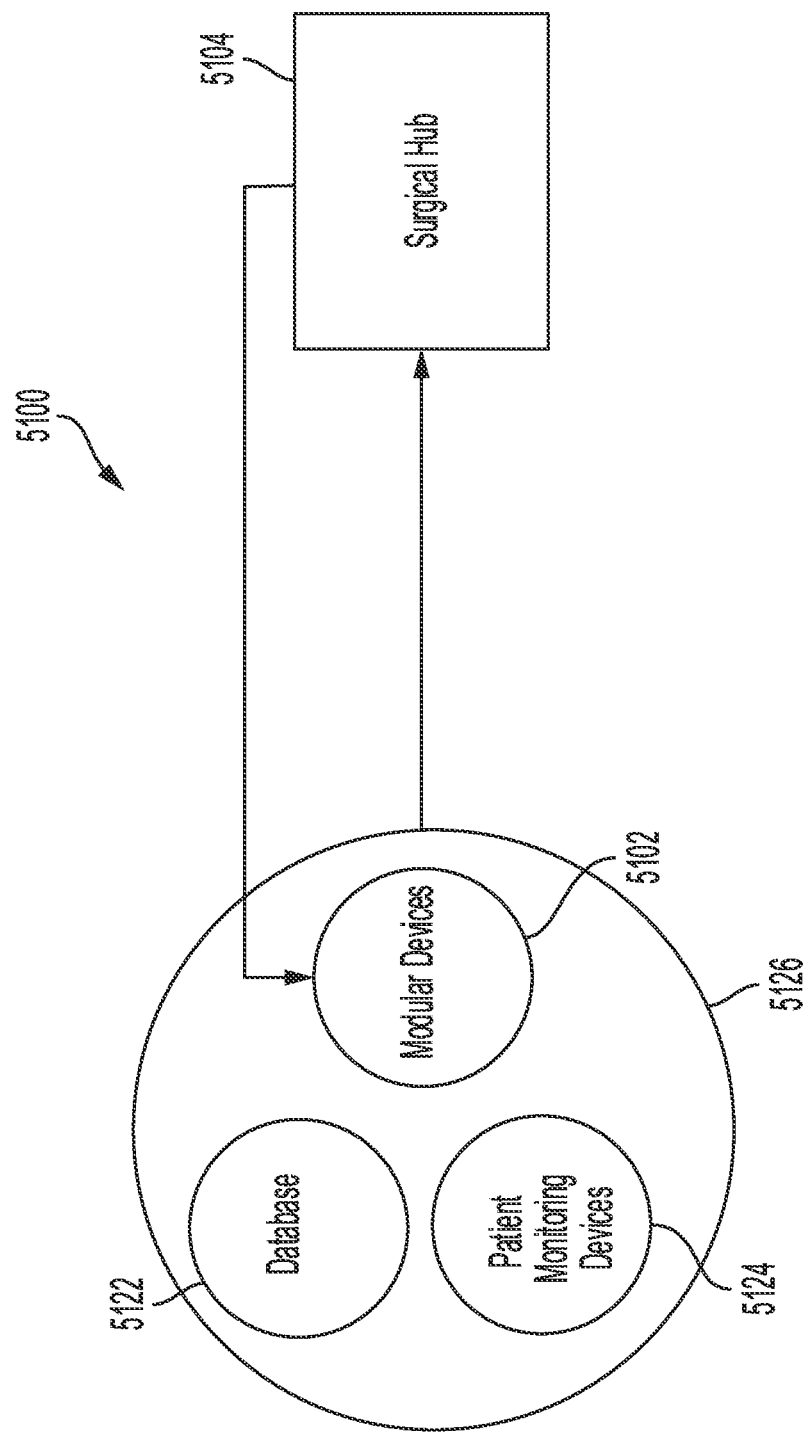
FIG. 23 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 23 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure (scanned by a scanner, for example) and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-11, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 24-30. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIGS. 3 and 4. The modular energy system 2000 can also include a variety of different components or accessories that are also connectable to or otherwise associatable with the modules 2001. In another aspect, the modular energy system 2000 can be embodied as a generator module 140, 240 (FIGS. 3 and 10) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 24:
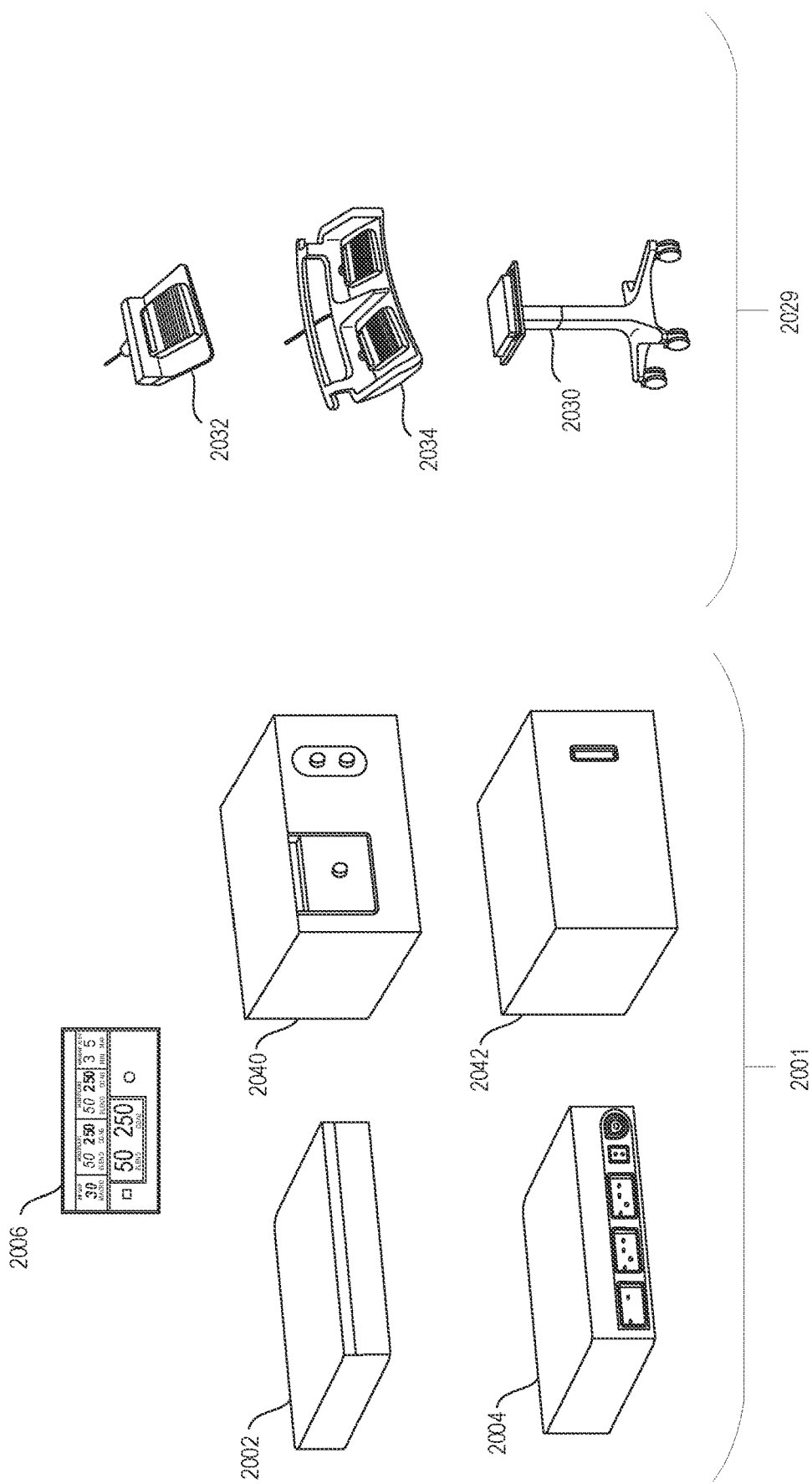
FIG. 24 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 24. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140, 240 (FIGS. 3 and 10), can be configured to generate one or multiple energy modalities for driving electrosurgical and/or ultrasonic surgical instruments connected thereto, such as is described above in connection with the generator 900 illustrated in FIG. 21. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-11.

Figure 29:
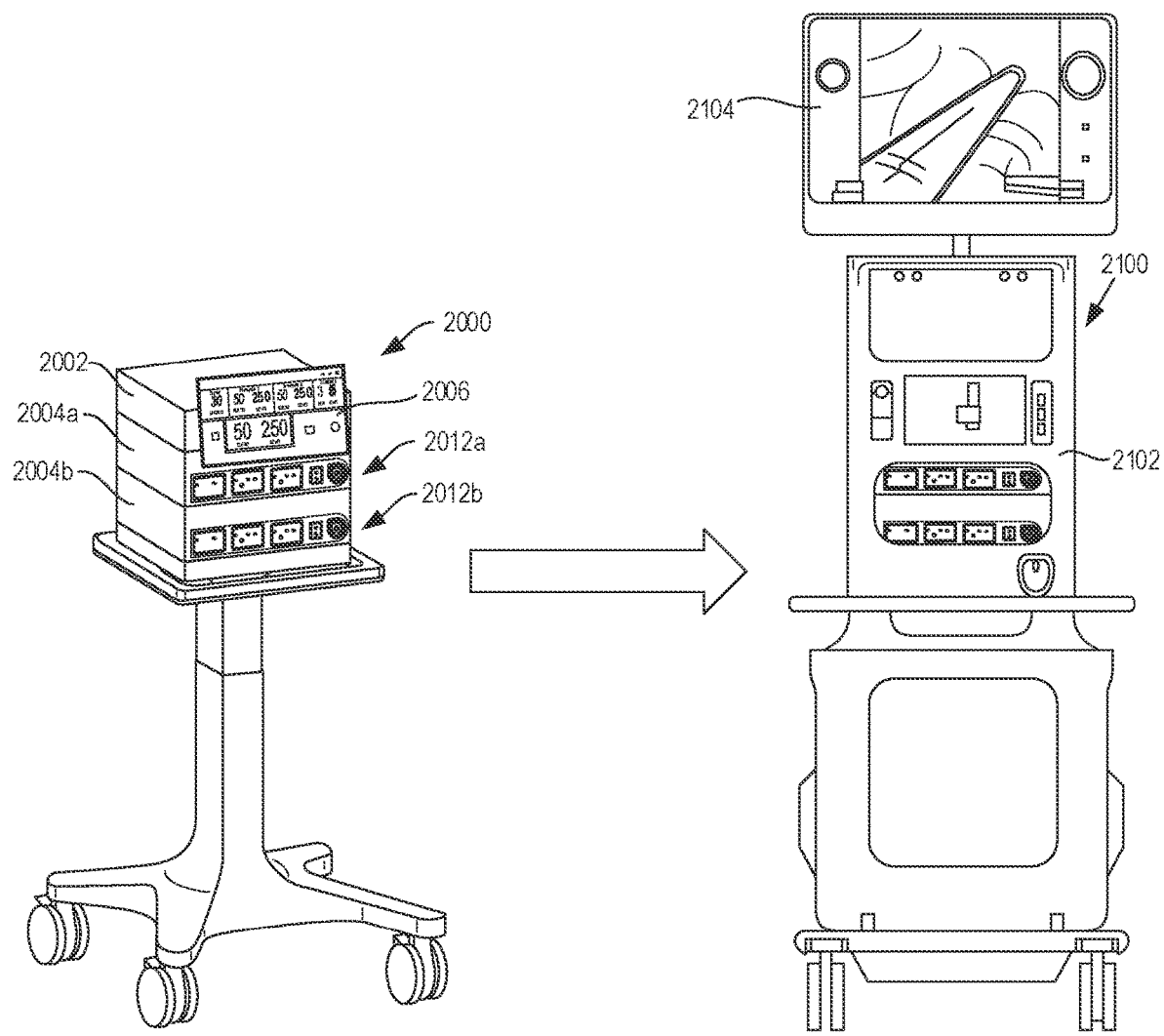
FIG. 29 is a diagram of a modular energy system including communicably connectable surgical platforms, in accordance with at least one aspect of the present disclosure.

Referring now to FIG. 25A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 30. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 29. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 25A, the energy module 2004 can include a port assembly 2012 including a number of different ports configured to deliver different energy modalities to corresponding surgical instruments that are connectable thereto. In the particular aspect illustrated in FIGS. 24-30, the port assembly 2012 includes a bipolar port 2014, a first monopolar port 2016a, a second monopolar port 2018b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 25A and 25B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 26A:
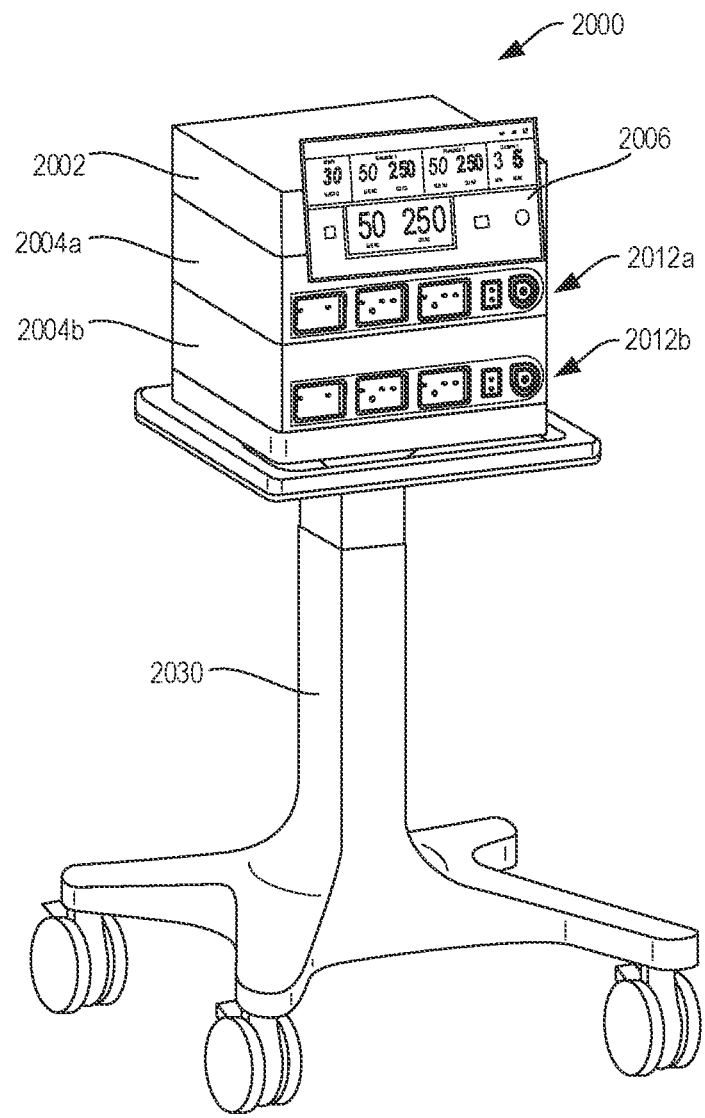
FIG. 26A is a second illustrative modular energy system configuration including a header module, a display screen, an energy module, and an expanded energy module connected together and mounted to a cart, in accordance with at least one aspect of the present disclosure.
Figure 26B:
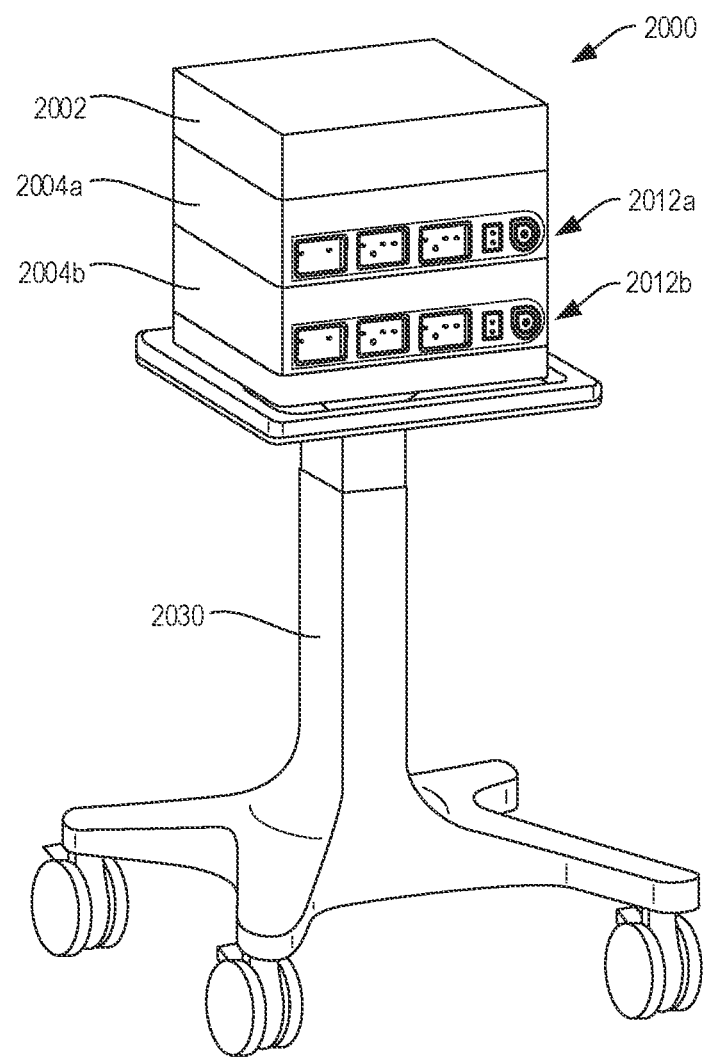
FIG. 26B is a third illustrative modular energy system configuration that is similar to the second configuration shown in FIG. 25A, except that the header module lacks a display screen, in accordance with at least one aspect of the present disclosure.

FIG. 26A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 26B illustrates a third illustrative configuration that is similar to the second configuration, except that the header module 2002 lacks a display screen 2006. This configuration can be suitable for robotic surgical applications or mobile display applications, as noted above.

Figure 27:
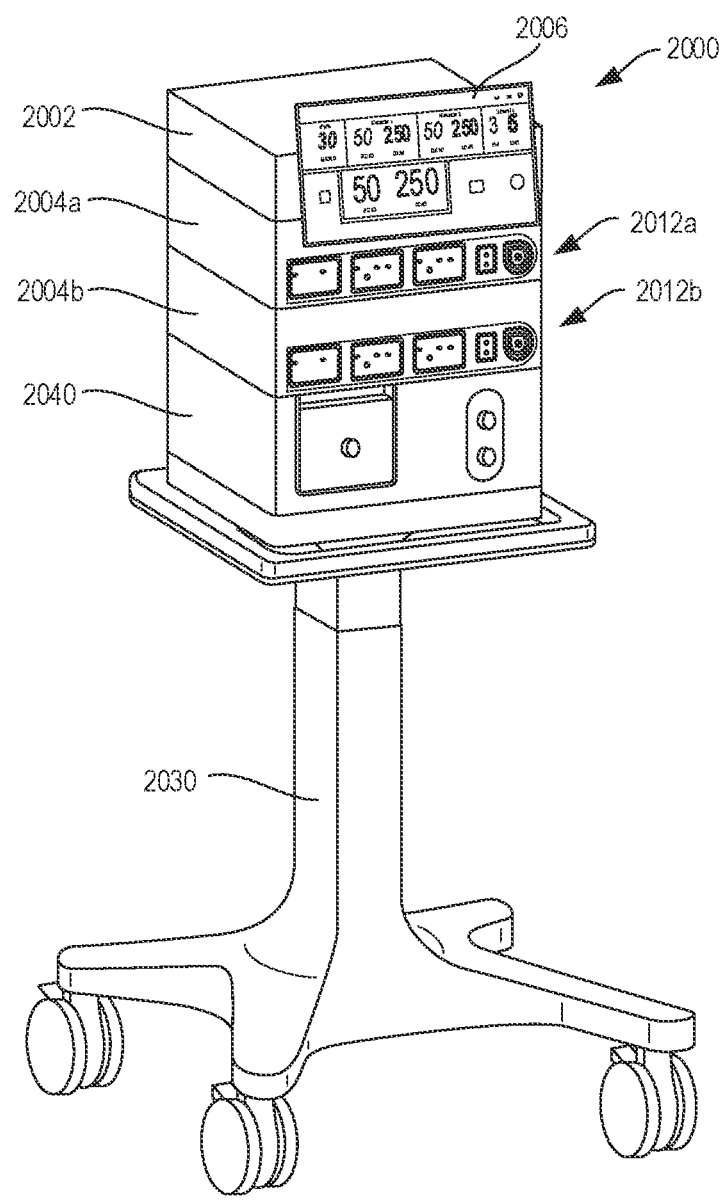
FIG. 27 is a fourth illustrative modular energy system configuration including a header module, a display screen, an energy module, ae expanded energy module, and a technology module connected together and mounted to a cart, in accordance with at least one aspect of the present disclosure.

FIG. 27 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 28:
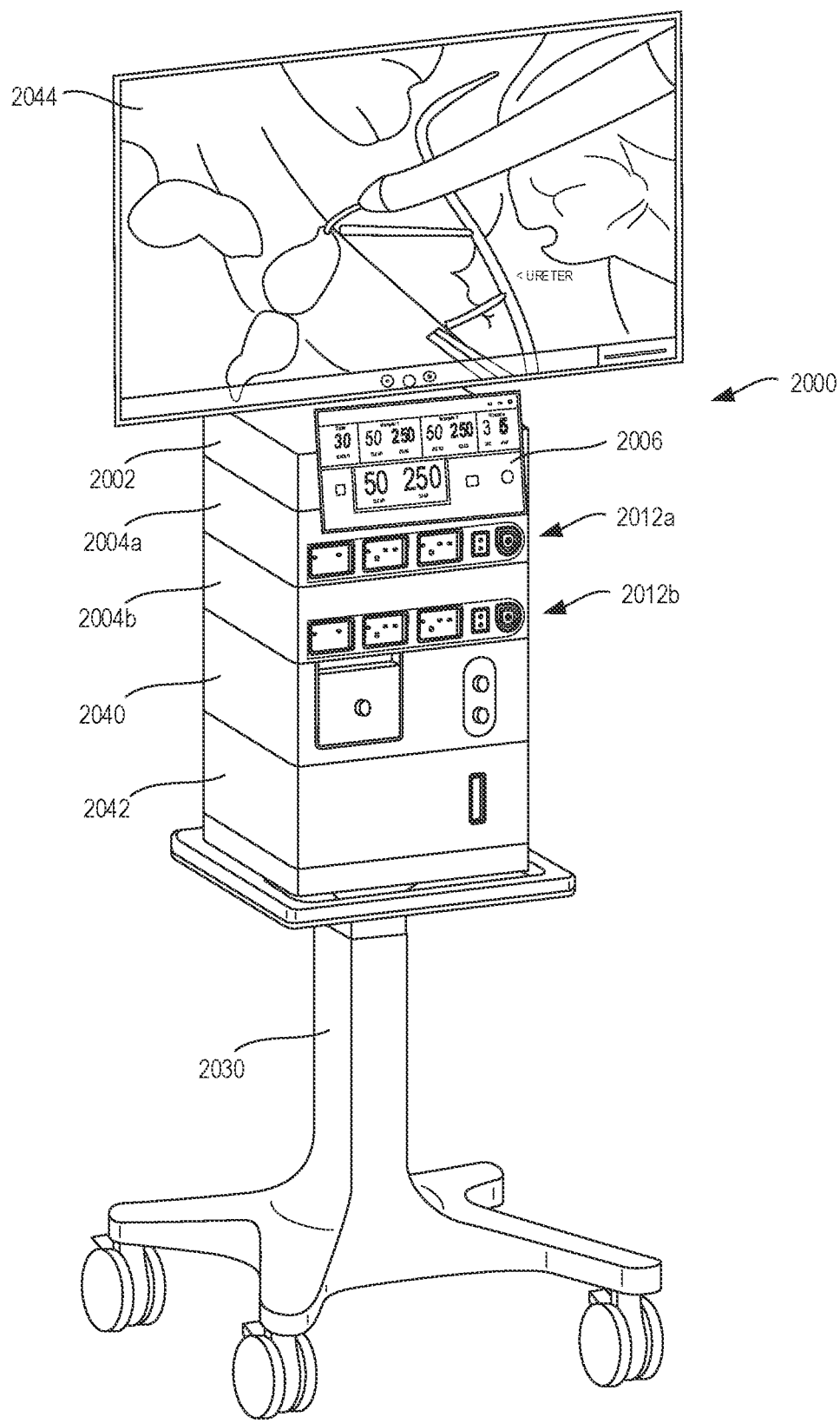
FIG. 28 is a fifth illustrative modular energy system configuration including a header module, a display screen, an energy module, an expanded energy module, a technology module, and a visualization module connected together and mounted to a cart, in accordance with at least one aspect of the present disclosure.

FIG. 28 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 25A-29 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 29. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 30:
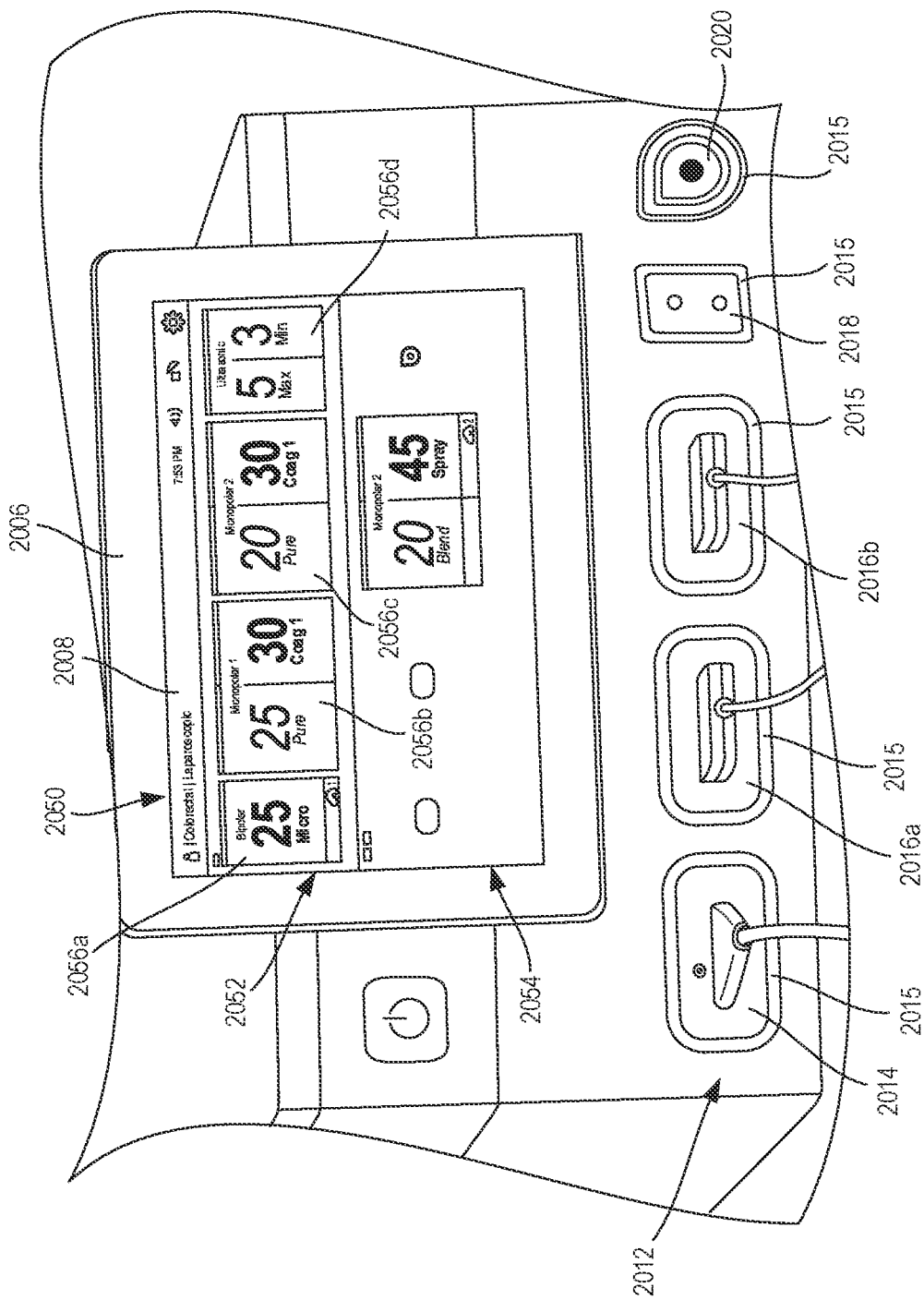
FIG. 30 is a perspective view of a header module of a modular energy system including a user interface, in accordance with at least one aspect of the present disclosure.

Referring now to FIG. 30, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 30, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056*a* corresponding to the bipolar port 2014, a second widget 2056*b* corresponding to the first monopolar port 2016*a*, a third widget 2056*c* corresponding to the second monopolar port 2016*b*, and a fourth widget 2056*d* corresponding to the combination energy port 2020. Each of these widgets 2056*a-d* provides data related to its corresponding port of the port assembly 2012 and controls for controlling the modes and other features of the energy modality delivered by the energy module 2004 through the respective port of the port assembly 2012. For example, the widgets 2056*a-d* can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the activation of each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicatively coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 31:
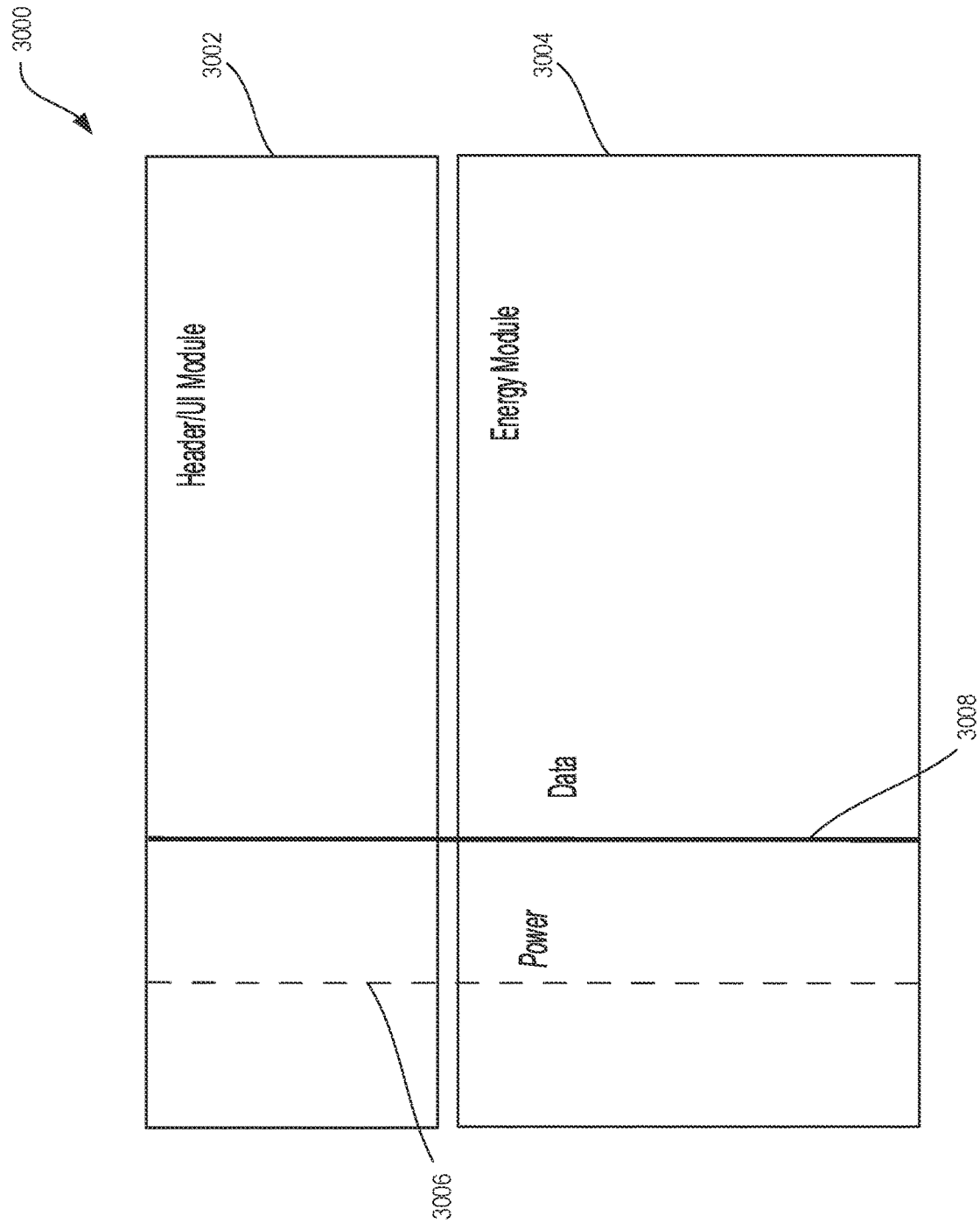
FIG. 31 is a block diagram of a stand-alone hub configuration of a modular energy system, in accordance with at least one aspect of the present disclosure.
Figure 32:
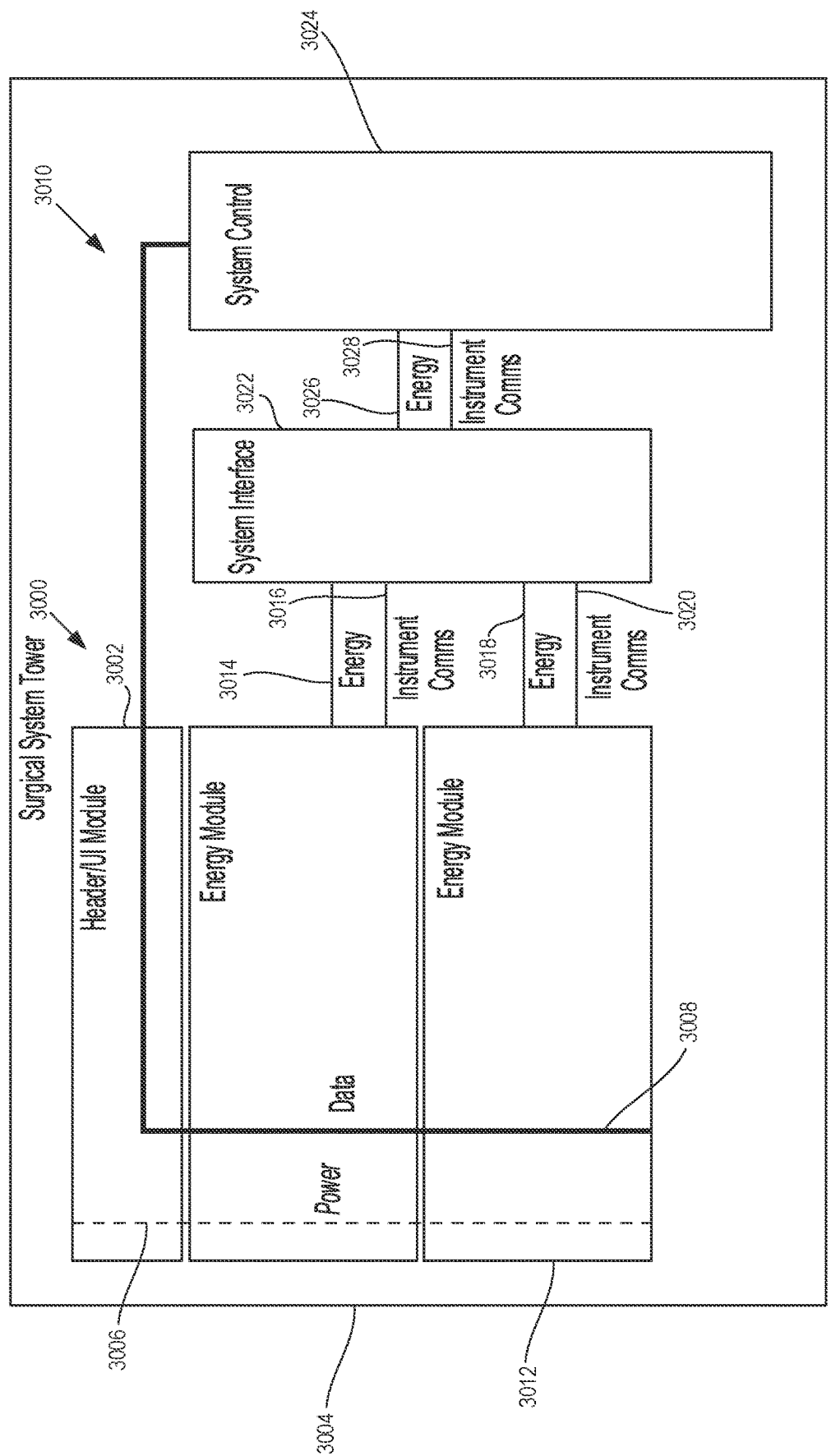
FIG. 32 is a block diagram of a hub configuration of a modular energy system integrated with a surgical control system, in accordance with at least one aspect of the present disclosure.

FIG. 31 is a block diagram of a stand-alone hub configuration of a modular energy system 3000, in accordance with at least one aspect of the present disclosure and FIG. 32 is a block diagram of a hub configuration of a modular energy system 3000 integrated with a surgical control system 3010, in accordance with at least one aspect of the present disclosure. As depicted in FIGS. 31 and 32, the modular energy system 3000 can be either utilized as stand-alone units or integrated with a surgical control system 3010 that controls and/or receives data from one or more surgical hub units. In the examples illustrated in FIGS. 31 and 32, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 31, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 32, a surgical hub configuration includes a modular energy system 3000 integrated with a control system 3010 and an interface system 3022 for managing, among other things, data and power transmission to and/or from the modular energy system 3000. The modular energy system depicted in FIG. 32 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

As described in more detail hereinbelow, the energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

Figure 33:
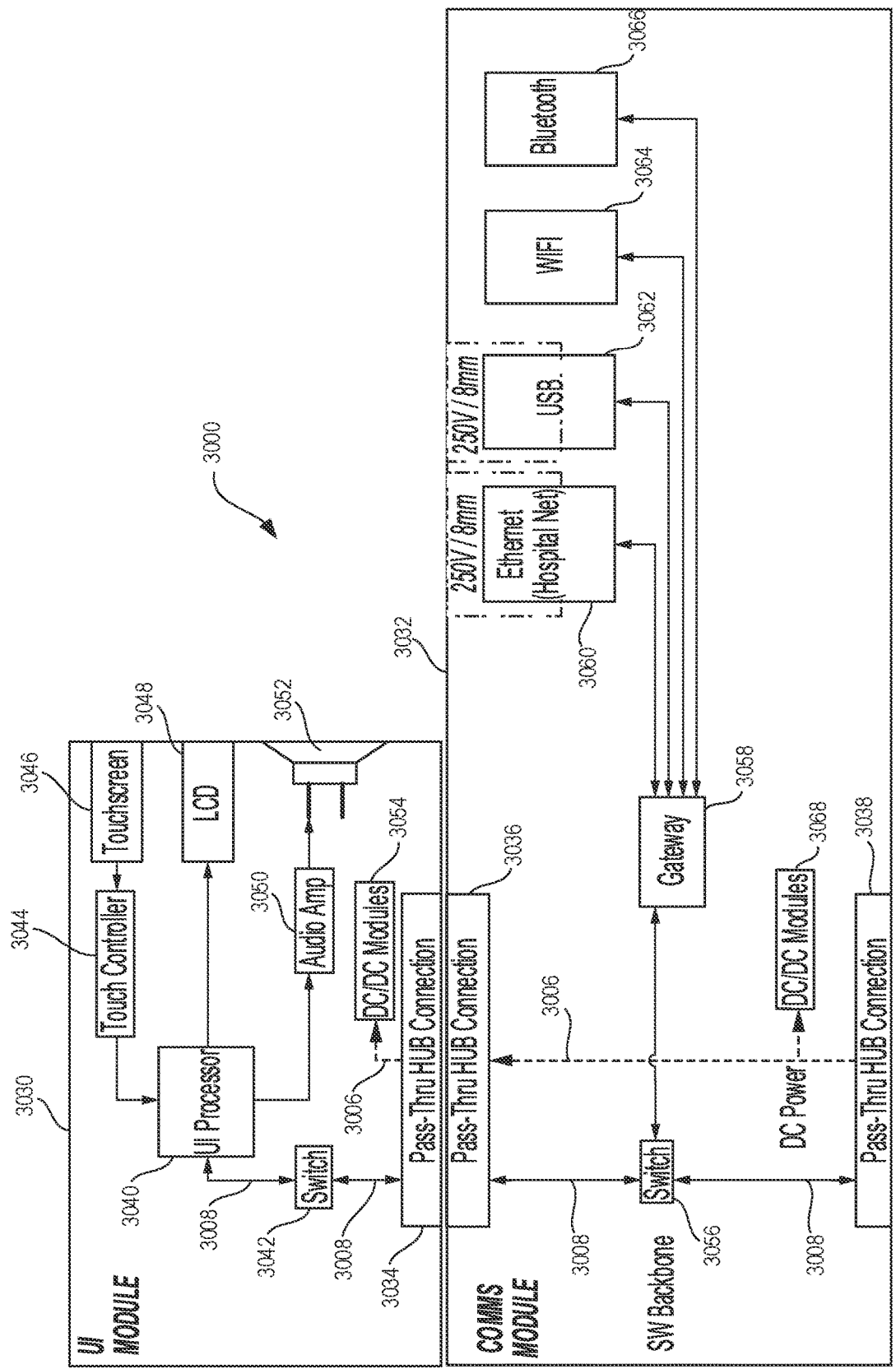
FIG. 33 is a block diagram of a user interface module coupled to a communications module of a modular energy system, in accordance with at least one aspect of the present disclosure.
Figure 34:
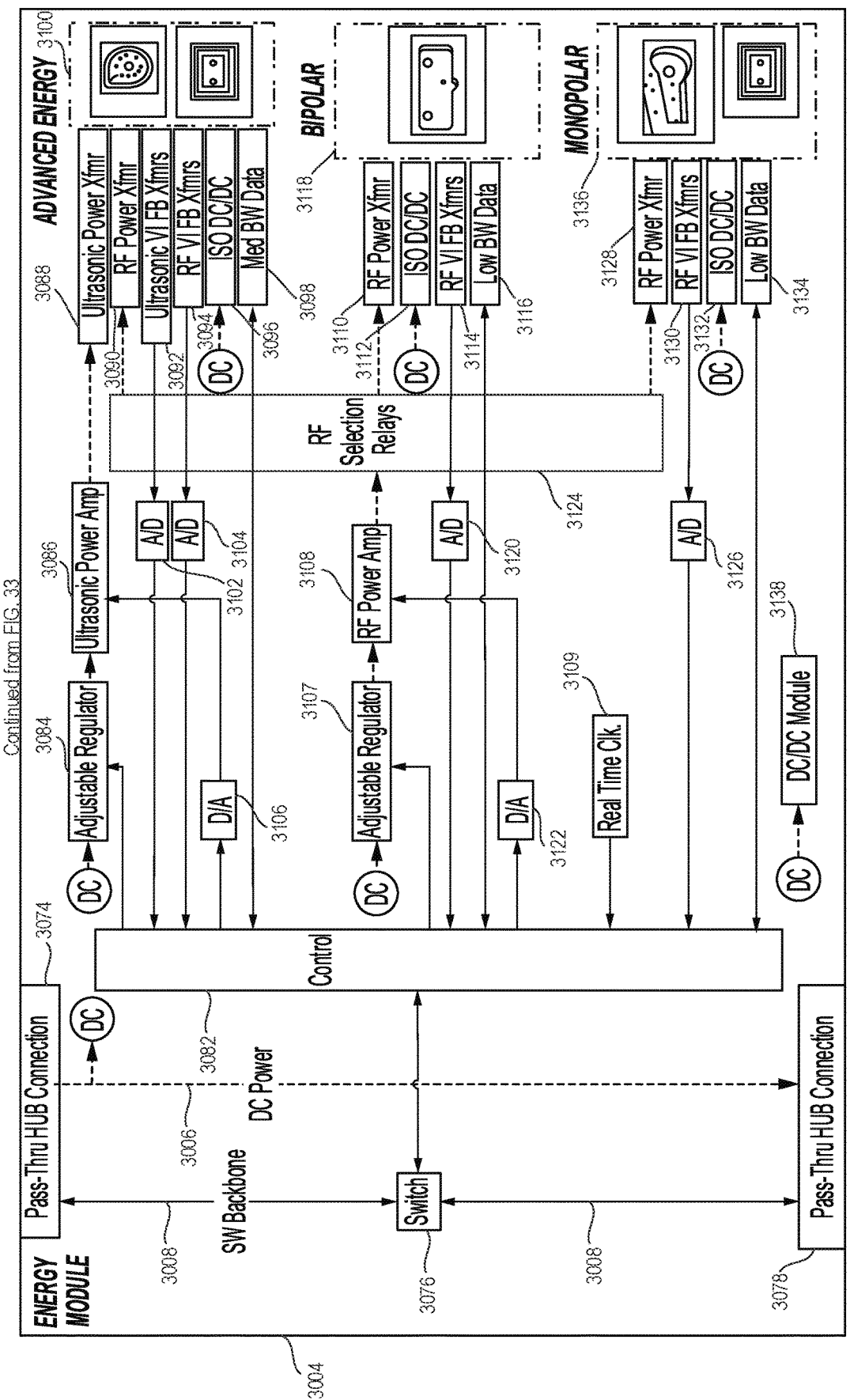
FIG. 34 is a block diagram of an energy module of a modular energy system, in accordance with at least one aspect of the present disclosure.
Figure 35A:
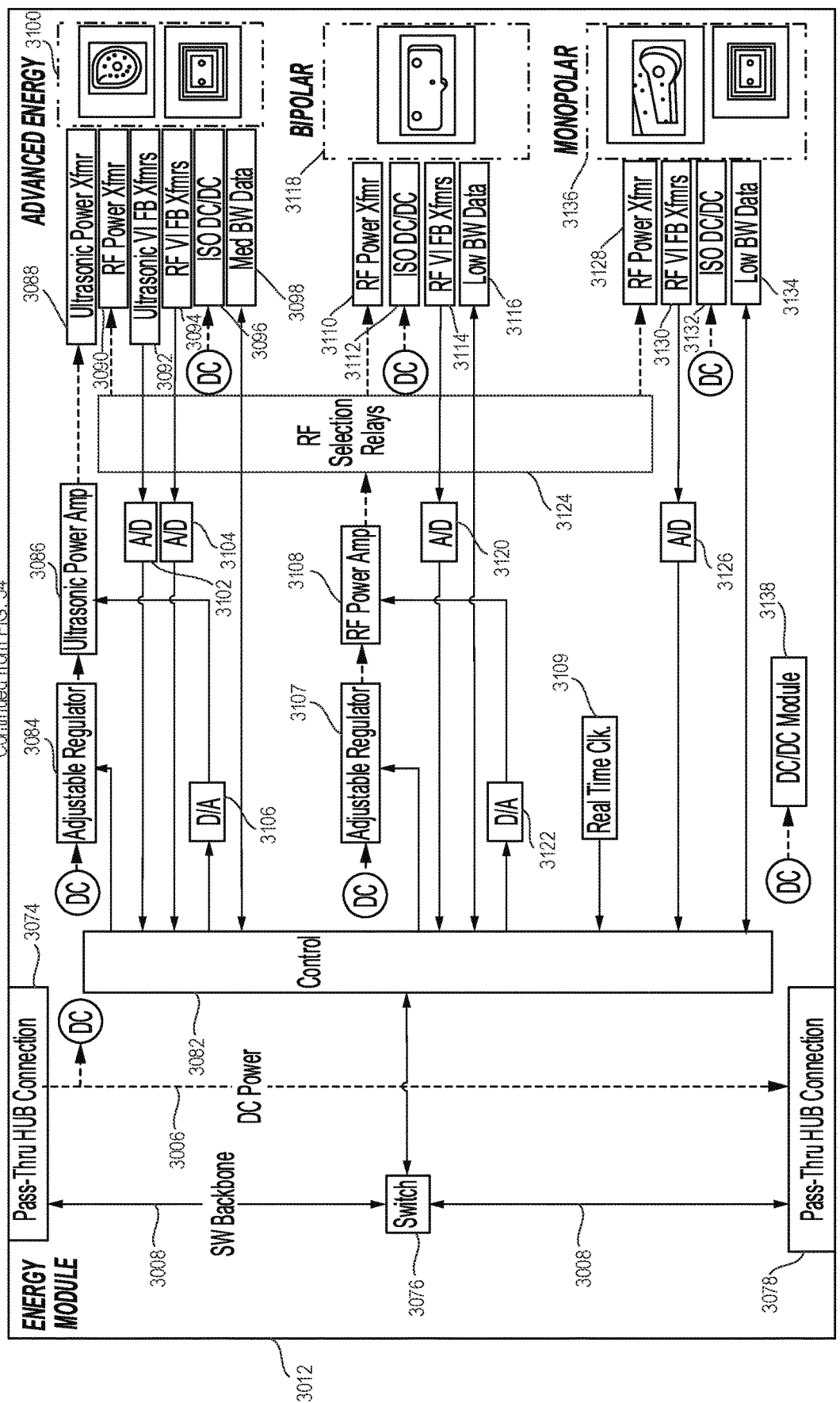
FIGS. 35A and 35B illustrate a block diagram of an energy module coupled to a header module of a modular energy system, in accordance with at least one aspect of the present disclosure.
Figure 35B:
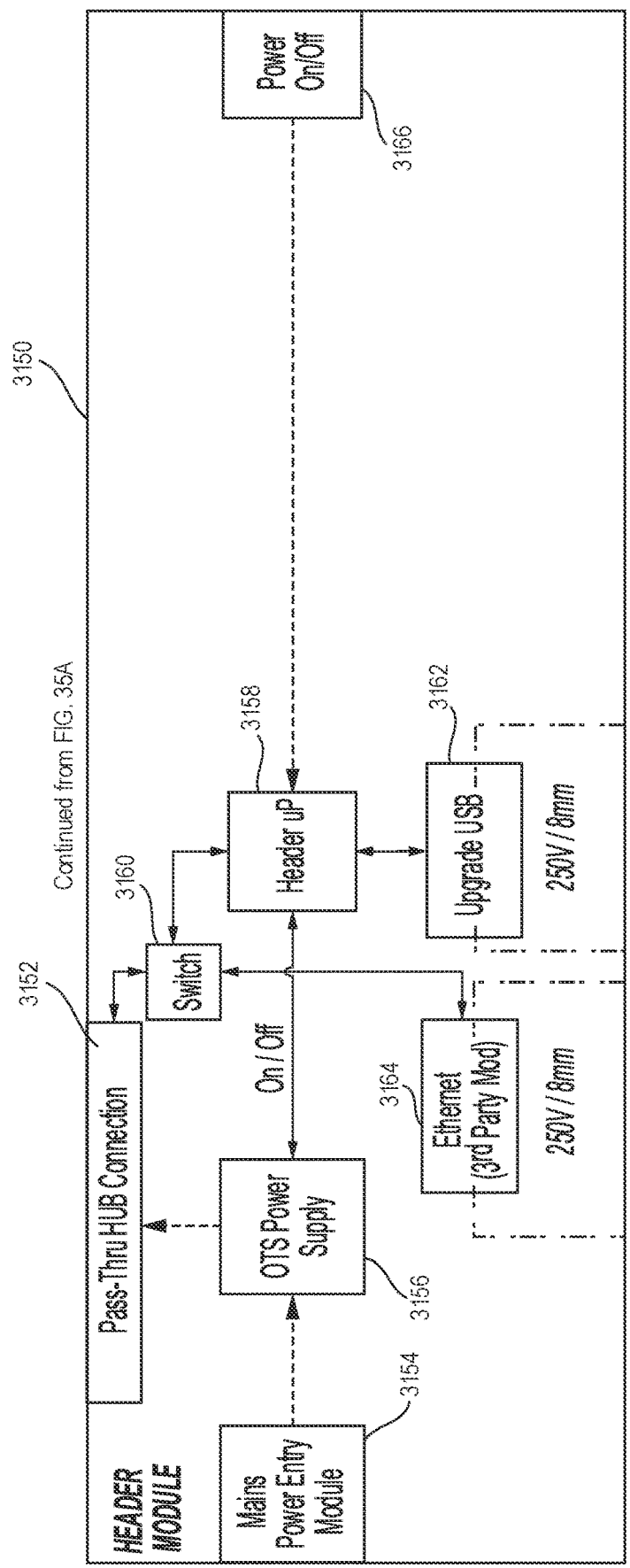

FIGS. 33-35 are block diagrams of various modular energy systems connected together to form a hub, in accordance with at least one aspect of the present disclosure. FIGS. 33-35 depict various diagrams (e.g., circuit or control diagrams) of hub modules. The modular energy system 3000 includes multiple energy modules 3004 (FIG. 34), 3012 (FIG. 35), a header module 3150 (FIG. 35), a UI module 3030 (FIG. 33), and a communications module 3032 (FIG. 33), in accordance with at least one aspect of the present disclosure. The UI module 3030 includes a touch screen 3046 displaying various relevant information and various user controls for controlling one or more parameters of the modular energy system 3000. The UI module 3030 is attached to the top header module 3150, but is separately housed so that it can be manipulated independently of the header module 3150. For example, the UI module 3030 can be picked up by a user and/or reattached to the header module 3150. Additionally, or alternatively, the UI module 3030 can be slightly moved relative to the header module 3150 to adjust its position and/or orientation. For example, the UI module 3030 can be tilted and/or rotated relative to the header module 3150.

In some aspects, the various hub modules can include light piping around the physical ports to communicate instrument status and also connect on-screen elements to corresponding instruments. Light piping is one example of an illumination technique that may be employed to alert a user to a status of a surgical instrument attached/connected to a physical port. In one aspect, illuminating a physical port with a particular light directs a user to connect a surgical instrument to the physical port. In another example, illuminating a physical port with a particular light alerts a user to an error related an existing connection with a surgical instrument.

Turning to FIG. 33, there is shown a block diagram of a user interface (UI) module 3030 coupled to a communications module 3032 via a pass-through hub connector 3034, in accordance with at least one aspect of the present disclosure. The UI module 3030 is provided as a separate component from a header module 3150 (shown in FIG. 35) and may be communicatively coupled to the header module 3150 via a communications module 3032, for example. In one aspect, the UI module 3030 can include a UI processor 3040 that is configured to represent declarative visualizations and behaviors received from other connected modules, as well as perform other centralized UI functionality, such as system configuration (e.g., language selection, module associations, etc.). The UI processor 3040 can be, for example, a processor or system on module (SOM) running a framework such as Qt, .NET WPF, Web server, or similar.

In the illustrated example, the UI module 3030 includes a touchscreen 3046, a liquid crystal display 3048 (LCD), and audio output 3052 (e.g., speaker, buzzer). The UI processor 3040 is configured to receive touchscreen inputs from a touch controller 3044 coupled between the touch screen 3046 and the UI processor 3040. The UI processor 3040 is configured to output visual information to the LCD display 3048 and to output audio information to the audio output 3052 via an audio amplifier 3050. The UI processor 3040 is configured to interface to the communications module 3032 via a switch 3042 coupled to the pass-through hub connector 3034 to receive, process, and forward data from the source device to the destination device and control data communication therebetween. DC power is supplied to the UI module 3030 via DC/DC converter modules 3054. The DC power is passed through the pass-through hub connector 3034 to the communications module 3032 through the power bus 3006. Data is passed through the pass-through hub connector 3034 to the communications module 3032 through the data bus 3008. Switches 3042, 3056 receive, process, and forward data from the source device to the destination device.

Continuing with FIG. 33, the communications module 3032, as well as various surgical hubs and/or surgical systems can include a gateway 3058 that is configured to shuttle select traffic (i.e., data) between two disparate networks (e.g., an internal network and/or a hospital network) that are running different protocols. The communications module 3032 includes a first pass-through hub connector 3036 to couple the communications module 3032 to other modules. In the illustrated example, the communications module 3032 is coupled to the UI module 3030. The communications module 3032 is configured to couple to other modules (e.g., energy modules) via a second pass-through hub connector 3038 to couple the communications module 3032 to other modules via a switch 3056 disposed between the first and second pass-through hub connectors 3036, 3038 to receive, process, and forward data from the source device to the destination device and control data communication therebetween. The switch 3056 also is coupled to a gateway 3058 to communicate information between external communications ports and the UI module 3030 and other connected modules. The gateway 3058 may be coupled to various communications modules such as, for example, an Ethernet module 3060 to communicate to a hospital or other local network, a universal serial bus (USB) module 3062, a WFi module 3064, and a Bluetooth module 3066, among others. The communications modules may be physical boards located within the communications module 3032 or may be a port to couple to remote communications boards.

Figure 36A:
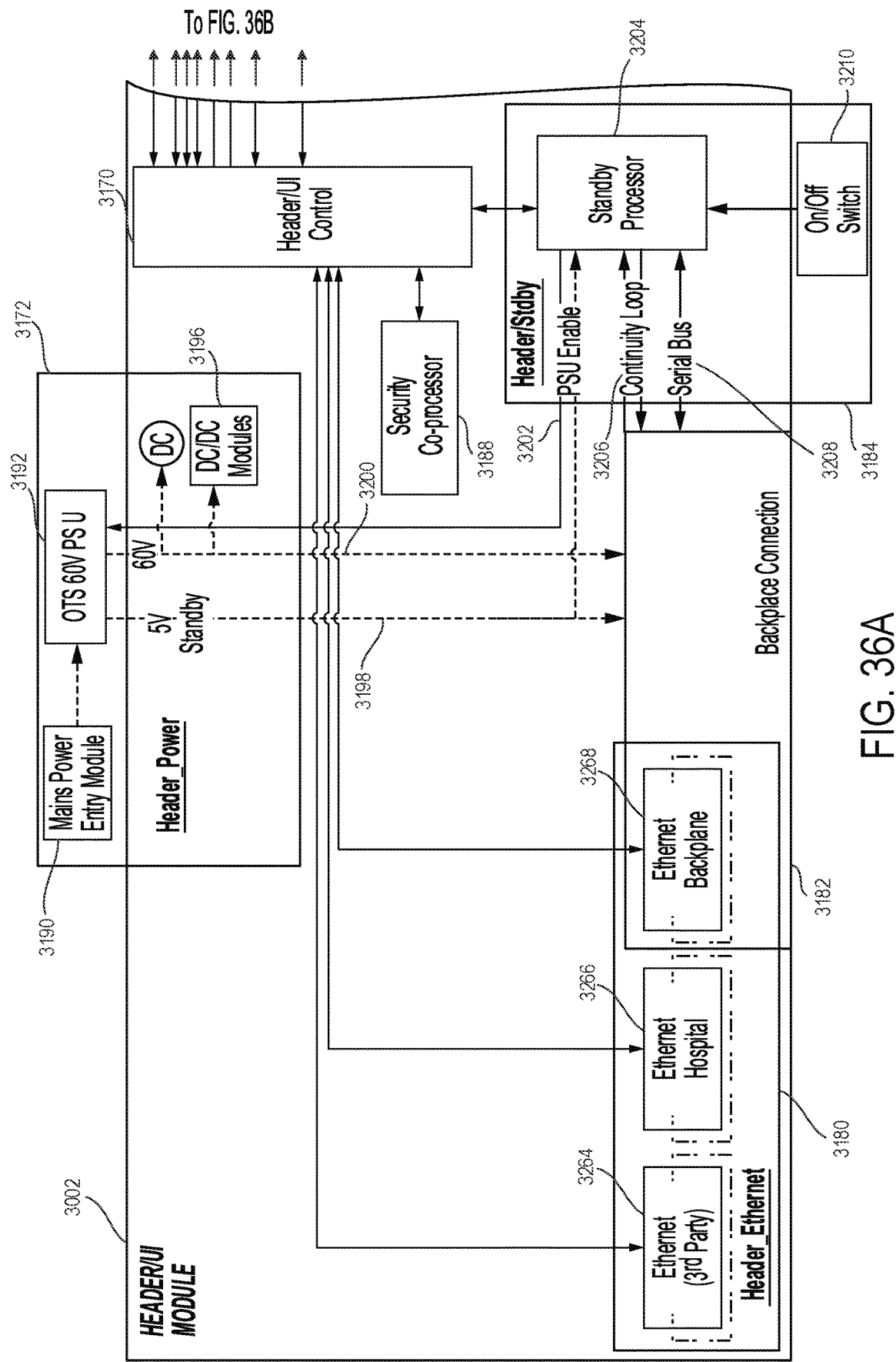
FIGS. 36A and 36B illustrate a block diagram of a header/user interface (UI) module of a modular energy system for a hub, such as the header module depicted in FIG. 33, in accordance with at least one aspect of the present disclosure.
Figure 36B:
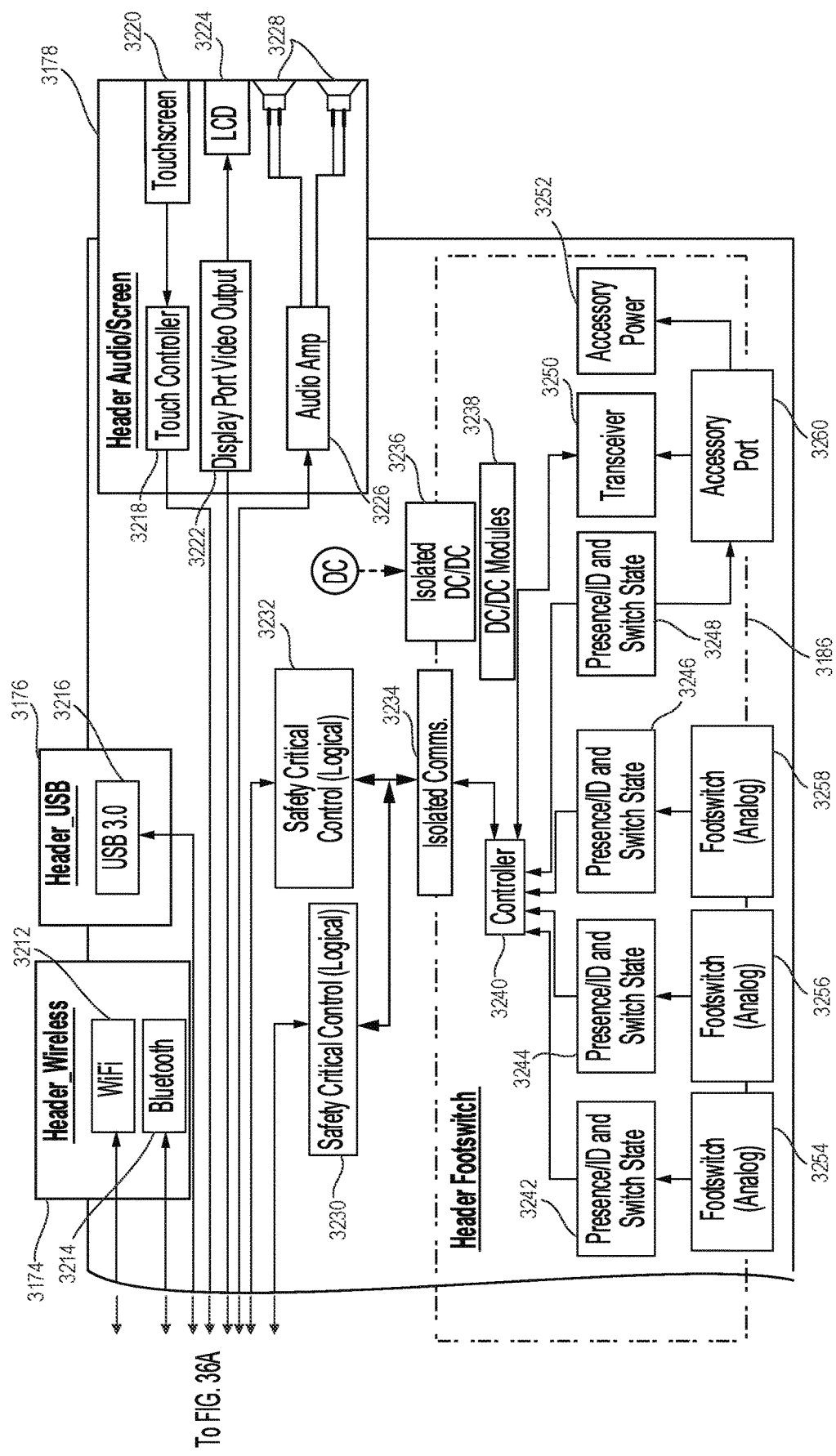

In some aspects, all of the modules (i.e., detachable hardware) are controlled by a single UI module 3030 that is disposed on or integral to a header module. FIG. 35 shows a stand alone header module 3150 to which the UI module 3030 can be attached. FIGS. 31, 32, and 36 show an integrated header/UI Module 3002. Returning now to FIG. 33, in various aspects, by consolidating all of the modules into a single, responsive UI module 3002, the system provides a simpler way to control and monitor multiple pieces of equipment at once. This approach drastically reduces footprint and complexity in an operating room (OR).

Turning to FIG. 34, there is shown a block diagram of an energy module 3004, in accordance with at least one aspect of the present disclosure. The communications module 3032 (FIG. 33) is coupled to the energy module 3004 via the second pass-through hub connector 3038 of the communications module 3032 and a first pass-through hub connector 3074 of the energy module 3004. The energy module 3004 may be coupled to other modules, such as a second energy module 3012 shown in FIG. 35, via a second pass-through hub connector 3078. Turning back to FIG. 34, a switch 3076 disposed between the first and second pass-through hub connectors 3074, 3078 receives, processes, and forwards data from the source device to the destination device and controls data communication therebetween. Data is received and transmitted through the data bus 3008. The energy module 3032 includes a controller 3082 to control various communications and processing functions of the energy module 3004.

DC power is received and transmitted by the energy module 3004 through the power bus 3006. The power bus 3006 is coupled to DC/DC converter modules 3138 to supply power to adjustable regulators 3084, 3107 and isolated DC/DC converter ports 3096, 3112, 3132.

In one aspect, the energy module 3004 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of an advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog-to-digital converter 3102 (A/D). Also coupled to the controller 3082 through the advanced energy receptacle 3100 is the isolated DC/DC converter port 3096, which receives DC power from the power bus 3006, and a medium bandwidth data port 3098.

In one aspect, the energy module 3004 can include a wideband RF power amplifier 3108, which in one aspect may be a linear class H amplifier that is capable of generating arbitrary waveforms and drive RF loads at a range of output frequencies. The wideband RF power amplifier 3108 is fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the wideband RF amplifier 3086 via a DAC 3122. The output of the wideband RF power amplifier 3108 can be fed through RF selection relays 3124. The RF selection relays 3124 are configured to receive and selectively transmit the output signal of the wideband RF power amplifier 3108 to various other components of the energy module 3004. In one aspect, the output signal of the wideband RF power amplifier 3108 can be fed through RF selection relays 3124 to an RF power transformer 3110, which is coupled to an RF output portion of a bipolar RF energy receptacle 3118. Bipolar RF voltage (V) and current (I) feedback (FB) signals, which may be employed to compute RF impedance, are fed back to the controller 3082 via an RF VI FB transformer 3114 through an input portion of the bipolar RF energy receptacle 3118. The RF voltage and current feedback signals are routed back to the controller 3082 through an A/D 3120. Also coupled to the controller 3082 through the bipolar RF energy receptacle 3118 is the isolated DC/DC converter port 3112, which receives DC power from the power bus 3006, and a low bandwidth data port 3116.

As described above, in one aspect, the energy module 3004 can include RF selection relays 3124 driven by the controller 3082 (e.g., FPGA) at rated coil current for actuation and can also be set to a lower hold-current via pulse-width modulation (PWM) to limit steady-state power dissipation. Switching of the RF selection relays 3124 is achieved with force guided (safety) relays and the status of the contact state is sensed by the controller 3082 as a mitigation for any single fault conditions. In one aspect, the RF selection relays 3124 are configured to be in a first state, where an output RF signal received from an RF source, such as the wideband RF power amplifier 3108, is transmitted to a first component of the energy module 3004, such as the RF power transformer 3110 of the bipolar energy receptacle 3118. In a second aspect, the RF selection relays 3124 are configured to be in a second state, where an output RF signal received from an RF source, such as the wideband RF power amplifier 3108, is transmitted to a second component, such as an RF power transformer 3128 of a monopolar energy receptacle 3136, described in more detail below. In a general aspect, the RF selection relays 3124 are configured to be driven by the controller 3082 to switch between a plurality of states, such as the first state and the second state, to transmit the output RF signal received from the RF power amplifier 3108 between different energy receptacles of the energy module 3004.

As described above, the output of the wideband RF power amplifier 3108 can also fed through the RF selection relays 3124 to the wideband RF power transformer 3128 of the RF monopolar receptacle 3136. Monopolar RF voltage (V) and current (I) feedback (FB) signals, which may be employed to compute RF impedance, are fed back to the controller 3082 via an RF VI FB transformer 3130 through an input portion of the monopolar RF energy receptacle 3136. The RF voltage and current feedback signals are routed back to the controller 3082 through an A/D 3126. Also coupled to the controller 3082 through the monopolar RF energy receptacle 3136 is the isolated DC/DC converter port 3132, which receives DC power from the power bus 3006, and a low bandwidth data port 3134.

The output of the wideband RF power amplifier 3108 can also fed through the RF selection relays 3124 to the wideband RF power transformer 3090 of the advanced energy receptacle 3100. RF voltage (V) and current (I) feedback (FB) signals, which may be employed to compute RF impedance, are fed back to the controller 3082 via an RF VI FB transformer 3094 through an input portion of the advanced energy receptacle 3100. The RF voltage and current feedback signals are routed back to the controller 3082 through an A/D 3104.

FIG. 35 is a block diagram of a second energy module 3012 coupled to a header module 3150, in accordance with at least one aspect of the present disclosure. The first energy module 3004 shown in FIG. 34 is coupled to the second energy module 3012 shown in FIG. 35 by coupling the second pass-through hub connector 3078 of the first energy module 3004 to a first pass-through hub connector 3074 of the second energy module 3012. In one aspect, the second energy module 3012 can a similar energy module to the first energy module 3004, as is illustrated in FIG. 35. In another aspect, the second energy module 2012 can be a different energy module compared to the first energy module, such as an energy module illustrated in FIG. 37, described in more detail. The addition of the second energy module 3012 to the first energy module 3004 adds functionality to the modular energy system 3000.

The second energy module 3012 is coupled to the header module 3150 by connecting the pass-through hub connector 3078 to the pass-through hub connector 3152 of the header module 3150. In one aspect, the header module 3150 can include a header processor 3158 that is configured to manage a power button function 3166, software upgrades through the upgrade USB module 3162, system time management, and gateway to external networks (i.e., hospital or the cloud) via an Ethernet module 3164 that may be running different protocols. Data is received by the header module 3150 through the pass-through hub connector 3152. The header processor 3158 also is coupled to a switch 3160 to receive, process, and forward data from the source device to the destination device and control data communication therebetween. The header processor 3158 also is coupled to an OTS power supply 3156 coupled to a mains power entry module 3154.

FIG. 36 is a block diagram of a header/user interface (UI) module 3002 for a hub, such as the header module depicted in FIG. 33, in accordance with at least one aspect of the present disclosure. The header/UI module 3002 includes a header power module 3172, a header wireless module 3174, a header USB module 3176, a header audio/screen module 3178, a header network module 3180 (e.g., Ethernet), a backplane connector 3182, a header standby processor module 3184, and a header footswitch module 3186. These functional modules interact to provide the header/UI 3002 functionality. A header/UI controller 3170 controls each of the functional modules and the communication therebetween including safety critical control logic modules 3230, 3232 coupled between the header/UI controller 3170 and an isolated communications module 3234 coupled to the header footswitch module 3186. A security co-processor 3188 is coupled to the header/UI controller 3170.

The header power module 3172 includes a mains power entry module 3190 coupled to an OTS power supply unit 3192 (PSU). Low voltage direct current (e.g., 5V) standby power is supplied to the header/UI module 3002 and other modules through a low voltage power bus 3198 from the OTS PSU 3192. High voltage direct current (e.g., 60V) is supplied to the header/UI module 3002 through a high voltage bus 3200 from the OTS PSU 3192. The high voltage DC supplies DC/DC converter modules 3196 as well as isolated DC/DC converter modules 3236. A standby processor 3204 of the header/standby module 3184 provides a PSU/enable signal 3202 to the OTS PSU 3192.

The header wireless module 3174 includes a WFi module 3212 and a Bluetooth module 3214. Both the WiFi module 3212 and the Bluetooth module 3214 are coupled to the header/UI controller 3170. The Bluetooth module 3214 is used to connect devices without using cables and the Wi-Fi module 3212 provides high-speed access to networks such as the Internet and can be employed to create a wireless network that can link multiple devices such as, for examples, multiple energy modules or other modules and surgical instruments, among other devices located in the operating room. Bluetooth is a wireless technology standard that is used to exchange data over short distances, such as, less than 30 feet.

The header USB module 3176 includes a USB port 3216 coupled to the header/UI controller 3170. The USB module 3176 provides a standard cable connection interface for modules and other electronics devices over short-distance digital data communications. The USB module 3176 allows modules comprising USB devices to be connected to each other with and transfer digital data over USB cables.

The header audio/screen module 3178 includes a touchscreen 3220 coupled to a touch controller 3218. The touch controller 3218 is coupled to the header/UI controller 3170 to read inputs from the touchscreen 3220. The header/UI controller 3170 drives an LCD display 3224 through a display/port video output signal 3222. The header/UI controller 3170 is coupled to an audio amplifier 3226 to drive one or more speakers 3228.

In one aspect, the header/UI module 3002 provides a touchscreen 3220 user interface configured to control modules connected to one control or header module 3002 in a modular energy system 3000. The touchscreen 3220 can be used to maintain a single point of access for the user to adjust all modules connected within the modular energy system 3000. Additional hardware modules (e.g., a smoke evacuation module) can appear at the bottom of the user interface LCD display 3224 when they become connected to the header/UI module 3002, and can disappear from the user interface LCD display 3224 when they are disconnected from the header/UI module 3002.

Further, the user touchscreen 3220 can provide access to the settings of modules attached to the modular energy system 3000. Further, the user interface LCD display 3224 arrangement can be configured to change according to the number and types of modules that are connected to the header/UI module 3002. For example, a first user interface can be displayed on the LCD display 3224 for a first application where one energy module and one smoke evacuation module are connected to the header/UI module 3002, and a second user interface can be displayed on the LCD display 3224 for a second application where two energy modules are connected to the header/UI module 3002. Further, the user interface can alter its display on the LCD display 3224 as modules are connected and disconnected from the modular energy system 3000.

In one aspect, the header/UI module 3002 provides a user interface LCD display 3224 configured to display on the LCD display coloring corresponds to the port lighting. In one aspect, the coloring of the instrument panel and the LED light around its corresponding port will be the same or otherwise correspond with each other. Each color can, for example, convey a unique meaning. This way, the user will be able to quickly assess which instrument the indication is referring to and the nature of the indication. Further, indications regarding an instrument can be represented by the changing of color of the LED light lined around its corresponding port and the coloring of its module. Still further, the message on screen and hardware/software port alignment can also serve to convey that an action must be taken on the hardware, not on the interface. In various aspects, all other instruments can be used while alerts are occurring on other instruments. This allows the user to be able to quickly assess which instrument the indication is referring to and the nature of the indication.

In one aspect, the header/UI module 3002 provides a user interface screen configured to display on the LCD display 3224 to present procedure options to a user. In one aspect, the user interface can be configured to present the user with a series of options (which can be arranged, e.g., from broad to specific). After each selection is made, the modular energy system 3000 presents the next level until all selections are complete. These settings could be managed locally and transferred via a secondary means (such as a USB thumb drive). Alternatively, the settings could be managed via a portal and automatically distributed to all connected systems in the hospital.

The procedure options can include, for example, a list of factory preset options categorized by specialty, procedure, and type of procedure. Upon completing a user selection, the header module can be configured to set any connected instruments to factory-preset settings for that specific procedure. The procedure options can also include, for example, a list of surgeons, then subsequently, the specialty, procedure, and type. Once a user completes a selection, the system may suggest the surgeon's preferred instruments and set those instrument's settings according to the surgeon's preference (i.e., a profile associated with each surgeon storing the surgeon's preferences).

In one aspect, the header/UI module 3002 provides a user interface screen configured to display on the LCD display 3224 critical instrument settings. In one aspect, each instrument panel displayed on the LCD display 3224 of the user interface corresponds, in placement and content, to the instruments plugged into the modular energy system 3000. When a user taps on a panel, it can expand to reveal additional settings and options for that specific instrument and the rest of the screen can, for example, darken or otherwise be de-emphasized.

In one aspect, the header/UI module 3002 provides an instrument settings panel of the user interface configured to comprise/display controls that are unique to an instrument and allow the user to increase or decrease the intensity of its output, toggle certain functions, pair it with system accessories like a footswitch connected to header footswitch module 3186, access advanced instrument settings, and find additional information about the instrument. In one aspect, the user can tap/select an "Advanced Settings" control to expand the advanced settings drawer displayed on the user interface LCD display 3224. In one aspect, the user can then tap/select an icon at the top right-hand corner of the instrument settings panel or tap anywhere outside of the panel and the panel will scale back down to its original state. In these aspects, the user interface is configured to display on the LCD display 3224 only the most critical instrument settings, such as power level and power mode, on the ready/home screen for each instrument panel. This is to maximize the size and readability of the system from a distance. In some aspects, the panels and the settings within can be scaled proportionally to the number of instruments connected to the system to further improve readability. As more instruments are connected, the panels scale to accommodate a greater amount of information.

The header network module 3180 includes a plurality of network interfaces 3264, 3266, 3268 (e.g., Ethernet) to network the header/UI module 3002 to other modules of the modular energy system 3000. In the illustrated example, one network interface 3264 may be a 3rd party network interface, another network interface 3266 may be a hospital network interface, and yet another network interface 3268 may be located on the backplane network interface connector 3182.

The header standby processor module 3184 includes a standby processor 3204 coupled to an On/Off switch 3210. The standby processor 3204 conducts an electrical continuity test by checking to see if electrical current flows in a continuity loop 3206. The continuity test is performed by placing a small voltage across the continuity loop 3206. A serial bus 3208 couples the standby processor 3204 to the backplane connector 3182.

The header footswitch module 3186 includes a controller 3240 coupled to a plurality of analog footswitch ports 3254, 3256, 3258 through a plurality of corresponding presence/ID and switch state modules 3242, 3244, 3246, respectively.

The controller 3240 also is coupled to an accessory port 3260 via a presence/ID and switch state module 3248 and a transceiver module 3250. The accessory port 3260 is powered by an accessory power module 3252. The controller 3240 is coupled to header/UI controller 3170 via an isolated communication module 3234 and first and second safety critical control modules 3230, 3232. The header footswitch module 3186 also includes DC/DC converter modules 3238.

In one aspect, the header/UI module 3002 provides a user interface screen configured to display on the LCD display 3224 for controlling a footswitch connected to any one of the analog footswitch ports 3254, 3256, 3258. In some aspects, when the user plugs in a non hand-activated instrument into any one of the analog footswitch ports 3254, 3256, 3258, the instrument panel appears with a warning icon next to the footswitch icon. The instrument settings can be, for example, greyed out, as the instrument cannot be activated without a footswitch.

When the user plugs in a footswitch into any one of the analog footswitch ports 3254, 3256, 3258, a pop-up appears indicating that a footswitch has been assigned to that instrument. The footswitch icon indicates that a footswitch has been plugged in and assigned to the instrument. The user can then tap/select on that icon to assign, reassign, unassign, or otherwise change the settings associated with that footswitch. In these aspects, the system is configured to automatically assign footswitches to non hand-activated instruments using logic, which can further assign single or double-pedal footswitches to the appropriate instrument. If the user wants to assign/reassign footswitches manually there are two flows that can be utilized.

In one aspect, the header/UI module 3002 provides a global footswitch button. Once the user taps on the global footswitch icon (located in the upper right of the user interface LCD display 3224), the footswitch assignment overlay appears and the contents in the instrument modules dim. A (e.g., photo-realistic) representation of each attached footswitch (dual or single-pedal) appears on the bottom if unassigned to an instrument or on the corresponding instrument panel. Accordingly, the user can drag and drop these illustrations into, and out of, the boxed icons in the footswitch assignment overlay to assign, unassign, and reassign footswitches to their respective instruments.

In one aspect, the header/UI module 3002 provides a user interface screen displayed on the LCD display 3224 indicating footswitch auto-assignment, in accordance with at least one aspect of the present disclosure. As discussed above, the modular energy system 3000 can be configured to auto-assign a footswitch to an instrument that does not have hand activation. In some aspects, the header/UI module 3002 can be configured to correlate the colors displayed on the user interface LCD display 3224 to the lights on the modules themselves as means of tracking physical ports with user interface elements.

In one aspect, the header/UI module 3002 may be configured to depict various applications of the user interface with differing number of modules connected to the modular energy system 3000. In various aspects, the overall layout or proportion of the user interface elements displayed on the LCD display 3224 can be based on the number and type of instruments plugged into the header/UI module 3002. These scalable graphics can provide the means to utilize more of the screen for better visualization.

In one aspect, the header/UI module 3002 may be configured to depict a user interface screen on the LCD display 3224 to indicate which ports of the modules connected to the modular energy system 3000 are active. In some aspects, the header/UI module 3002 can be configured to illustrate active versus inactive ports by highlighting active ports and dimming inactive ports. In one aspect, ports can be represented with color when active (e.g., monopolar tissue cut with yellow, monopolar tissue coagulation with blue, bipolar tissue cut with blue, advanced energy tissue cut with warm white, and so on). Further, the displayed color will match the color of the light piping around the ports. The coloring can further indicate that the user cannot change settings of other instruments while an instrument is active. As another example, the header/UI module 3002 can be configured to depict the bipolar, monopolar, and ultrasonic ports of a first energy module as active and the monopolar ports of a second energy module as likewise active.

In one aspect, the header/UI module 3002 can be configured to depict a user interface screen on the LCD display 3224 to display a global settings menu. In one aspect, the header/UI module 3002 can be configured to display a menu on the LCD display 3224 to control global settings across any modules connected to the modular energy system 3000. The global settings menu can be, for example, always displayed in a consistent location (e.g., always available in upper right hand corner of main screen).

In one aspect, the header/UI module 3002 can be configured to depict a user interface screen on the LCD display 3224 configured to prevent changing of settings while a surgical instrument is in use. In one example, the header/UI module 3002 can be configured to prevent settings from being changed via a displayed menu when a connected instrument is active. The user interface screen can include, for example, an area (e.g., the upper left hand corner) that is reserved for indicating instrument activation while a settings menu is open. In one aspect, a user has opened the bipolar settings while monopolar coagulation is active. In one aspect, the settings menu could then be used once the activation is complete. In one aspect, the header/UI module 3002 can be is configured to never overlay any menus or other information over the dedicated area for indicating critical instrument information in order to maintain display of critical information.

In one aspect, the header/UI module 3002 can be configured to depict a user interface screen on the LCD display 3224 configured to display instrument errors. In one aspect, instrument error warnings may be displayed on the instrument panel itself, allowing user to continue to use other instruments while a nurse troubleshoots the error. This allows users to continue the surgery without the need to stop the surgery to debug the instrument.

In one aspect, the header/UI module 3002 can be configured to depict a user interface screen on the LCD display 3224 to display different modes or settings available for various instruments. In various aspects, the header/UI module 3002 can be configured to display settings menus that are appropriate for the type or application of surgical instrument(s) connected to the stack/hub. Each settings menu can provide options for different power levels, energy delivery profiles, and so on that are appropriate for the particular instrument type. In one aspect, the header/UI module 3002 can be configured to display different modes available for bipolar, monopolar cut, and monopolar coagulation applications.

In one aspect, the header/UI module 3002 can be configured to depict a user interface screen on the LCD display 3224 to display pre-selected settings. In one aspect, the header/UI module 3002 can be configured to receive selections for the instrument/device settings before plugging in instruments so that the modular energy system 3000 is ready before the patient enters the operating room. In one aspect, the user can simply click a port and then change the settings for that port. In the depicted aspect, the selected port appears as faded to indicate settings are set, but no instrument is plugged into that port.

Figure 37:
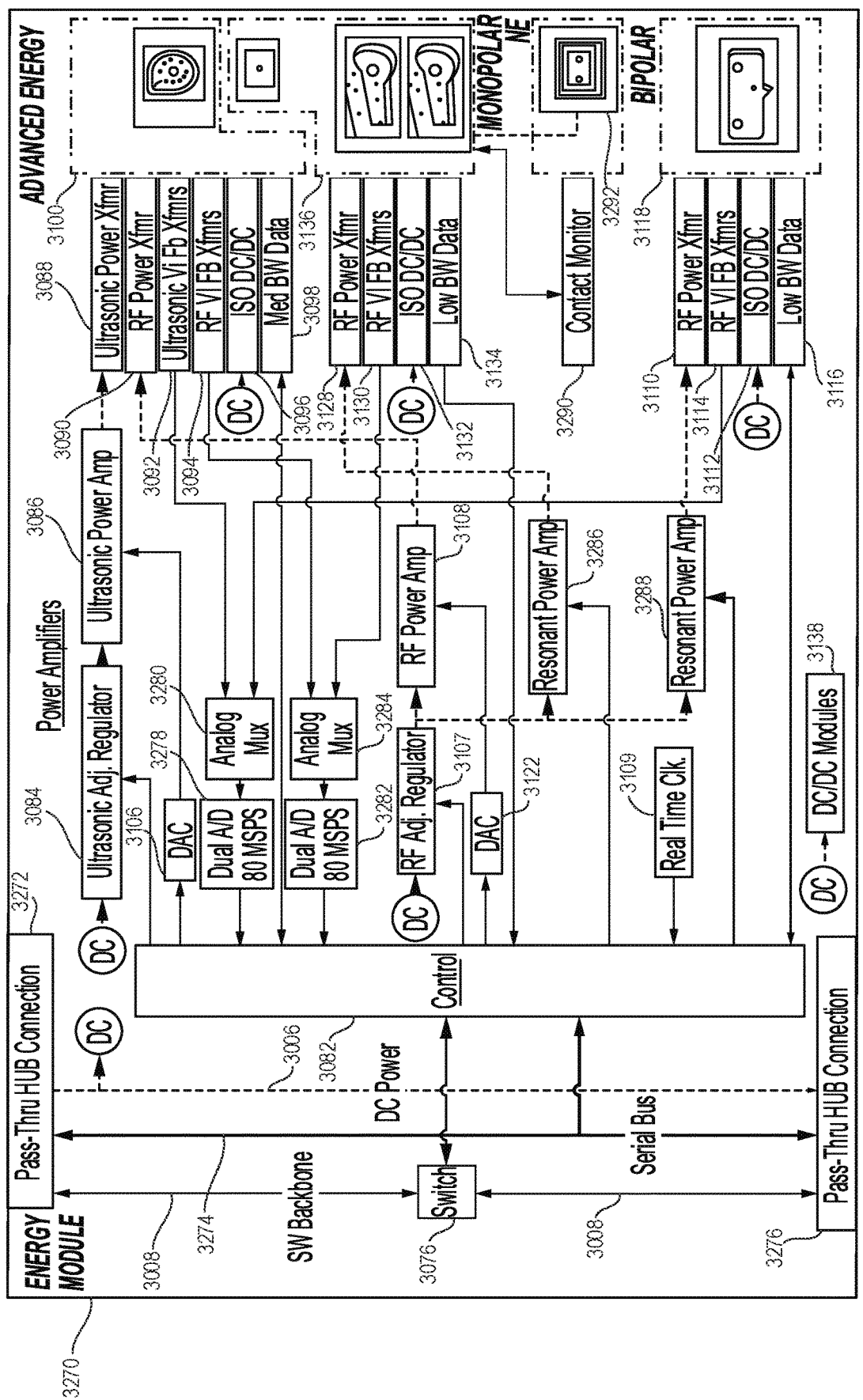
FIG. 37 is a block diagram of an energy module for a hub, such as the energy module depicted in FIGS. 31-36B, in accordance with at least one aspect of the present disclosure.

FIG. 37 is a block diagram of an energy module 3270 for a hub, such as the energy module depicted in FIGS. 31, 32, 34, and 35, in accordance with at least one aspect of the present disclosure. The energy module 3270 is configured to couple to a header module, header/UI module, and other energy modules via the first and second pass-through hub connectors 3272, 3276. A switch 3076 disposed between the first and second pass-through hub connectors 3272, 3276 receives, processes, and forwards data from the source device to the destination device and controls data communication therebetween. Data is received and transmitted through the data bus 3008. The energy module 3270 includes a controller 3082 to control various communications and processing functions of the energy module 3270.

DC power is received and transmitted by the energy module 3270 through the power bus 3006. The power bus 3006 is coupled to the DC/DC converter modules 3138 to supply power to adjustable regulators 3084, 3107 and isolated DC/DC converter ports 3096, 3112, 3132.

In one aspect, the energy module 3270 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of the advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog multiplexer 3280 and a dual analog-to-digital converter 3278 (A/D). In one aspect, the dual A/D 3278 has a sampling rate of 80 MSPS. Also coupled to the controller 3082 through the advanced energy receptacle 3100 is the isolated DC/DC converter port 3096, which receives DC power from the power bus 3006, and a medium bandwidth data port 3098.

In one aspect, the energy module 3270 can include a plurality of wideband RF power amplifiers 3108, 3286, 3288, among others, which in one aspect, each of the wideband RF power amplifiers 3108, 3286, 3288 may be linear class H amplifiers capable of generating arbitrary waveforms and drive RF loads at a range of output frequencies. Each of the wideband RF power amplifiers 3108, 3286, 3288 are fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the first wideband RF power amplifier 3108 via a DAC 3122.

Unlike the energy modules 3004, 3012 shown and described in FIGS. 34 and 35, the energy module 3270 does not include RF selection relays configured to receive an RF output signal from the adjustable buck regulator 3107. In addition, unlike the energy modules 3004, 3012 shown and described in FIGS. 34 and 35, the energy module 3270 includes a plurality of wideband RF power amplifiers 3108, 3286, 3288 instead of a single RF power amplifier. In one aspect, the adjustable buck regulator 3107 can switch between a plurality of states, in which the adjustable buck regulator 3107 outputs an output RF signal to one of the plurality of wideband RF power amplifiers 3108, 3286, 3288 connected thereto. The controller 3082 is configured to switch the adjustable buck regulator 3107 between the plurality of states. In a first state, the controller drives the adjustable buck regulator 3107 to output an RF energy signal to the first wideband RF power amplifier 3108. In a second state, the controller drives the adjustable buck regulator 3107 to output an RF energy signal to the second wideband RF power amplifier 3286. In a third state, the controller drives the adjustable buck regulator 3107 to output an RF energy signal to the third wideband RF power amplifier 3288.

The output of the first wideband RF power amplifier 3108 can be fed to an RF power transformer 3090, which is coupled to an RF output portion of an advanced energy receptacle 3100. RF voltage (V) and current (I) feedback (FB) signals, which may be employed to compute RF impedance, are fed back to the controller 3082 via RF VI FB transformers 3094 through an input portion of the advanced energy receptacle 3100. The RF voltage and current feedback signals are routed back to the controller 3082 through the RF VI FB transformers 3094, which are coupled to an analog multiplexer 3284 and a dual A/D 3282 coupled to the controller 3082. In one aspect, the dual A/D 3282 has a sampling rate of 80 MSPS.

The output of the second RF wideband power amplifier 3286 is fed through an RF power transformer 3128 of the RF monopolar receptacle 3136. Monopolar RF voltage (V) and current (I) feedback (FB) signals, which may be employed to compute RF impedance, are fed back to the controller 3082 via RF VI FB transformers 3130 through an input portion of the monopolar RF energy receptacle 3136. The RF voltage and current feedback signals are routed back to the controller 3082 through the analog multiplexer 3284 and the dual A/D 3282. Also coupled to the controller 3082 through the monopolar RF energy receptacle 3136 is the isolated DC/DC converter port 3132, which receives DC power from the power bus 3006, and a low bandwidth data port 3134.

The output of the third RF wideband power amplifier 3288 is fed through an RF power transformer 3110 of a bipolar RF receptacle 3118. Bipolar RF voltage (V) and current (I) feedback (FB) signals, which may be employed to compute RF impedance, are fed back to the controller 3082 via RF VI FB transformers 3114 through an input portion of the bipolar RF energy receptacle 3118. The RF voltage and current feedback signals are routed back to the controller 3082 through the analog multiplexer 3280 and the dual A/D 3278. Also coupled to the controller 3082 through the bipolar RF energy receptacle 3118 is the isolated DC/DC converter port 3112, which receives DC power from the power bus 3006, and a low bandwidth data port 3116.

A contact monitor 3290 is coupled to an NE receptacle 3292. Power is fed to the NE receptacle 3292 from the monopolar receptacle 3136.

In one aspect, with reference to FIGS. 31-37, the modular energy system 3000 can be configured to detect instrument presence in a receptacle 3100, 3118, 3136 via a photo-interrupter, magnetic sensor, or other non-contact sensor integrated into the receptacle 3100, 3118, 3136. This approach prevents the necessity of allocating a dedicated presence pin on the MTD connector to a single purpose and instead allows multi-purpose functionality for MTD signal pins 6-9 while continuously monitoring instrument presence.

In one aspect, with reference to FIGS. 31-37, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 31-37, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled and set to a high impedance state.

In one aspect, with reference to FIGS. 31-37, the modules of the modular energy system 3000 can include an amplifier pulse/stimulation/auxiliary DC amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

Energy Module Hardware

Some surgical procedures require the use of multiple different types of energy modalities. One option is to utilize multiple different surgical systems that are each configured to deliver one type of energy modality and switch between the surgical systems as needed during the course of the surgical procedure. However, in addition to the general convenience of having multiple different energy modalities available through a single system, a surgical system that is configured to deliver combinations of different energy modalities can provide a number of benefits and improved functionality over surgical systems that are configured to deliver a singular energy modality. For example, simultaneously delivering combinations of energy modalities can provide improved tissue coagulation as compared to a single energy modality. As another example, monopolar surgical systems can have issues with tissue adherence to the tip of the monopolar electrosurgical instrument. However, a surgical system configured to deliver both monopolar and ultrasonic energy can reduce tissue adherence to the surgical instrument when delivering monopolar energy by vibrating the end effector as energy is delivered. As yet another example, a surgical system configured to deliver monopolar energy in addition to other energy modalities can allow for the monopolar energy to be utilized as a supplement for the system's other energy modality, which can be useful for "touch up" coagulation. Accordingly, in various aspects, a surgical system configured to deliver multiple energy modalities can be configured to deliver bipolar, monopolar, and/or ultrasonic energy. Surgical systems that are configured to deliver combinations of energy modalities can further include a surgical generator or energy module that can deliver multiple energy modalities to the surgical instrument via a single port, thereby allowing a single surgical instrument to simultaneously or alternatively utilize the different energy modalities.

In various aspects, the present disclosure provides an amplifier circuit and port arrangement within a single energy module configured to deliver signals to surgical devices. The port is coupled to two separate monopolar energy sources, one bipolar energy source, and one advanced energy source, which includes, bipolar energy mode, monopolar energy mode, and ultrasonic energy mode. In a further aspect, the present disclosure provides an energy source connector that includes a pin arrangement configured to deliver bipolar energy, monopolar energy, and ultrasonic energy, where the monopolar pin has a different pin size and spacing from the other pins to prevent electrical arcing and shorting between pins. In yet a further aspect, the present disclosure provides a leakage current detection circuit on each port on an energy source to monitor for stray energy, which can be used to shut off an unwanted energy path.

Figure 38:
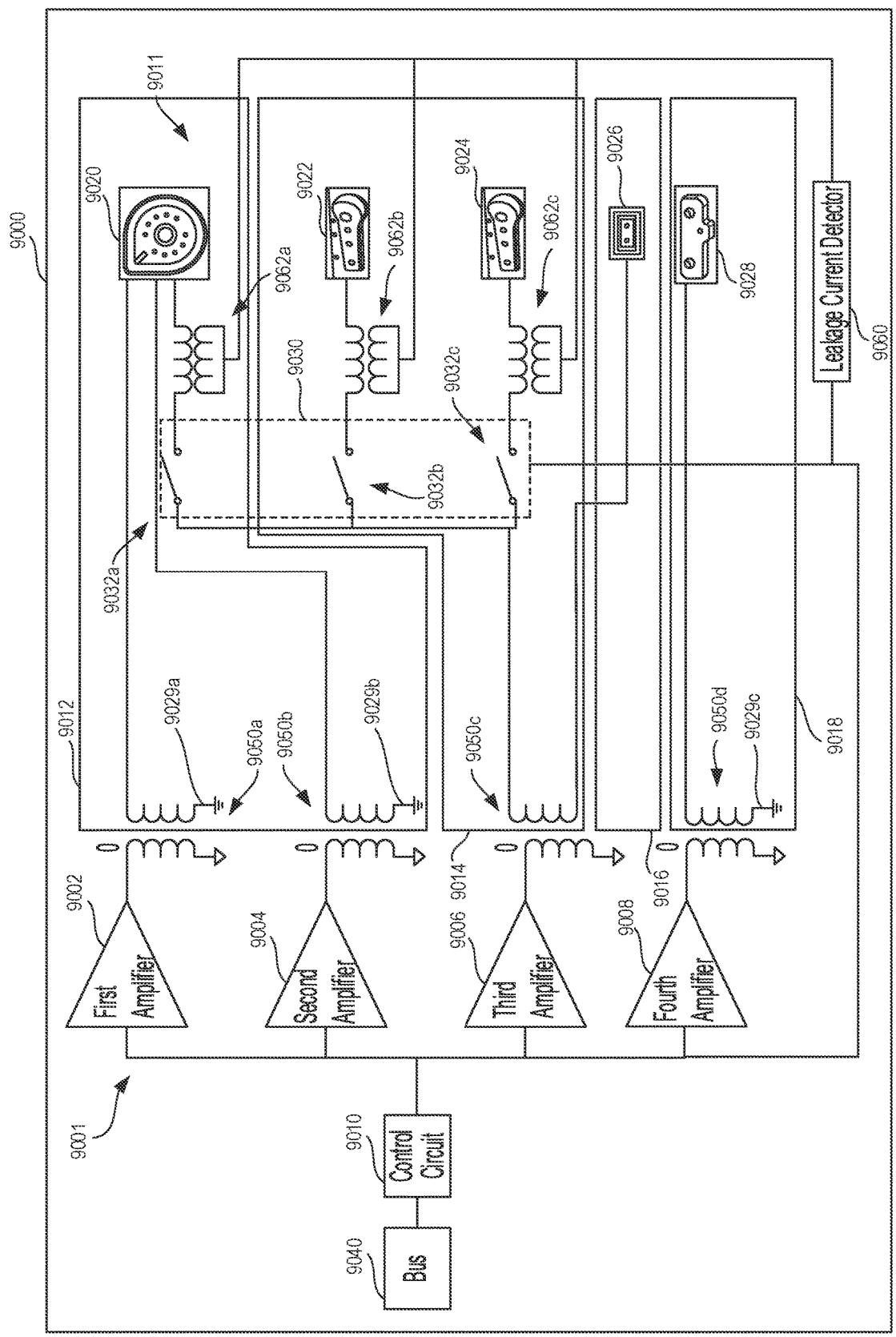
FIG. 38 is a block diagram of an energy module circuit, in accordance with at least one aspect of the present disclosure.

As described above in connection with FIGS. 21, 22, 24-30, and 33-37, an energy module 2004 can be configured to provide a variety of different energy modalities. For example, FIG. 38 is a block diagram of an energy module circuit 9000 for an energy module 2004 that is configured to deliver multiple energy modalities to a surgical instrument connected to the energy module 2004. The energy module circuit 9000 includes an energy drive assembly 9001 that is configured to generate the electrical signals for driving the various energy modalities applied by the surgical instrument connected to the energy module 2004. The energy drive assembly 9001 can include various circuitry and/or other hardware components for generating, controlling, and delivering drive signals for driving monopolar electrosurgical energy, bipolar electrosurgical energy, ultrasonic energy, or other energy modalities, and combinations thereof, at a surgical instrument coupled to the energy module 2004. In this particular example, the energy drive assembly 9001 includes a first amplifier 9002 configured to drive a first energy modality, a second amplifier 9004 configured to drive a second energy modality, a third amplifier 9006 configured to drive a third energy modality, and a fourth amplifier 9008 configured to drive a fourth energy modality. The amplifiers 9002, 9004, 9006, 9008 can be configured to drive the same or different energy modalities. The various amplifiers 9002, 9004, 9006, 9008 can include an ultrasonic amplifier capable of generating arbitrary waveforms to drive ultrasonic transducers at low total harmonic distortion (THD) levels and/or a bipolar and/or monopolar electrosurgical amplifier capable of generating arbitrary waveforms to drive RF loads at a range of output frequencies. The waveforms generated by the various amplifier types can also be referred to as "drive signals" for the different energy modality types. Further, such amplifiers can include linear or resonant amplifiers. In one particular implementation of the energy module circuit 9000, the first amplifier 9002 can include an ultrasonic amplifier, the second amplifier 9004 can include a bipolar electrosurgical amplifier, the third amplifier 9006 can include a monopolar electrosurgical amplifier, and the fourth amplifier 9008 can include another bipolar electrosurgical amplifier. However, the energy drive assembly 9001 can include other numbers and combinations of amplifiers, such as with the energy module 3004 shown in FIG. 34, for example. Further, the energy drive assembly 9001 can include a variety of other circuit components, such as is described in connection with the energy modules 3004, 3270 shown in FIGS. 34, 35, and 37.

The energy module circuit 9000 further includes a receptacle or port assembly 9011 that is electrically coupled to the energy drive assembly 9001. In this particular example, the port assembly 9011 includes a first port 9020, a second port 9022, a third port 9024, a fourth port 9026, and a fifth port 9028. The ports 9020, 9022, 9024, 9026, 9028 (which can also be referred to as receptacles) can be configured to, for example, receive or engage with corresponding connectors associated with surgical instruments (or cables to which the surgical instruments are connected) or connectors for an energy module/surgical system accessory (e.g., a monopolar return pad). In this particular example, the first port 9020 is electrically coupled or couplable to each of the first amplifier 9002, the second amplifier 9004, and the third amplifier 9006 and is thus capable of delivering up to three different energy modalities, one of which is driven by each of the respective amplifiers 9002, 9004, 9006. The second port 9022 and the third port 9024 are each electrically coupled to the third amplifier 9006 and are thus capable of delivering the same energy modality driven therefrom. The fourth port 9026 is electrically coupled to an electrical ground for the third amplifier 9006 and thus serves as an electrical return path for the energy modality driven by the third amplifier 9006 through at least one of the first, second, or third ports 9020, 9022, 9024. For example, the fourth port 9026 can serve as a connection point for a monopolar return pad for aspects where the third amplifier 9006 is a monopolar amplifier (as a monopolar electrosurgical instrument, as opposed to a bipolar electrosurgical instrument, must be used in connection with a monopolar return pad). The fifth port 9028 is electrically coupled to the fourth amplifier 9008 and is thus capable of delivering an energy modality driven therefrom.

In one aspect, the energy module circuit 9000 can be divided into a multiple isolated circuit portions or stages. Each of the circuit portions can be electrically isolated from the other circuit portions for safety purposes and compliance with electrosurgical generator technical standards, such as IEC 60601. Each of the isolated circuit portions can be coupled to the energy drive assembly 9001 via one or more isolation transformers. An isolation transformer is utilized to transfer electrical power from a source of AC power to a recipient device, in this case, the isolated circuit portions, while isolating the recipient device from the power source. Further, the isolated circuit portions can include one or more local grounds for electrically isolating the components of the energy drive assembly 9001 corresponding to that circuit portion from the components corresponding to the other circuit portions. Accordingly, each of the circuit portions are electrically isolated from each other. In the particular implementation illustrated in FIG. 38, the energy module circuit 9000 includes a first isolated circuit portion 9012 corresponding to the first port 9020, a second isolated circuit portion 9014 corresponding to the second and third ports 9022, 9024, a third isolated circuit portion 9016 corresponding to the fourth port 9026, and a fourth isolated circuit portion 9018 corresponding to the fifth port 9028. The first isolated circuit portion 9012 is coupled to the first and second amplifiers 9002, 9004 via a first isolation transformer 9050a and a second isolation transformer 9050b, respectively. The first isolated circuit portion 9012 is further couplable to the third amplifier 9006, through the switch assembly 9030, via a third isolation transformer 9050c. The second isolated circuit portion 9014 is coupled to the third amplifier 9006 via the third isolation transformer 9050c. The third isolated circuit portion 9016 is coupled to the return terminal of the third isolation transformer 9050c. Lastly, the fourth isolated circuit portion 9018 is coupled to the fourth amplifier 9008 via a fourth isolation transformer 9050d. Further, the first isolated circuit portion 9012 includes a first isolated local ground 9029a and a second isolated local ground 9029b for the first isolation transformer 9050a and the second isolation transformer 9050b, respectively. The fourth isolated circuit portion 9018 includes a third isolated local ground 9029c for the fourth isolation transformer 9050d. The third isolated circuit portion 9016 is electrically isolated from the other circuit portions 9012, 9014, 9018 via the connection between the fourth port 9026 and the return terminal of the third isolation transformer 9050c. The fourth port 9026 can likewise, in part, serve the electrical isolation of the first isolated circuit portion 9012 when the first switch 9032a is in its closed state and the first port 9020 is coupled to the third amplifier 9006 through the third isolation transformer 9050c. In addition to generally seeking to comply with applicable technical standards, dividing the energy module circuit 9000 into multiple isolated circuit portions 9012, 9014, 9016, 9018 in this manner ensures that surgical components that are intended to come into contact with patients are not inadvertently energized when other components or circuits are energized, which, in turn, promotes patient and operator safety.

It should be noted that the particular implementation of the energy module circuit 9000 illustrated in FIG. 38 for an energy module 3004 is only provided for illustrative purposes. Various other arrangements or combinations of amplifiers 9002, 9004, 9006, 9008 within the energy drive assembly 9001, isolated circuit portions 9012, 9014, 9016, 9018, and/or ports 9020, 9022, 9024, 9026, 9028 are within the scope of the present disclosure, including different numbers or amplifiers 9002, 9004, 9006, 9008 or amplifiers 9002, 9004, 9006, 9008 that drive different combinations of energy modalities, isolated circuit portions 9012, 9014, 9016, 9018 that include different combinations of components or are otherwise arranged in different manners, and so on.

As described above, in one aspect, the energy module circuit 9000 can include a circuit (e.g., the first isolated circuit portion 9012 and/or other associated components, such as the first, second, and third amplifiers 9002, 9004, 9006) that is configured to deliver multiple different energy modalities to a surgical instrument connected to the port (e.g., the first port 9020) associated with the particular circuit. In one aspect, a surgical instrument receiving multiple energy drive signals can be configured to simultaneously or individually apply the driven energy modalities to tissue. In another aspect, such a surgical instrument can be configured to utilize one or more of the driven energy modalities for non-tissue treatment purposes, such as sensing or for driving secondary functions of the surgical instrument. For example, a drive signal from a bipolar amplifier (e.g., the second amplifier 9004) can be driven at nontherapeutic frequencies (i.e., below the minimum frequency necessary to induce treatment effects in tissue to which the signal is applied) for sensing various tissue properties, such as tissue thickness or tissue type. As another signal, a drive signal from an ultrasonic amplifier (e.g., the first amplifier 9002) can be driven at nontherapeutic frequencies to vibrate an end effector to prevent tissue adhesion thereto as monopolar or bipolar energy is applied to tissue to prevent tissue adhesion to the end effector. In yet another aspect, energy module drive signals can be utilized to power secondary or nontherapeutic components of connected surgical instruments, as is described herebelow.

Figure 39:
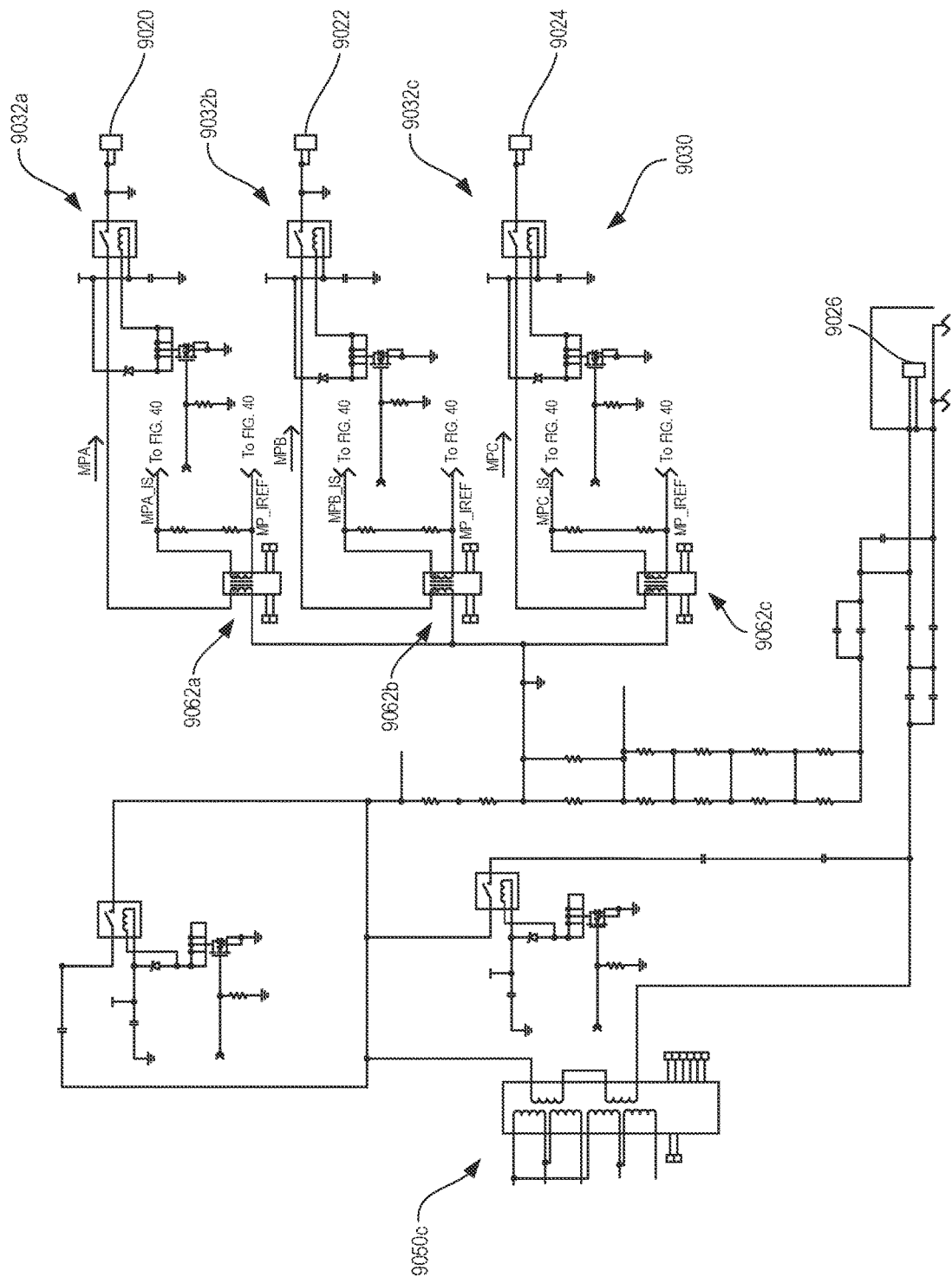
FIG. 39 is a diagram of an energy module circuit, in accordance with at least one aspect of the present disclosure.

Because of the significant number of hardware components required by the energy modules 2004 described herein for driving all of the various combinations of energy modalities, it would generally be desirable to utilize hardware components for multiple different purposes within the energy modules 2004 in order to minimize the hardware footprint of the energy modules 2004. In one aspect, one or more amplifiers of the energy driver assembly 9001 can be interchangeably couplable to one or more ports of the port assembly 9011 via a switch assembly 9030. In this particular example, the third amplifier 9006 is interchangeably couplable to each of the first port 9020, the second port 9022, and the third port 9024 via the switch assembly 9030. The switch assembly 9030 includes a first switch 9032a for coupling the third amplifier 9006 to the first port 9020, a second switch 9032b for coupling the third amplifier 9006 to the second port 9022, and a third switch 9032c for coupling the third amplifier 9006 to the third port 9024. Each of the switches 9032a, 9032b, 9032c can be transitioned between an open position/state in which the third amplifier 9006 is decoupled from the respective port 9020, 9022, 9024 and a closed position/state in which the third amplifier 9006 is coupled to the respective port 9020, 9022, 9024. Accordingly, the third amplifier 9006 can be configured to generate an electrical drive signal for driving its respective energy modality, which can be provided to a surgical instrument through the first port 9020, the second port 9022, and/or the third port 9024 according to which of the respective switches 9032a, 9032b, 9032c is in its closed position or state. In various aspects, the switch assembly 9030 can be controlled by a control circuit 9010, which is described further below, to selectively control which of the ports 9020, 9022, 9024 the third amplifier 9006 is coupled to. Further, FIG. 39 illustrates a circuit diagram providing additional detail regarding the circuit architecture of the third amplifier 9006 and the switch assembly 9030. Utilizing a switching assembly 9030 to interchangeably connect an amplifier from the energy driver assembly 9001 to multiple ports utilizing the same energy modality, as opposed to dedicating a unique amplifier configured to drive the appropriate energy modality to each port, simplifies the internal structure of the energy module 3004 by reusing the third amplifier 9006 across multiple ports. Reusing the third amplifier 9006, in turn, reduces cost and saves space within the energy module 3004. Further, the illustrated circuit architecture eliminates the need for relays to be integrated within the circuit pathway for the neutral electrode port (i.e., the fourth port 9026 in the particular example illustrated in FIG. 38) because a single neutral electrode pathway can be dedicated to the monopolar energy-providing third amplifier 9006.

Figure 40:
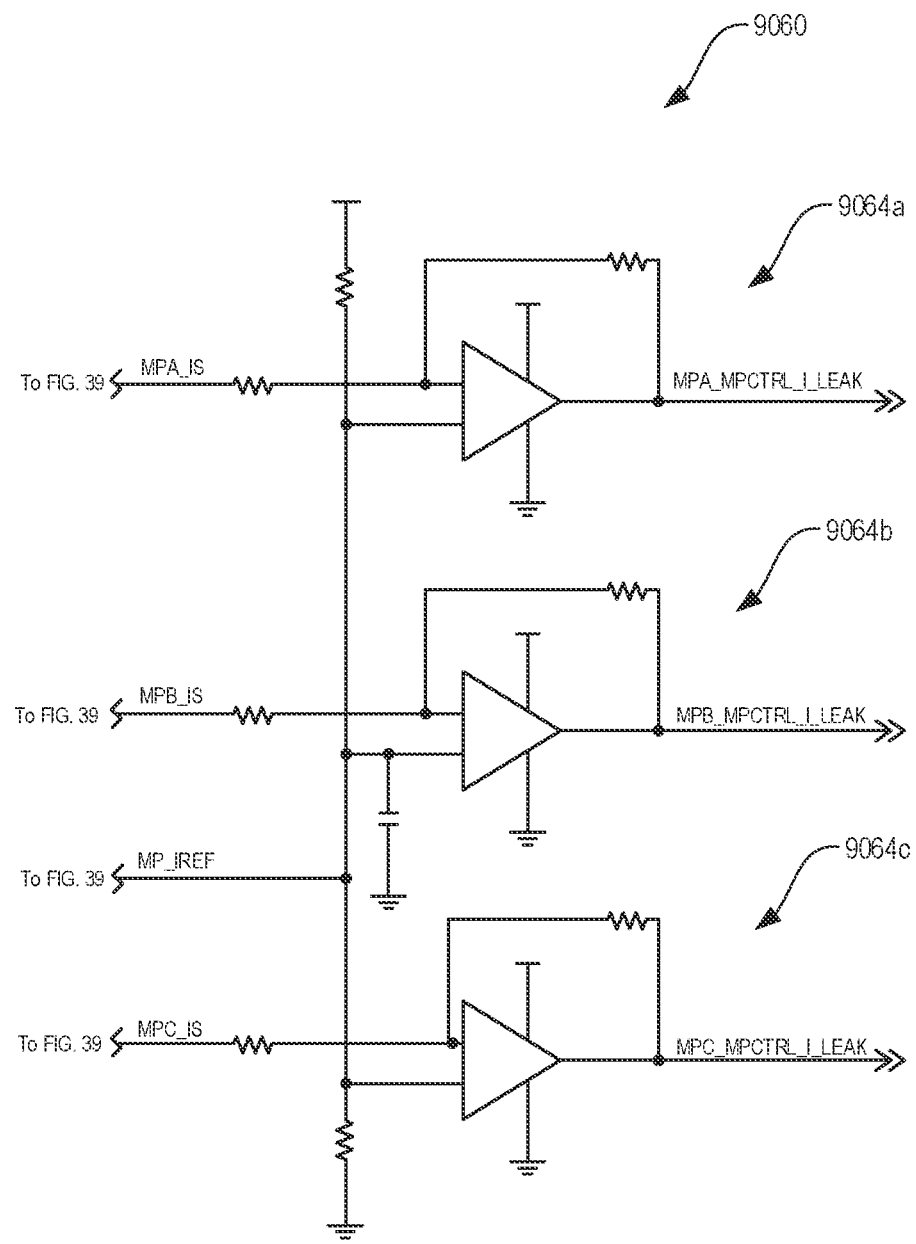
FIG. 40 is a diagram of a leakage current detector circuit, in accordance with at least one aspect of the present disclosure.

For operator and patient safety purposes, it is desirable for surgical generator/energy systems having multiple monopolar ports (such as with the energy module 3004 described above) to include systems to ensure that the monopolar energy is only driven to the intended monopolar port/instrument. In one aspect, the energy module circuit 9000 can further include a leakage current detector circuit 9060 coupled to each of the ports 9020, 9022, 9024 to which the switch assembly 9030 is configured to interchangeably couple the third amplifier 9006 (which, in the example described above, is configured to provide a monopolar drive signal). The leakage current detector circuit 9060 can be embodied as one or multiple circuit portions that are included within or coupled to the electrical pathways for the ports 9020, 9022, 9024. The leakage current detector circuit 9060 can be configured to determine whether monopolar energy/drive signal is being inadvertently transmitted from the third amplifier 9006 to the respective port 9020, 9022, 9024. In one aspect, the leakage current detector circuit 9060 can be coupled to each pathway for the first, second, and third pots 9020, 9022, 9024 via a respective current sensing transformer 9062a, 9062b, 9062c. As can be seen in FIG. 40, the leakage current detector circuit 9060 can receive as input a first sensed electrical current (MPA_IS) corresponding to the monopolar output current (MPA) transmitted to the first port 9020, a second sensed electrical current (MPB_IS) corresponding to the monopolar output current (MPB) transmitted to the second port 9022, a third sensed electrical current (MPC_IS) corresponding to the monopolar output current (MPC) transmitted to the third port 9024, and a reference current (MP_IREF). The leakage current detector circuit 9060 can further include a pass/fail comparator 9064a, 9064b, 9064c for each of the current sensing transformer 9062a, 9062b, 9062c. Each of the pass/fail comparators 9064a, 9064b, 9064c is configured to change its output state according to whether it senses a monopolar output. The output of the leakage current detector circuit 9060 can include one or more signals (labeled: MPA_MPCTRL_I_LEAK, MPB_MPCTRL_I_LEAK, and MPC_MPCTRL_I_LEAK) that are output by the pass/fail comparator 9064a, 9064b, 9064c according to their states. The output signals can each indicate whether the port 9020, 9022, 9024 to which the output signal corresponds is receiving monopolar output (i.e., a monopolar drive signal), which can in turn be utilized to determine whether any of the ports 9020, 9022, 9024 are inadvertently receiving monopolar output. These output signals from the comparators 9064a, 9064b, 9064c can be communicated to the control circuit 9010, which can then control the third amplifier 9006 and/or switch assembly 9030 based upon whether leakage current is detected. For example, when a leakage current is detected, the control circuit 9010 can cause the third amplifier 9006 to cease outputting the drive signal. As another example, when a leakage current is detected, the control circuit 9010 can cause the switch assembly 9030 to transition the appropriate switch 9032a, 9032b, 9032c to its closed position/state to halt the unintended delivery of the drive signal to the port 9020, 9022, 9024 at which the leakage current was detected.

As noted above, the energy module circuit 9000 can further include a control circuit 9010 that is communicably coupled to the energy drive assembly 9001, the switch assembly 9030, and/or the leakage current detector circuit 9060. The control circuit 9010 can further be communicably coupled to a bus 9040 for transmitting and receiving information/signals to and from other modules with a modular energy system 3000 (FIGS. 31-37) or external systems, as is described in FIG. 34. In one aspect, the control circuit 9010 can include the controller 3082 described in connection with FIGS. 33-37. The control circuit 9010 can further be configured to execute various algorithms or processes for controlling the energy module 3004.

Figure 41:
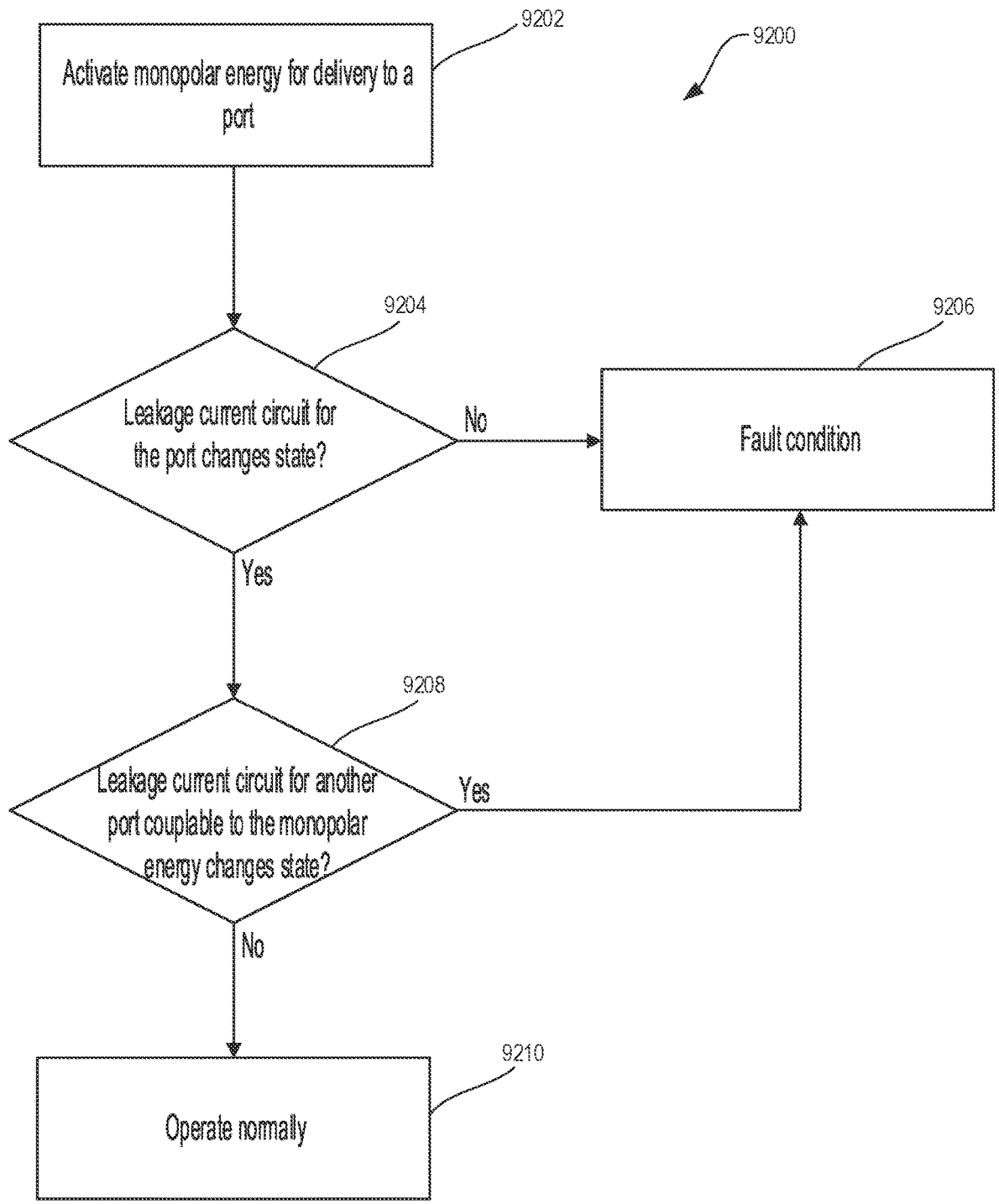
FIG. 41 is a logic flow diagram of a process for monitoring an energy module circuit for monopolar leakage current, in accordance with at least one aspect of the present disclosure.

In one aspect, the control circuit 9010 can be configured to monitor the energy module circuit 9000 to determine when monopolar energy is inadvertently being applied to one or more ports of the energy module 3004. For example, the control circuit 9010 can be configured to execute the process 9200 illustrated in FIG. 41. The process 9200 can be embodied as, for example, instructions stored in a memory coupled to the control circuit 9010 that, when executed by the control circuit 9010, cause the control circuit 9010 to perform the enumerated steps of the process 9200. In the following description of the process 9200, reference should also be made to FIGS. 38-40.

Accordingly, the control circuit 9010 executing the process 9200 activates 9202 monopolar energy for delivery to one of the ports of the port assembly 9011. For example, the control circuit 9010 can cause a monopolar amplifier of the energy module 3004 (e.g., the third amplifier 9006) to generate a monopolar electrosurgical drive signal, which is delivered by the isolation transformer 9050c to the patient-isolated side of the energy module circuit 9000, then through the switch assembly 9030 to one of the ports 9020, 9022, 9024.

Accordingly, the control circuit 9010 determines 9204 whether the port to which the monopolar electrosurgical drive signal is intended to be driven changes state. As discussed above, in one aspect, the control circuit 9010 can receive a signal from the comparators 9064a, 9064b, 9064c of the leakage current detector circuit 9060 corresponding to the intended port. If the received signal indicates that energy is not being applied to the intended port, then the process 9200 can proceed along the NO branch and the control circuit 9010 determines 9206 that a fault condition has occurred because the port that is intended to be energized is not in fact being energized. If the received signal indicates that energy is being applied to the intended port, then the process 9200 can proceed along the YES branch and the control circuit 9010 determines 9208 whether another port configured to delivery monopolar energy has changed state. In other words, the control circuit 9010 determines 9208 whether the ports couplable to the monopolar amplifier via the switch assembly 9030, other than the intended port, are being energized by the monopolar amplifier. As discussed above, the control circuit 9010 can likewise receive signals from the comparators 9064a, 9064b, 9064c of the leakage current detector circuit 9060 that correspond to the other ports coupled to the switch assembly 9030. If the received signal(s) indicate(s) that energy is being applied to the other ports, then the process 9200 can proceed along the YES branch and the control circuit 9010 determines 9206 that a fault condition has occurred because at least one port is being inadvertently energized with monopolar energy. If the received signal(s) indicate(s) that energy is not being applied to the other ports, then the process 9200 can proceed along the NO branch and the control circuit 9010 determines 9210 that the energy module 3004 is operating normally.

In the event that the control circuit 9010 executing the process 9200 determines 9206 that a fault condition has occurred, the control circuit 9010 can take a variety of different actions, including providing an alert to the user (e.g., via the display 2006 in FIGS. 24-30) or deactivating the energy drive assembly 9001 or a component thereof (e.g., the monopolar amplifier).

In other aspects, a control circuit 9010 can be configured to control the energy module 3004 in a variety of other ways. For example, a control circuit 9010 can be configured to control the power level of or waveform generated by the energy drive assembly 9001, the switch assembly 9030 to selectively couple or decouple the monopolar amplifier to one or more ports, and/or various other components of the energy module 3004 based on sensed parameters.

As noted above, the energy module circuit 9000 can be delineated into multiple isolated circuit portions 9012, 9014, 9016, 9018. Further, the first and second isolated circuit portions 9012, 9014 could, via the switch assembly 9030, potentially be both coupled to the same amplifier (i.e., the third amplifier 9006). As the isolated circuit portions 9012, 9014, 9016, 9018 are intended to be electrically isolated from each other, it can be beneficial to ensure that only one of the first and second isolated circuit portions 9012, 9014 is coupled to the third amplifier 9006 at any given time. In one aspect, the control circuit 9010 can be configured to control the relay 9030 such that only one of the first and second isolated circuit portions 9012, 9014 is coupled to the third amplifier 9006 at any given time. For example, the control circuit 9010 can be configured to detect the position/state of each of the switches 9032a, 9032b, 9032c. If the control circuit 9010 determines that the first switch 9032a has transitioned from its open position/state to its closed position/state, then in response, the control circuit 9010 can control the switch assembly 9030 to transition the second and third switches 9032b, 9032c to their open position/state. Correspondingly, if the control circuit 9010 determines that at least one of the second or third switches 9032b, 9032c has transitioned from its open position/state to its closed position/state, then in response, the control circuit 9010 can control the switch assembly 9030 to transition the first switch 9032a to its open position/state. As another example, the control circuit 9010 can monitor the leakage current detector circuit 9060 to determine which ports are receiving monopolar output, as is described above, and then control the relay assembly 9030 accordingly to ensure that only the first port 9020 or the second and third ports 9022, 9024 are coupled to the third amplifier 9006.

Figure 42:
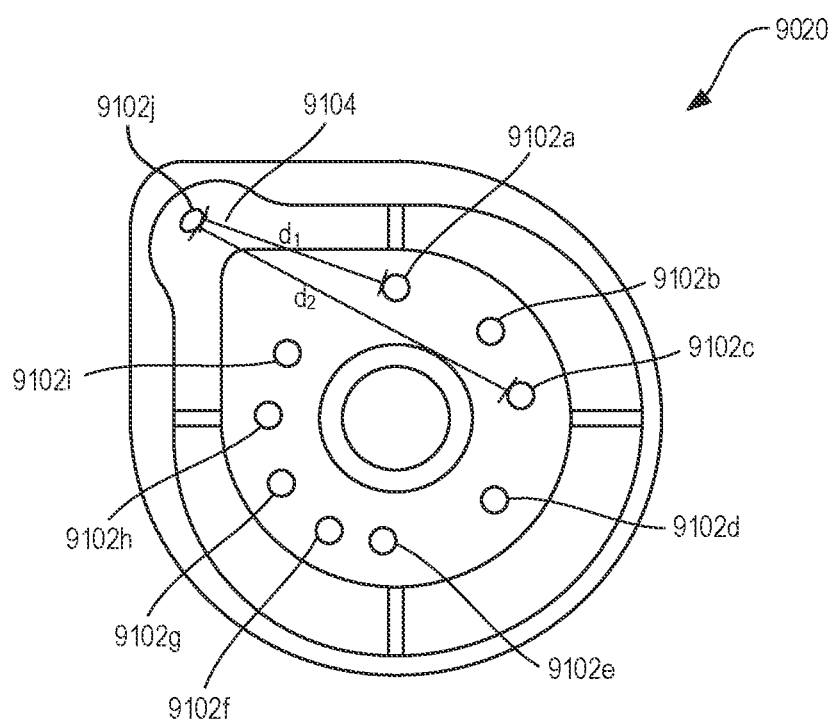
FIG. 42 is a view of an electrical connector port configured to deliver multiple energy modalities, in accordance with at least one aspect of the present disclosure.

As described in various aspects above, the first port 9020 can be configured to deliver a combination of different energy modalities. Accordingly, as illustrated in FIG. 42, the first port 9020 can include a pin arrangement comprising a number of electrical pins or contacts 9102a-j that are positioned to engage with corresponding electrical pins or contacts of a connector that is configured to engage with the port 9020. The electrical contacts 9102a-j are configured to relay the drive signals generated by the energy module 3004 and/or support sensing and communications between the surgical instrument and the energy module 3004. In one aspect, the port 9020 can include an electrical contact that is dedicated to each of the energy modalities that the port 9020 is configured to deliver to a surgical instrument connected thereto. For example, a first contact 9102a can be configured to deliver an ultrasonic drive signal, a second contact 9102c can be configured to deliver a bipolar electrosurgical drive signal, and a third contact 9102j can be configured to deliver a monopolar electrosurgical drive signal to a connected surgical instrument. In various aspects, the first contact 9102a, second contact 9102c, and third contact 9102j can be arranged to prevent electrical interference between the contacts 9102a, 9102c, 9102j. In one aspect, the third contact 9102j can be offset or spaced away from the first and second contacts 9102a, 9102c by a distance sufficient to prevent electrical arcing and shorting that could be caused by the high-voltage, high-crest factor monopolar drive signal. For example, the third contact 9102j can be positioned a distance $d_1$ from the first contact 9102a and a distance $d_2$ from the second contact 9102c. The distances $d_1$ and $d_2$ can be selected to be at least the minimum necessary distances required to prevent electrical arcing and shorting between the contacts 9102a, 9102c, 9102j and/or comply with relevant safety/technical standards, such as IEC 60601.

Surgical Instrument Circuitry

Some electrosurgical instruments may require a large amount of direct current (DC) power for powering particular components or performing particular functions. For example, a surgical instrument may include one or more motors to control articulation, clamp force, blade firing, and other parameters of the instrument. As another example, a surgical instrument may include a high-power light-emitting diode (LED) used to illuminate the body cavity. However, some interfaces between a surgical generator (e.g., an energy module) and the electrosurgical and/or ultrasonic instruments may not support this type of high-power DC output.

In various aspects, the present disclosure provides an electrical energy source configured to deliver energy in two patient domains through the same connector to avoid one powered "hot" device out of two coupled to the same connector. For example, this situation may arise if a device includes two end-effectors extending from a single connector. In this environment, the present disclosure provides isolation techniques that can be employed to deliver a flexible auxiliary power supply for an energy device. The present disclosure further provides various circuits configured to enable delivery of energy from the same port in two patient domains, and to deactivate one of two devices from that port.

In one general aspect, the present disclosure provides a surgical generator (e.g., an energy module) connectable to a surgical instrument. The surgical instrument comprises an end effector to deliver energy to a tissue, the surgical energy module comprising a first high power amplifier, a second high power amplifier, and a control circuit coupled to the first high power amplifier and the second high power amplifier. The control circuit configured to cause the first high power amplifier to power the end effector to deliver energy to the tissue and cause the second high power amplifier to power a secondary function of the surgical instrument.

In another general aspect, the present disclosure provides a surgical energy module connectable to a surgical instrument. The surgical energy module comprises a first circuit configured to provide ultrasonic energy to the surgical instrument, a second circuit configured to provide bipolar electrosurgical energy to the surgical instrument, and a third circuit configured to provide monopolar electrosurgical energy to the surgical instrument. The first circuit, the second circuit, and the third circuit are electrically isolated from each other.

Figure 43:
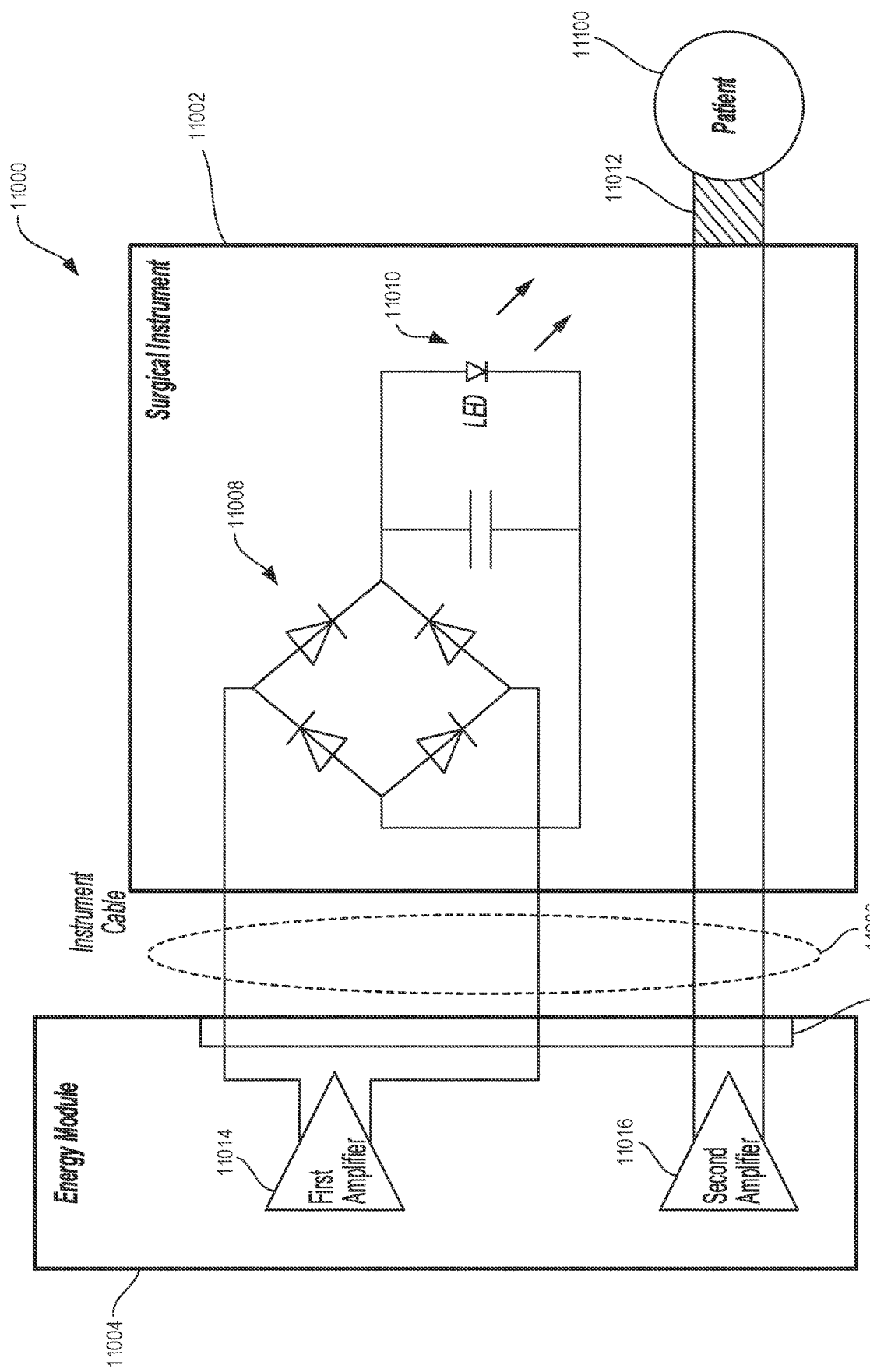
FIG. 43 is a block diagram of a surgical system, in accordance with at least one aspect of the present disclosure.

FIG. 43 is a block diagram of a surgical system 11000 including a surgical instrument 11002 connected to an energy module 11004, such as the various energy modules described in connection with FIGS. 24-37, via a cable assembly 11006. As described above in fuller detail with respect to FIGS. 31-37, the energy module 11004 can be configured to provide multiple different energy modality output or drive signals to a surgical instrument 11002 via a single receptacle 11005, such as the advanced energy receptacle 3100 illustrated in FIGS. 34 and 35. In particular, the energy module 11004 can include various amplifiers 11014, 11016 and associated circuit components for generating drive signals to drive an energy modality deliverable by a connected surgical instrument 11002 for cutting, coagulating, or otherwise therapeutically treating tissue. The generated drive signals can have different frequency ranges according to the energy modality type that the drive signal drives. In one implementation of the energy module 11004, the first amplifier 11014 can include an ultrasonic amplifier and the second amplifier 11016 can include a bipolar or monopolar electrosurgical amplifier. Accordingly, the first amplifier 11014 can be configured to generate an AC drive signal configured to actuate an ultrasonic transducer for driving an ultrasonic blade of the surgical instrument 11002, as described in connection with FIGS. 17 and 18. Accordingly, the second amplifier 11016 can be configured to generate an AC drive signal configured to cause electrodes of the surgical instrument 11002 to deliver electrosurgical RF current to captured tissue, as described in connection with FIG. 19. Additional detail regarding energy module/generator circuit configurations for delivering various combinations of energy modalities can be found in herein.

Although various energy modules 11004 described herein can include multiple amplifier types for driving different energy modalities, not all surgical instruments 11002 connectable to the energy modules 11004 may require the use of the available energy modalities for treating tissue. Accordingly, one or more of the amplifiers may be unused for particular types of surgical instruments 11002. For example, when a bipolar electrosurgical instrument is connected to the energy module 11004, the bipolar amplifier (e.g., the second amplifier 11016) may be utilized for tissue treatment, but the ultrasonic amplifier (e.g., the first amplifier 11014) may be unused for tissue treatment. Such energy modules 11004 present a unique advantage in such situations where the surgical instrument 11002 connected to the energy module 11004 does not require the use of each of the amplifiers at any given time during a surgical procedure. Namely, the one or more amplifiers that are not presently in use for therapeutically treating tissue can be utilized by the surgical instrument 11002 as secondary power sources for powering other components and/or functions of the surgical instrument 11002.

In one aspect, a surgical instrument 11002 can be configured to utilize drive signals provided from the energy module 11004 to alternatively drive or power non-therapeutic energy application functions or components of the surgical instrument 11002. For example, the surgical instrument 11002 may be configured to utilize an energy modality that is driven by the second amplifier 11016 (e.g., RF electrosurgical energy) but not an energy modality that is driven by the first amplifier 11014 (e.g., ultrasonic energy). In one aspect, the surgical instrument 11002 can include circuitry configured to utilize the amplifier(s) driving energy modalities that the surgical instrument 11002 is not configured to deliver as a DC power source. In the illustrated aspect, the surgical instrument 11002 includes a rectifier 11008 (e.g., a full-wave rectifier) that is configured to convert the AC drive generated by the first amplifier 11014 into an output DC voltage. The surgical instrument 11002 can include various additional hardware and/or software (e.g., a filter or a voltage regulator) for processing or smoothing the output of the rectifier 11008. The output DC voltage can then be utilized to power various components or functions of the surgical instrument 11002, such as a light source 11010 (e.g., an LED). The light source 11010 can be positioned on the surgical instrument 11002 for illuminating the body cavity of the patent on which the surgical procedure is being performed, for example. In various aspects, the converted drive signal can be utilized to provide auxiliary power to the surgical instrument 11002 for a variety of different applications, including nerve stimulation (e.g., powering a waveform generator configured to generate signals of a predetermined frequency for stimulating nerves), powering electromechanical components of the surgical instrument 11002 (e.g., a motor) or other loads associated with the surgical instrument 11002 (e.g., a light source 11010), powering a processor or control circuit implementing various control algorithms, powering sensors for detecting various parameters (e.g., tissue impedance, temperature, 3D acceleration, clamp arm gap, clamp force, tissue type identification, or critical structure identification), and/or charging a battery of the surgical instrument 11002. In such aspects, the components and/or functions powered by the output DC voltage may be controlled simultaneously with energy delivery by the surgical instrument 11002 driven by the other drive signals generated by the energy module 11004 (e.g., controlling the clamp arm force or controlling the tissue gap as the tissue is therapeutically treated). The remaining amplifiers of the energy module 11004 to which the surgical instrument 11002 is electrically coupled through the connection to the receptacle 11005, such as the second amplifier 11016 in the particular implementation in FIG. 43, can be utilized as normal to deliver the driven energy modality through the end effector 11012 to therapeutically treat tissue of the patient 11100 during a surgical procedure.

In an alternative aspect, the cable assembly 11006, rather than the surgical instrument 11002, can include circuitry disposed therein that is configured to convert drive signals provided from the energy module 11004 to an alternative form suitable for driving or powering non-therapeutic energy application functions or components of the surgical instrument 11002. For example, the cable assembly 11006 can include a rectifier 11008 that is configured to convert the AC drive generated by the first amplifier 11014 into an output DC voltage. Accordingly, the cable assembly 11006 can receive drive signals generated by the energy module 11004 through its connection to the receptacle 11005, convert one or more of the drive signals into an output DC voltage, and then provide the output DC voltage to the surgical instrument 11002 to which it is connected for various applications, which are described above.

Although FIG. 43 depicts the surgical instrument 11002 as including a single rectifier 11008, the surgical instrument 11002 and/or cable assembly 11006 can, in one aspect, include multiple rectifiers for converting multiple different drive signals generated by the energy module 11004 into DC output voltages. These DC outputs voltages can power the same or different components and/or functions of the surgical instrument 11002. Further, the multiple rectifiers can be configured to convert the same or different drive signals generated by the energy module 11004. For example, the surgical instrument 11002 and/or cable assembly 11006 can include a first rectifier configured to convert a first drive signal generated by the first amplifier 11014 to a first output DC voltage and a second rectifier configured to convert a second drive signal generated by the second amplifier 11016 to a second output DC voltage. The surgical instrument 11002 can be configured to utilize the first and second output DC voltages to power the same or different components of the surgical instrument 11002.

In some aspects, the surgical instrument 11002 may be configured to utilize only one or less than all of the energy modalities that the energy module 11004 is configured to drive through the receptacle 11005. For example, the surgical instrument 11002 illustrated in FIG. 38 may only be configured to utilize the energy modality driven by the drive signal from the second amplifier 11016, despite the fact that the energy module 11004 is also capable of driving a second energy modality via the drive signal from the first amplifier 11014. In one particular implementation, the surgical instrument 11002 may be configured to only deliver bipolar electrosurgical energy driven by the second amplifier 11016, despite the fact that the energy module 11004 is also configured to deliver ultrasonic energy by the first amplifier 11014 through the receptacle 11005, for example. In such aspects, the surgical instrument 11002 and/or cable assembly 11006 can be configured to automatically or inherently convert the unused drive signal(s) to DC output voltage(s). In other aspects, the surgical instrument 11002 and/or cable assembly 11006 can further be configured to selectively convert the drive signal(s) generated from one or multiple amplifiers 11014, 11016 of the energy module 11004 based upon whether the surgical instrument 11002 is actively applying the particular energy modalities. For example, the surgical instrument 11002 can include a control circuit, such as a microcontroller 461 (FIG. 12), that is configured to determine whether an energy modality driven by one of the amplifiers 11014, 11016 of the energy module 11004 is actively being utilized or delivered by the surgical instrument 11002 (e.g., being applied through the end effector 11012 to therapeutically treat tissue of the patient 11100). If the energy modality is not actively being utilized by the surgical instrument 11002, the control circuit can be configured to reroute the drive signal received from the particular amplifier (e.g., the first amplifier 11014) to a rectifier (e.g., the rectifier 11008) to convert the drive signal to a DC output voltage for powering an alternative component and/or function of the surgical instrument 11002. The control circuit can be further configured to reverse the rerouting of the drive signal through the rectifier and, once again, drive the energy modality in response to sensed conditions and/or controls by the user or an external system. In this way, the surgical instrument 11002 can be configured to dynamically reroute unused energy supplied by the energy module 11004 depending on which particular energy modalities are in use at any given time.

Energy Module Electrical Grounding

In various aspects, an end user is permitted to assemble any suitable number of modules into a variety of different stacked configurations that support electrical energy flow therebetween. The modular energy system is assembled or is modified by an end user either prior to or during a surgical procedure. Since the manufacturer is not involved with the final assembly of a modular energy system, suitable precautions are taken to ensure proper electrical grounding of an assembled modular energy system and/or alignment of modules within the modular energy system.

In various aspects, accessible metal in the modular energy system is either protectively earthed or separated from live circuits to ensure user safety. This requirement is especially necessary in instances where secondary circuits are referenced to module chassis ground. Further, the protective earth connections between the modules of a modular energy system must meet the stringent International Electrotechnical Commission ("IEC") 60601 maximum impedance requirements.

In one general aspect, the present disclosure provides a grounding arrangement for a modular energy system comprising an independent bridge connector between the modules of the modular energy system and grounds that come into contact with each other prior to the bridge connection.

In another general aspect, the present disclosure provides a surgical system that comprises a first surgical module and a second surgical module. The first surgical module comprises a first enclosure comprising a bottom surface, a grounding foot extending from the bottom surface a first distance, and an insulating foot extending from the bottom surface a second distance, wherein the second distance is greater than the first distance. The second surgical module comprises a second enclosure comprising a top surface, a first receiving pocket defined in the top surface, wherein the first receiving pocket comprises a first base that is positioned a third distance from the top surface, and wherein the first receiving pocket is configured to receive the grounding foot from the first surgical module, and a second receiving pocket defined in the top surface, wherein the second receiving pocket comprises a second base that is positioned a fourth distance from the top surface, wherein the fourth distance is greater than the third distance, and wherein the second receiving pocket is configured to receive the insulating foot from the first surgical module. Further, when the grounding foot is positioned in the first receiving pocket and the insulating foot is positioned in the second receiving pocket, the grounding foot contacts the first base of the first receiving pocket and the insulating foot does not contact the second base of the second receiving pocket.

In another general aspect, the present disclosure provides a surgical system that comprises a first surgical module and a second surgical module. The first surgical module comprises a first enclosure comprising a bottom surface, a grounding foot extending from the bottom surface a first distance, and an insulating foot extending from the bottom surface a second distance, wherein the second distance is greater than the first distance. The second surgical module comprises a second enclosure comprising a top surface, a first receiving pocket defined in the top surface, wherein the first receiving pocket comprises a first base that is positioned a third distance from the top surface, and wherein the first receiving pocket is configured to receive the grounding foot from the first surgical module, and a second receiving pocket defined in the top surface, wherein the second receiving pocket comprises a second base that is positioned a fourth distance from the top surface, wherein the fourth distance is greater than the third distance, and wherein the second receiving pocket is configured to receive the insulating foot from the first surgical module. Further, when the grounding foot is positioned in the first receiving pocket and the insulating foot is positioned in the second receiving pocket, the grounding foot contacts the first base of the first receiving pocket and the insulating foot does not contact the second base of the second receiving pocket.

In another general aspect, the present disclosure provides a surgical platform that comprises a first surgical module and a second surgical module. The first surgical module is configured to be assembled in a stack configuration with the second surgical module. The first surgical module comprises a first bridge connector portion comprising first electrical connection elements and a first enclosure. The second surgical module comprises a second bridge connector portion and a metal contact attached to the outer housing. The second bridge connector portion comprises second electrical elements and an outer housing extending at least partially around the second electrical elements. The metal contact is configured to engage the enclosure of the first surgical module during assembly before the second electrical connection elements of the second bridge connector portion engage the first electrical connection elements of the first bridge connector portion.

Figure 44:
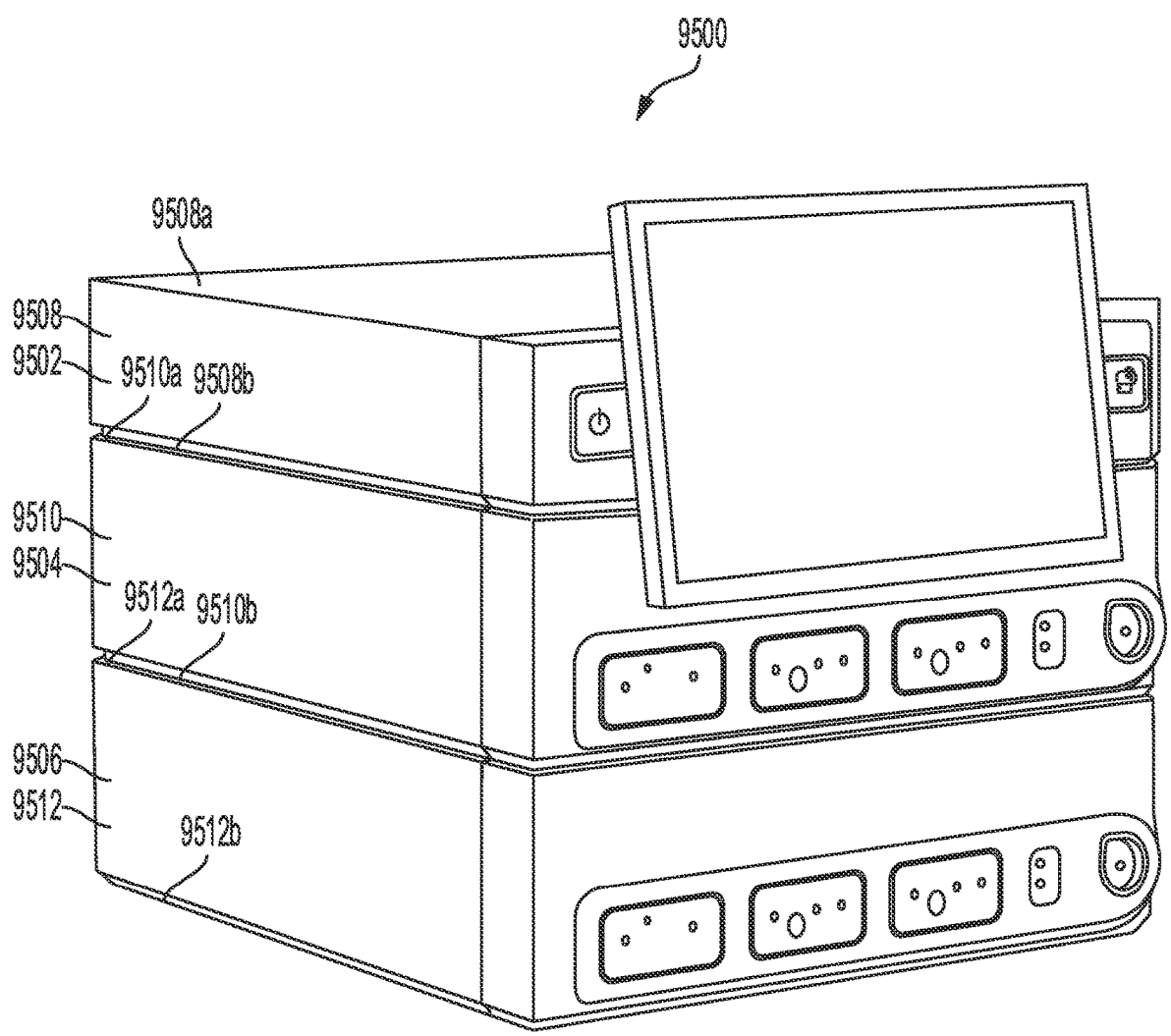
FIG. 44 is perspective view of a modular energy system, in accordance with at least one aspect of the present disclosure.

Referring to FIG. 44, three surgical modules, a first module 9502, a second module 9504, and a third module 9506, are assembled together in a stacked configuration by an end user to form a modular energy system 9500. Each module 9502, 9504, 9506, can be the same type of surgical module or different types of surgical modules. For example, each module 9502, 9504, 9506 can be a header module, an energy module, a generator module, an imaging module, a smoke evacuation module, a suction/irrigation module, a communication module, a processor module, a storage array, a surgical device coupled to a display, a non-contact sensor module, or other modular device. These and other such modules are described above under the headings SURGICAL HUBS and MODULAR ENERGY SYSTEM. As illustrated in FIG. 44, the first module 9502 is a header module, the second module 9504 is a generator module, and the third module 9506 is a generator module.

Each module 9502, 9504, 9506 can comprise an enclosure that can be made of a conductive material, such as metal. For example, the first module 9502 can comprise an enclosure 9508 comprising a top surface 9508a and a bottom surface 9508b. The second module 9504 can comprise an enclosure 9510 comprising a top surface 9510a and a bottom surface 9510b. The third module 9506 can comprise an enclosure 9512 comprising a top surface 9512a and a bottom surface 9512b. Each module 9502, 9504, 9506, can comprise secondary circuits that are referenced to module chassis ground via the respective enclosure 9508, 9510, 9512.

Each module 9502, 9504, 9506 can be configured to be assembled in a stacked configuration with an adjacent module to form the modular energy system 9500. For example, the bottom surface 9508b of the enclosure 9508 of the first module 9502 can be configured to engage the top surface 9510a of the enclosure 9510 of the second module 9504. The bottom surface 9510b of the enclosure 9510 of the second module 9504 can be configured to engage the top surface 9512a of the enclosure 9512 of the third module 9506. In various aspects, the modular energy system 9500 includes an additional surgical module or surgical modules or the modular energy system 9500 may not include one of the modules 9502, 9504, 9506.

In various aspects, to electrically ground a modular energy system, such as modular energy system 9500, multiple points of contact are established between adjacent modules to achieve a common ground. Thus, regardless of the stacked configuration of the modular energy system 9500, electrical grounding can be maintained throughout the entire modular energy system 9500. For example, an upper module stacked on top of a lower module can be grounded through the lower module in order to achieve the common ground or a lower module can be grounded through the upper module. For example, the first module 9502 can be grounded through the second module 9504 and the second module 9504 can be grounded through the third module 9506; thereby, a common ground is achieved in the modular energy system 9500. Thus, grounding of one of the modules 9502, 9504, 9506 can ground all of the modules 9502, 9504, 9506. Additionally, the multiple points of contact can facilitate efficient assembly of the stacked configuration of the modular energy system 9500 and the multiple points of contact can ensure that the modular energy system 9500 will maintain its configuration when experiencing external forces.

Figure 45A:
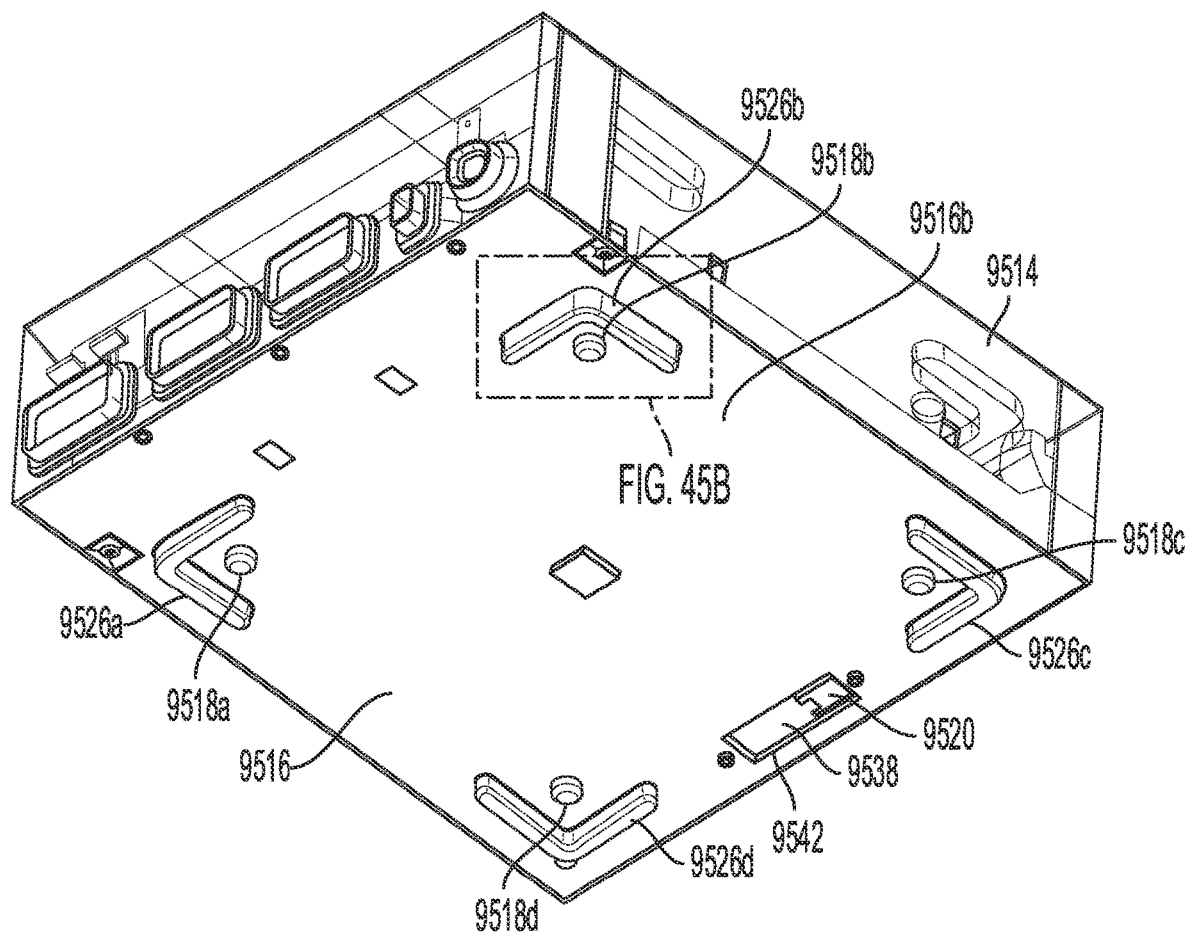
FIG. 45A is a bottom perspective view of a module of the modular energy system of FIG. 44.

Referring now to FIG. 45A, a bottom surface 9516b of an enclosure 9516 of a surgical module 9514 enclosure is shown. Module 9514 is representative of modules 9502, 9504, and 9506. The bottom surface 9516b of the enclosure 9516 can include one or more grounding features, such as, for example, two or more grounding features, three or more ground features, or four or more ground features. For example, as illustrated, the bottom surface 9516b can comprise four grounding features 9518a-d sized and spaced apart, such that the grounding features 9518a-d may engage grounding features of a separate module, thus providing direct contact between the modules at multiple points. The contact can ensure that a common ground is achieved between modules and that the module 9514 can maintain its position relative to a mating module when experiencing external forces.

The bottom surface 9516b of the enclosure 9516 comprises an opening 9542 that is shaped and configured to mount a bridge connector portion 9520 (e.g., a female bridge connector portion). The bridge connector portion 9520 includes a recess 9538 that is shaped and configured to receive a bridge connector portion (e.g., male bridge connector portion) from a separate module.

Figure 46:
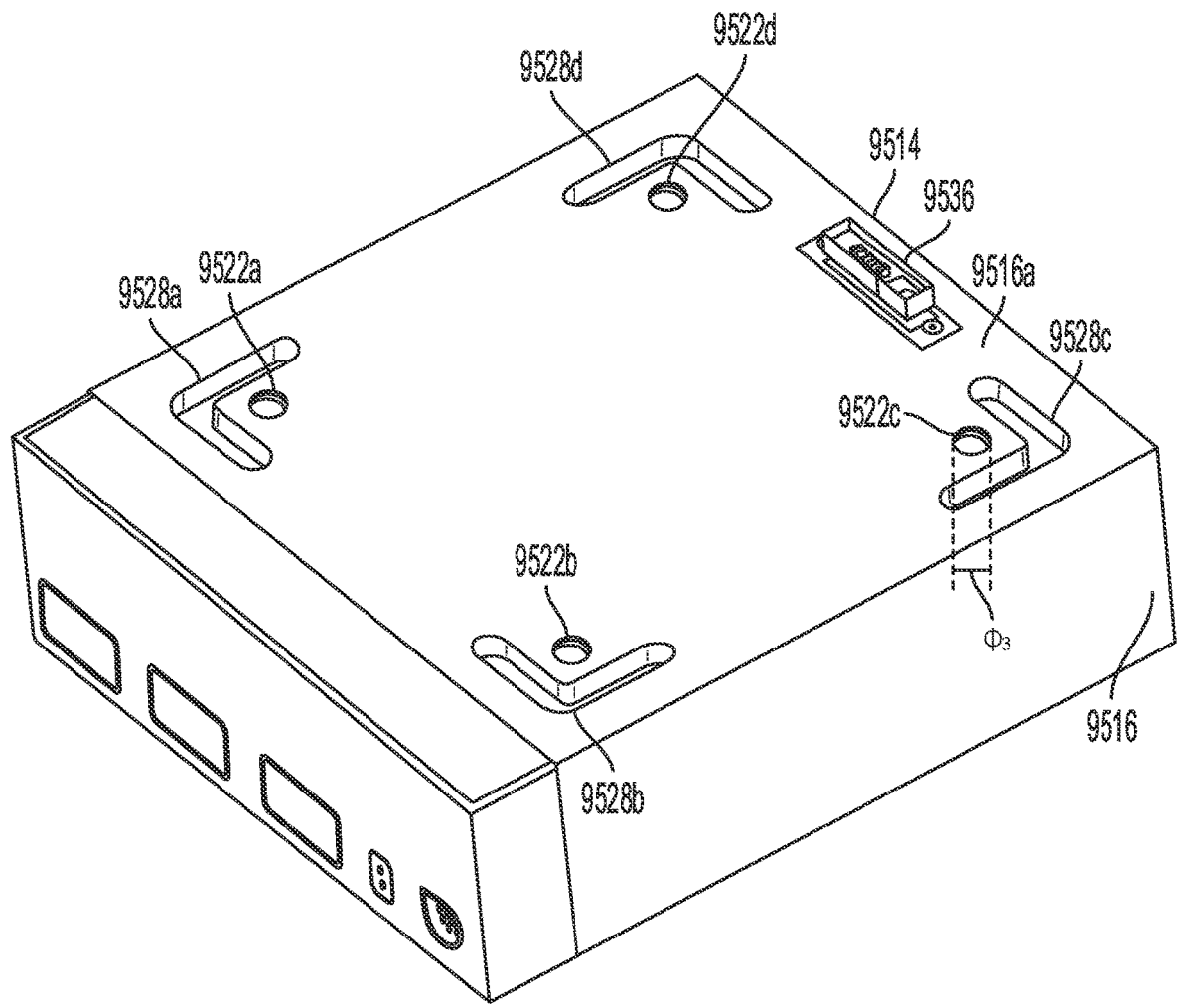
FIG. 46 is a top perspective view of a module of the modular energy system of FIG. 44.

Referring now to FIG. 46, a top surface 9516a of the enclosure 9516 of the module 9514 is shown. The top surface 9516a of the enclosure 9516 can include one or more grounding features, such as, for example, two or more grounding features, three or more grounding features, or four or more grounding features. For example, as illustrated, the top surface 9516a can comprise four grounding features 9522a-d. The grounding features 9522a-d on the top surface 9516a are sized and spaced apart such that the grounding features 9522a-d may engage grounding features of a separate module, thus providing direct contact between the modules at multiple points. The contact can ensure that a common ground is achieved between the modules and that the module 9514 can maintain its position relative to the mating module when experiencing external forces.

A bridge connector portion 9536 (e.g., a male bridge connector portion) is mounted to the top surface 9516a of the enclosure 9516 of the module 9514 and extends away from the module 9514. When an upper module is stacked on top of the module 9514, the bridge connector portion of the module 9514 is inserted into the recess of a female bridge connector portion of the upper surgical module, thereby establishing electrical and/or signal communication between the modules and/or alignment between the modules. In an alternative configuration where a male bridge connector portion is on the bottom surface of an upper module and the female connector portion is on the top surface of a lower module, when the upper module is stacked on top of the lower module, the male bridge connector portion of the upper module is inserted into the recess of the female bridge connector portion of the lower module, thereby establishing electrical and/or signal communication between the modules and/or alignment between the modules.

Figure 49:
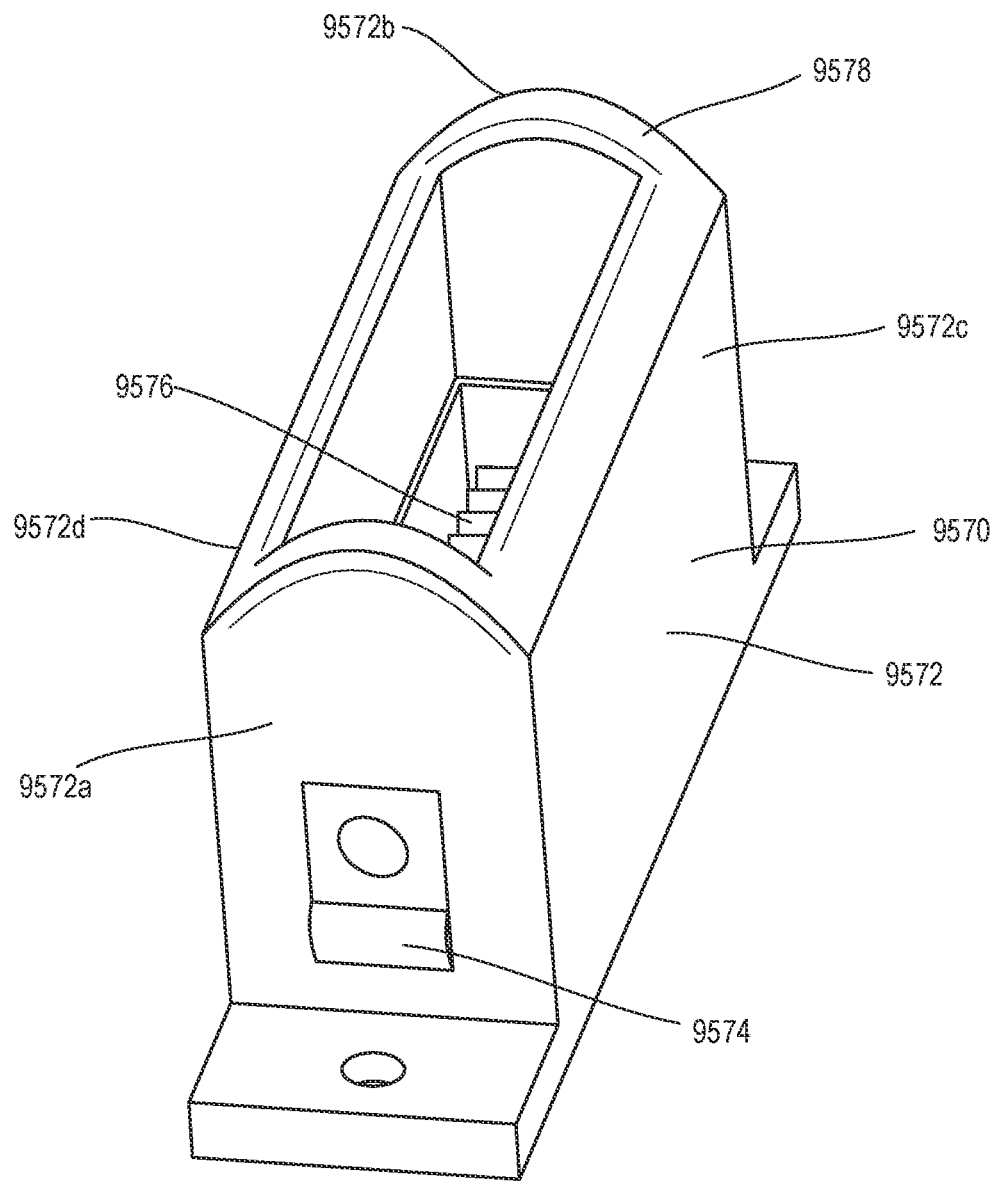
FIG. 49 illustrates a male bridge connector portion comprising a grounding feature of a modular surgical module, in accordance with at least one aspect of the present disclosure.

In various aspects, the bridge connector portion 9536 can comprise a grounding feature configured to achieve a common ground between modules. For example, referring to FIG. 49, a male bridge connector portion 9570, including a grounding feature 9574 attached to an outer housing 9572 of the male bridge connector portion 9570, is shown. The outer housing 9572 extends at least partially around the electrical connection elements 9576. The outer housing 9572 is rectangular and rounded along the length of the outer housing 9572. The outer housing 9572 includes rounded or curved-top faces 9578 that allow male and female bridge connector portions to align even when modules are at a difficult angle with another. In other words, the outer housing 9572 is shaped and/or sized to guide the electrical connection elements 9576 and grounding feature 9574 into a properly aligned engagement with a female bridge connector. The grounding feature 9574 is attached to a first side 9572a of the outer housing 9572 and is in electrical communication with an enclosure of a respective module and/or a ground of the respective module. In various aspects, another grounding feature (not shown) is attached to the second side 9572*b* of the outer housing 9572 and is in electrical communication with the enclosure of the respective module and/or the ground of the respective module. In various aspects, the first side 9572*a* and the second side 9572*b* are shorter than a third side 9572*c* and a fourth side 9572*d* of the outer housing 9572. The grounding feature 9574 can comprise a metal contact, such as, for example, a springing contact.

When an upper module is stacked on top of a lower module comprising the male bridge connector portion 9570 on a top surface of the lower module, the male bridge connector portion 9570 is inserted into the recess of a female bridge connector on the bottom surface of the upper surgical module. Upon insertion, the grounding feature 9574 can engage the enclosure of the upper surgical module. For example, the male bridge connector portion 9570 can be inserted into the recess 9538 of the module 9514 in FIG. 45A. Upon insertion, the grounding feature 9574 can directly contact the enclosure 9516 near the opening 9542 thereby achieving a common ground between a surgical module comprising the male bridge connector portion 9570 and the module 9514.

Further, the outer housing 9572 of the male bridge connector portion 9570 is shaped and/or sized to guide the grounding feature 9574 into direct contact with the enclosure of a separate module. In aspects where the grounding feature 9574 is a springing contact, the springing contact is transitioned into a biased configuration responsive to direct contact with the enclosure of the separate module. The springing contact can ensure that a proper common ground is achieved between modules.

Further, the grounding feature 9574 can be configured to engage the enclosure of a separate module during assembly before the electrical connection elements 9576 of the male bridge connector portion 9570 engage electrical connection elements of a bridge connector portion on the separate module. That is, the grounding feature 9574 can be positioned on the outer housing 9572 relative to the electrical connection elements 9576 such that the grounding feature 9574 will engage the enclosure of the separate module during assembly before the electrical connection elements 9576 of the male bridge connector portion 9570 engage the electrical elements of a bridge connector portion on the separate module. Therefore, a common ground can be achieved between modules prior to engagement of the bridge connector portions that can ensure user safety.

In addition to the grounding feature 9574 or alternatively to the grounding feature 9574, direct contact between the grounding features on a top surface of an enclosure of a lower module and the grounding features on the bottom surface of an enclosure of an upper module stacked on top of the lower module function to ground the upper module to the lower module, thereby providing multiple points of contact to maintain a path of least resistance (e.g., electrical resistance between modules). When the upper module is stacked on top of a lower module, the weight of the upper module maintains the grounding features on bottom surface of the upper module in electrical communication with the grounding features on the top surface of the lower module.

Furthermore, the grounding features 9518*a-d* and 9522*a-d* of the module 9514 can be arranged in a spread configuration to maintain a path of least resistance between surgical modules in the stacked configuration. For example, the grounding features 9518*a-d* can be spaced apart near the four corners of the bottom surface 9516*b* of the enclosure 9516 and the ground features 9522*a-d* can be spaced apart near the four corners of the top surface 9516*a* of the enclosure 9516. That is, the bottom surface 9516*b* can comprise one of grounding features 9518*a-d* at each corner, and the top surface 9516*a* can comprise one of grounding features 9522*a-d* at each corner. The positions of the grounding features 9518*a-d* on the bottom surface 9516*b* can mirror the positions of the grounding features 9522*a-d* on the top surface 9516*a*, thereby providing stability to the stacked configuration.

The grounding features 9518*a-d* and 9522*a-d* can be molded into the enclosure 9516, or the grounding features 9518*a-d* and 9522*a-d* can be fastened to the enclosure. For example, the grounding features 9518*a-d* and 9522*a-d* can be at least one of a receiving pocket molded in the enclosure 9516, a grounding foot molded in the enclosure 9516, a conductive pin fastened to the enclosure 9516, or a conductive socket fastened to the enclosure 9516.

In various aspects, the grounding features 9518*a-d* extend away from the bottom surface 9516*b* of the enclosure 9516 and the module 9514 (e.g., form grounding feet) and are sized and spaced apart such that the grounding features 9518*a-d* may be received by receiving pockets of a separate module, thus providing direct contact between the modules in four distinct places. Further, in various aspects, the grounding features 9522*a-d* are configured as receiving pockets and are sized and spaced apart such that grounding feet of a separate surgical module can be seated into the grounding features 9522*a-d*, thus providing direct contact between the surgical modules in four distinct places. The direct contact can achieve a common ground, provide a path of least resistance, and maintain position of the module 9514 when experiencing external forces.

Figure 45B:
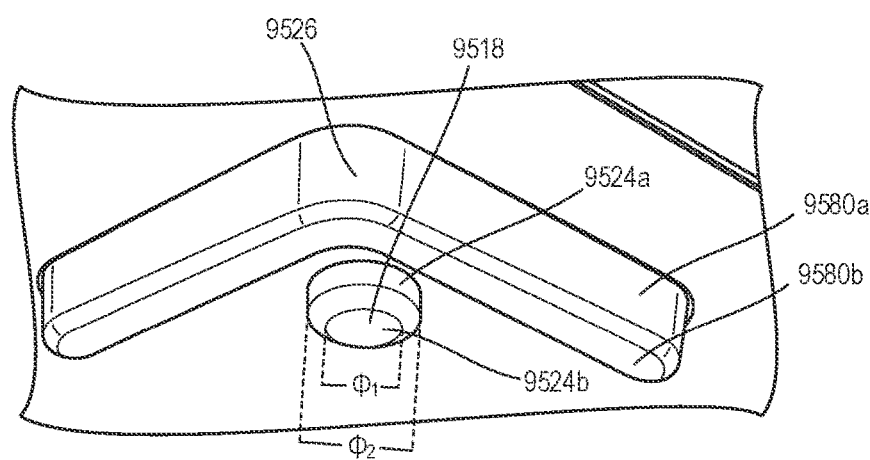
FIG. 45B is a close-up of the module of FIG. 45A.

The grounding features 9518*a-d* can have various shapes, such as, for example, circular, as illustrated in FIGS. 45A-B. A detailed view of a single grounding feature 9518 of grounding features 9518*a-d* can be seen in FIG. 45B. A base portion 9524*a* of the grounding feature 9518 can have a first diameter, $\phi_1$. The grounding feature 9518 can taper inwardly from the base portion 9524*a* to form a seating portion 9524*b* of the grounding feature 9518. The taper can facilitate alignment of the modules during assembly. The seating portion 9524*b* can have a second diameter, $\phi_2$, which is smaller than the first diameter, $\phi_1$, of the base portion 9524*a*. The seating portion 9524*b* can be configured to be seated in a receiving pocket of a top surface of an enclosure of a separate module.

Similarly, the grounding features 9522*a-d* can have various shapes, such as, for example, circular, as illustrated in FIG. 46. The grounding features 9522*a-d* can each comprise a third diameter, $\phi_3$, near the top surface 9516*a*, which can be sized to receive grounding feet on a bottom surface of an enclosure of a separate module and/or engage conductive posts on the bottom surface. For example, the third diameter, $\phi_3$, of the grounding features 9522*a-d* can be larger than the second diameter, $\phi_2$, of the seating portion 9524*b* of the grounding features 9518*a-d*. It is contemplated that the grounding features 9518*a-d* and 9522*a-d* can be of other shapes and sizes.

In aspects comprising grounding feet extending from the bottom surface of a module, the arrangement of the grounding features can leave the grounding features of the lowest/bottom module in a stacked arrangement of a modular energy system without corresponding receiving pockets in a separate module. One possible, albeit expensive, solution is to especially design a module to function as the lowest/bottom module in the stacked configuration of the modular energy system. However, an end user may mistakenly attempt to assemble this especially designed module in an intermediate position in the stacked configuration of the modular energy system, potentially leaving the grounding features of lowest/bottom module in the stacked configuration exposed. Moreover, when a series of modules are assembled together to form the stacked configuration of the modular energy system, it is envisioned that the stacked modular energy system is rested upon a flat surface, such as, for example, a cart, a table, or the like. Positioning the grounding features against such flat surfaces can be problematic. Further, it is desirable that any module from the stacked modular energy system be capable of being positioned in the lowest/bottom position in the stacked configuration without having to worry about achieving a specific arrangement of the modular energy system. Enabling agnostic positioning of the modules can facilitate ease of assembly of the modular energy system.

FIGS. 45A-B and 46 present a solution to the above-raised issues that account for when a surgical module is positioned on the lowest/bottom position (e.g., the third module 9506 in FIG. 44) in the stacked configuration of the modular energy system 9500 and rests on a flat surface. In various aspects, the bottom surface 9516b of the enclosure 9516 further includes an insulated foot or insulated feet. For example, referring again to FIG. 45A, the bottom surface 9516b includes four insulated feet 9526a-d extending from the bottom surface 9516b of the enclosure 9516. The insulated feet 9526a-d are configured to electrically isolate the enclosure 9516 from the flat surface and/or maintain position of the module 9514 relative to the flat surface when experiencing external forces. The grounding features 9518a-d extend from the bottom surface 9516b of the enclosure 9516 a first distance, $d_1$, and the insulated feet 9526a-d extend from the bottom surface 9516b of the enclosure 9516 a second distance, $d_2$, such that when the module 9514 is positioned on the lowest/bottom position in the stacked configuration of the modular energy system 9500, the grounding features 9518a-d do not rest on the flat surface. The insulated feet 9526a-d rest on the flat surface and can prevent the grounding features 9518a-d from engaging the flat surface.

The insulated feet 9526a-d can electrically isolate the enclosure 9516 from the flat surface. For example, the insulated feet 9526a-d can comprise an insulating material, such as rubber. It is contemplated that other insulating materials can be utilized to form the insulating feet 9526a-d. Additionally, the material of the insulated feet 9526a-d can be selected to create friction between the module 9514 and the flat surface in order to maintain the position of the module 9514 relative to the flat surface when experiencing external forces.

The insulated feet 9526a-d can be spaced apart in a spread configuration to provide stability to the module 9514 and/or surgical modules stacked on top of the module 9514. For example, the insulated feet 9526a-d can be spaced apart near the four corners of the bottom surface 9516b of the enclosure 9516. For example, one insulated foot of the insulated feet 9526a-d can be positioned in each corner of the bottom surface 9516b. The quantity of insulated feet 9526a-d can correspond to the quantity of grounding features 9518a-d.

The insulated feet 9526a-d can have various shapes, such as, for example, as illustrated in FIGS. 45A-B. The insulated foot 9526 can taper inwardly from a base portion 9580a to form a seating portion 9580b of the insulated foot 9526. The taper can facilitate alignment of the modules during assembly. The seating portion 9580b can be configured to be seated in a receiving pocket of a top surface of an enclosure of a separate module.

Each insulated foot 9526a-d can be configured in an "L" shape. For example, in FIG. 45B, the "L" shaped configuration of a single insulated foot 9526 of the insulated feet 9526a-d is shown. Referring to back FIG. 45A, the "L" shape configuration of the insulated feet 9526a-d can provide mechanical stability when the module 9514 is placed on top of the flat surface, ensuring that the module 9514 will maintain its position when experiencing external forces. It is contemplated that the insulated feet 9526a-d can be of other shapes and sizes.

In various aspects, the top surface 9516a of the enclosure 9516 further includes one or more receiving pockets sized and configured for receiving an insulated foot or insulated feet of a separate surgical module, such that the grounding features of the respective modules can directly contact to achieve a common ground. For example, referring again to FIG. 46, the top surface 9516a of the enclosure 9516 includes four insulated feet receiving pockets 9528a-d. The receiving pockets 9528a-d can be spaced apart in a spread configuration to align the module 9514 with the separate module. For example, the receiving pockets 9528a-d are spaced apart such that the insulated feet of a separate module will be positioned within the receiving pockets 9528a-d when the separate module is stacked on top of the module 9514. As illustrated in FIG. 46, the receiving pockets 9528a-d are spaced apart near the four corners of the top surface 9516a of the enclosure 9516. For example, one of the receiving pockets 9528a-d is positioned in each corner of the top surface 9516a of the enclosure 9516. The receiving pockets 9528a-d are sized and configured to receive insulated feet of a separate module.

The receiving pockets of the grounding features 9522a-d of the top surface 9516a of the module can each include a base that is positioned a third distance, $d_3$, from the top surface 9516a. In various aspects, the third distance, $d_3$, is less than or equal to the first distance, $d_1$, such that grounding feet of a separate module can contact the base of the receiving pockets of the grounding features 9522a-d. The receiving pockets 9528a-d each include a base that is positioned a fourth distance, $d_4$, from the top surface 9516a. In various aspects, the fourth distance, $d_4$, is greater than the second distance, $d_2$, such that the insulated feet of a separate module can be received by the receiving pockets 9528a-d.

Figure 47:
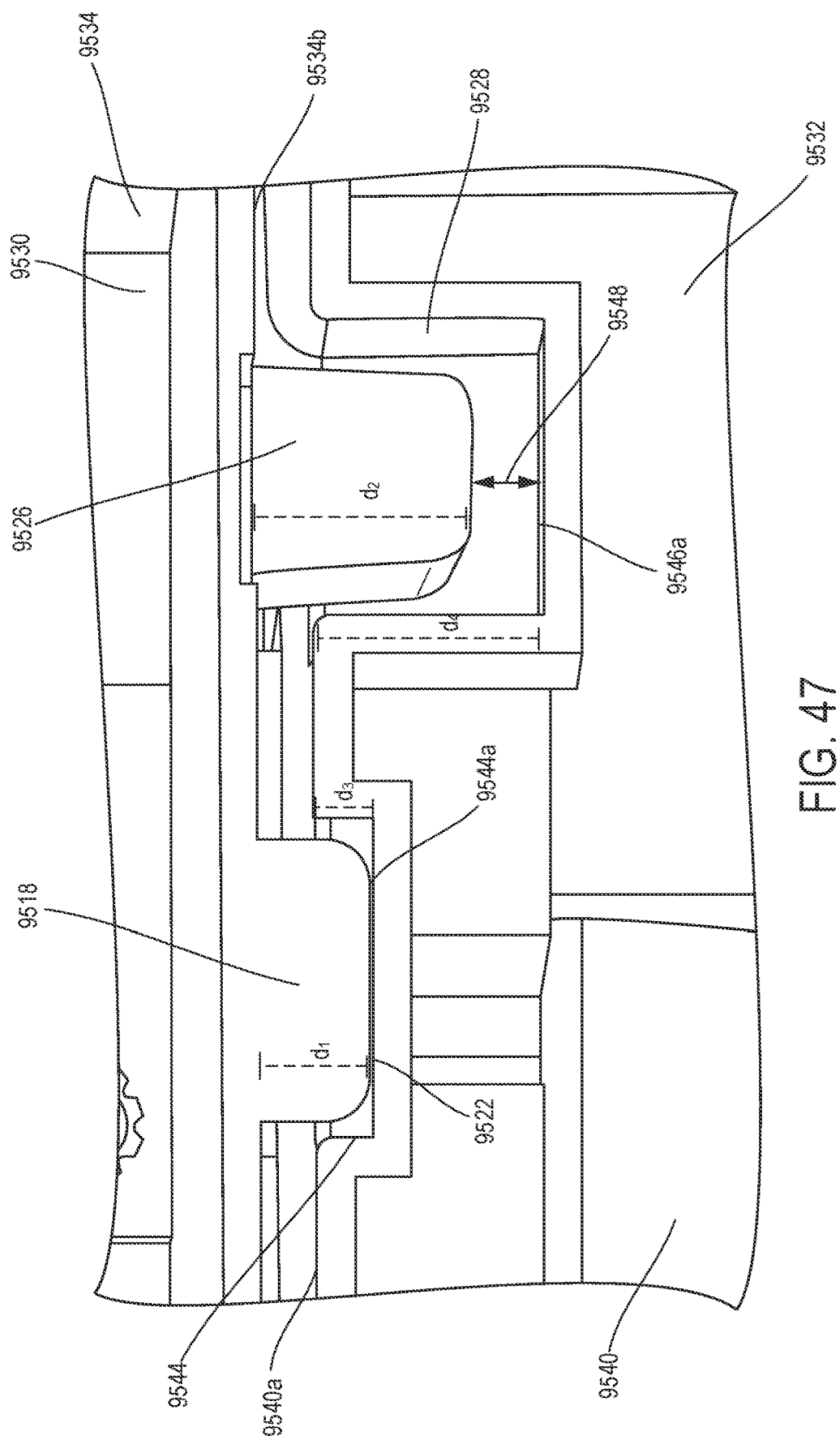
FIG. 47 is a cross-sectional view of an upper module seated onto a lower module of a modular energy system, in accordance with at least one aspect of the present disclosure.

FIG. 47 illustrates a cutaway view of a portion of an upper surgical module 9530 stacked on top of a lower surgical module 9532. The upper module 9530 and the lower module 9532 can be the same type of module or different types of modules. An insulated foot 9526 representative of insulated feet 9526a-d, a grounding feature 9518 representative of the grounding features 9518a-d, a grounding feature 9522 representative of grounding features 9522a-d, and an insulated foot receiving pocket 9528 representative of receiving pockets 9528a-d are shown in FIG. 47. The upper module 9530 includes the grounding feature 9518 and the insulated foot 9526 extending from the bottom surface 9534b of the enclosure 9534 of the upper module 9530. The grounding feature 9518 extends from the bottom surface 9534b of the enclosure 9534 of the upper module 9530 a first distance, $d_1$, while the insulated foot 9526 extends from the bottom surface 9534b of the enclosure 9534 of the upper module 9530 a second distance, $d_2$. The second distance, $d_2$, is greater than the first distance, $d_1$. Therefore, if the upper module 9530 is set on a flat surface, the insulated foot 9526 may contact the flat surface prior to the grounding feature 9518 and can prevent the grounding feature 9518 from contacting the flat surface.

The lower module 9532 includes the grounding feature 9522 and the insulated foot receiving pocket 9528 on a top surface 9540*a* of an enclosure 9540 of the lower module 9532. The grounding feature 9522 comprises a grounding feature receiving pocket 9544 defined in the top surface 9540*a*. The receiving pocket 9544 is sized and configured to receive the grounding feature 9518 of the upper module 9530. The receiving pocket 9544 includes a base 9544*a* that is positioned a third distance, $d_3$, from the top surface 9540*a*. In various aspects, the third distance, $d_3$, is less than or equal to the first distance, $d_1$.

The receiving pocket 9528 is defined in the top surface 9540*a* of the enclosure 9540 of the lower module 9532. The receiving pocket 9528 is sized and configured to receive the insulated foot 9526 of the upper module 9530. The receiving pocket 9528 includes a base 9546*a* that is positioned a fourth distance, $d_4$, from the top surface 9540*a*. As illustrated, the fourth distance, $d_4$, is greater than the second distance, $d_2$.

Owing to the size and configuration of the grounding feature 9518, insulated foot 9526, the grounding feature 9522, and the receiving pocket 9528, when the upper module 9530 is stacked on top of the lower module 9532, the grounding feature 9518 is seated in the receiving pocket 9544 of the ground feature 9522 such that the grounding feature 9518 makes direct contact with the base 9544*a* of the receiving pocket 9544. While the grounding feature 9518 makes direct contact with the base 9544*a*, the insulated foot 9526 does not make contact with the base 9546*a* of the receiving pocket 9528 and a clearance 9548 is defined between the insulated foot 9526 and the base 9546*a* of the receiving pocket 9528. Thus, the grounding features 9518 and 9522 are in direct contact with each other and a common ground is achieved.

Figure 50:
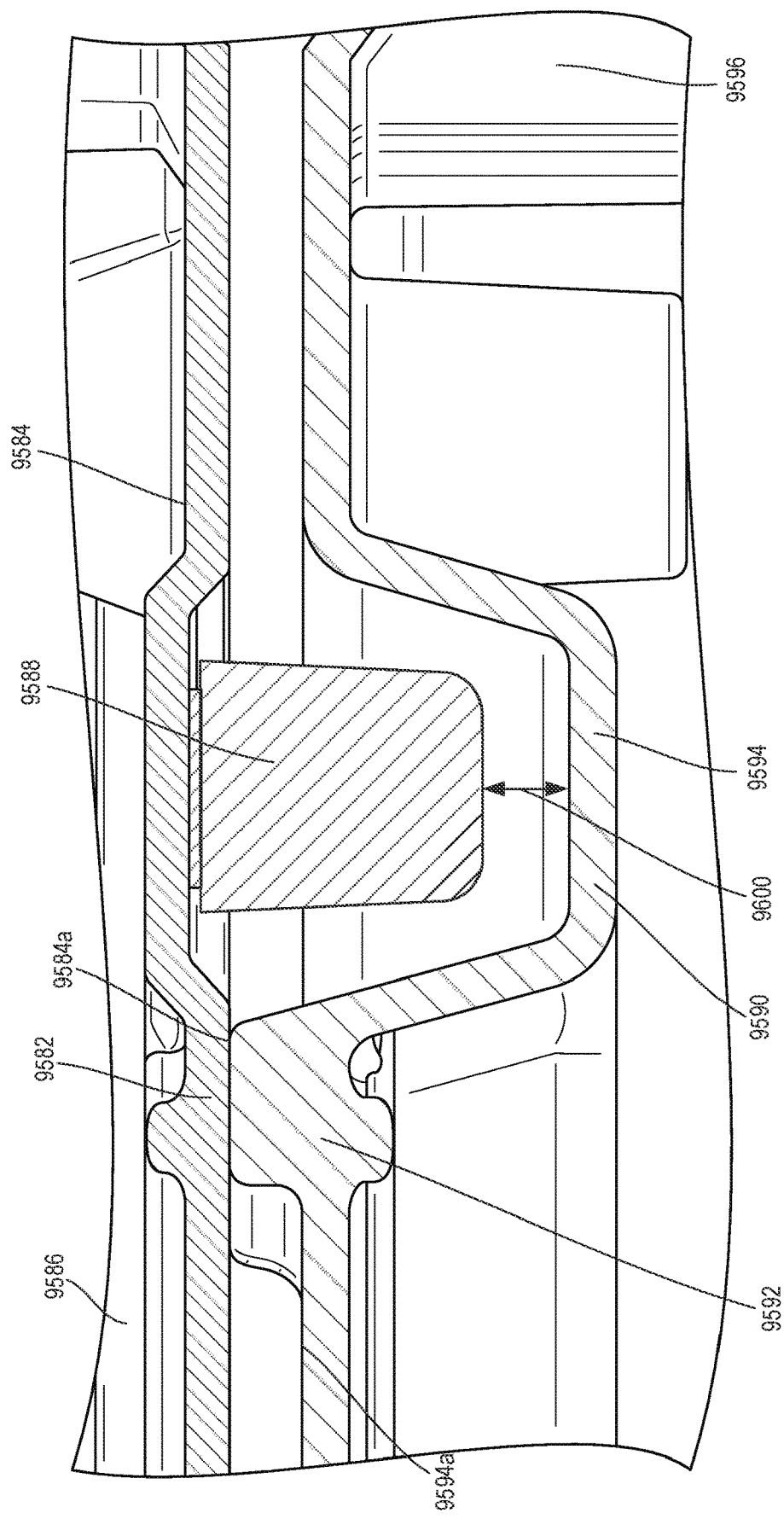
FIG. 50 is a cross-sectional view of an upper module seated onto a lower module of a modular energy system, in accordance with at least one aspect of the present disclosure.

In an alternative configuration, referring to FIG. 50, a grounding feature 9592 can extend away from a top surface 9594*a* of an enclosure 9594 of a module 9596 (e.g., form grounding feet). Further, in various aspects, a grounding feature 9582 of a bottom surface 9584*a* of an enclosure 9584 of a separate module 9586 can be configured as a receiving surface, which is sized such that grounding feet of a separate surgical module can be seated onto or otherwise in contact with the grounding features 9592, thus providing direct contact between the surgical modules. The grounding feature 9592 can be a substantially planar surface and may not protrude from the bottom surface 9584*a* of the enclosure 9584. The module 9596 can comprise a receiving pocket 9590 defined in the top surface 9594*a* that is sized and configured to receive the insulated foot 9588 of the module 9586. While the grounding feature 9582 makes direct contact with the grounding feature 9592, the insulated foot 9588 does not make contact with the receiving pocket 9590 and a clearance 9600 is defined between the insulated foot 9588 and the receiving pocket 9590.

Accordingly, when an upper module is stacked on top of a lower module to form a stack configuration, the grounding features of the upper module are in direct contact with the grounding features of the lower module and the insulated feet of the upper module are floating in the receiving pockets of the lower module, thereby defining a clearance therebetween. When the lower surgical module is removed from the stack configuration and the upper module is to be positioned on a flat surface, the insulated feet of the upper module make direct contact with the flat surface, while the grounding features of the upper module do not make contact with the flat surface, owing to the insulated feet extending a greater distance from the bottom surface of the enclosure of the upper module than the grounding features.

The above described configuration allows each module to have identical grounding features, insulated feet, and receiving pockets, regardless of the position of the module within the stacked arrangement of a modular energy system, thereby enabling efficient assembly of the modular energy system 9500.

Figure 48A:
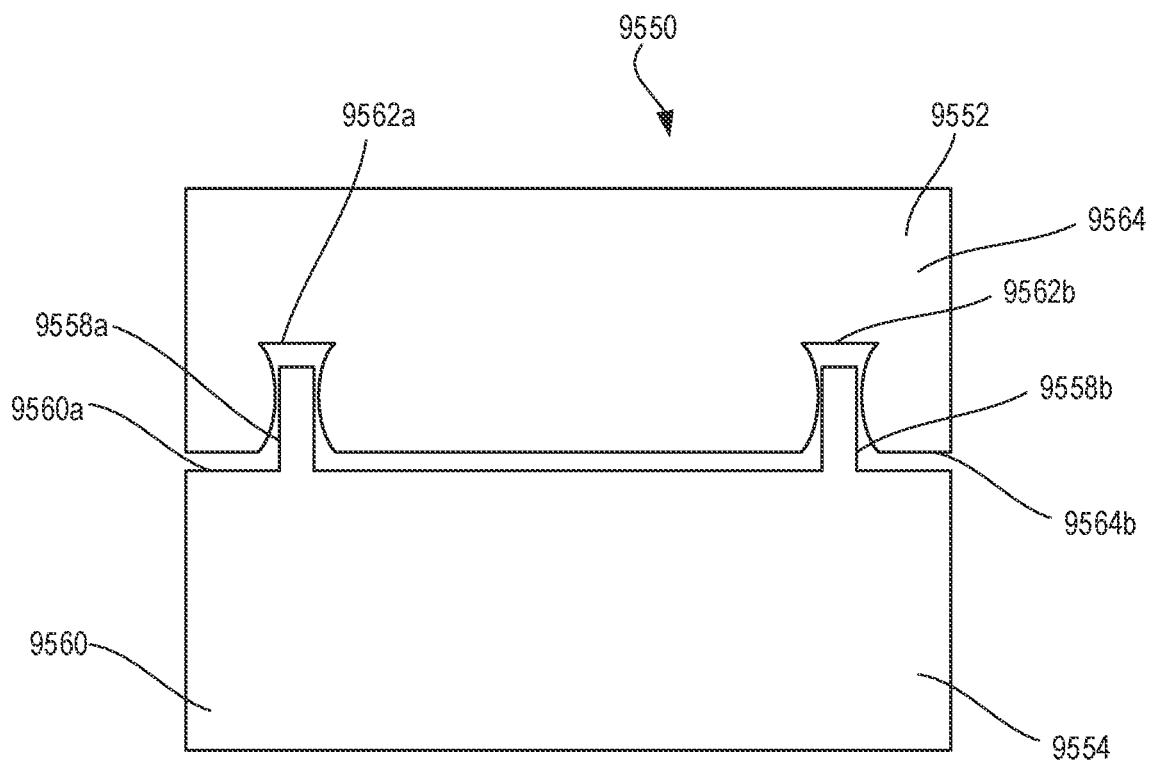
FIG. 48A illustrates an upper module and a lower module of a modular energy system in an assembled configuration, in accordance with at least one aspect of the present disclosure.
Figure 48B:
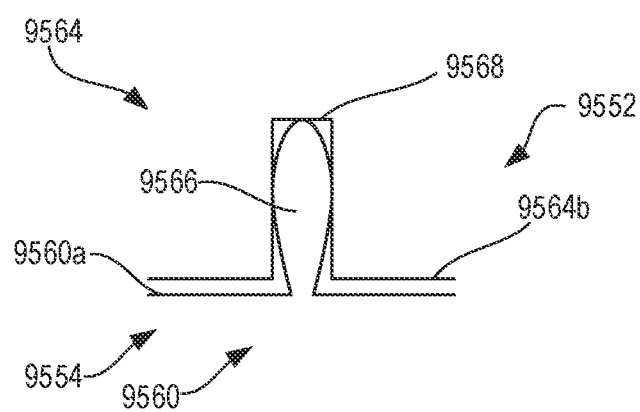
FIG. 48B illustrates a post/socket configuration for connecting an upper module and a lower module of a modular energy system, in accordance with at least one aspect of the present disclosure.

Referring to FIGS. 48A and 48B, an upper surgical module 9552 and a lower surgical module 9554 in a stack configuration of a portion of a modular energy system 9550 are shown. The upper module 9552 and the lower module 9554 can be the same type of module or different types of modules.

As illustrated in FIG. 48A, two grounding features 9558*a-b* of the lower module 9554 are shown. Each grounding feature 9558*a-b* can individually be configured as a conductive post or a conductive socket. As illustrated, the grounding features 9558*a-b* are configured as conductive posts extending from a top surface 9560*a* of an enclosure 9560 of the of the lower module 9554. In various aspects, conductive posts 9558*a-b* can be integrated into the enclosure 9560 of the lower module 9554 or the conductive posts 9558*a-b* can be fastened to the enclosure 9560 of the lower module 9554. For example, the conductive posts 9558*a-b* can be fastened to the enclosure 9560 of the lower module 9554 with nuts and/or with or without lock washers.

Two grounding features 9562*a-b* of the upper module 9552 are shown. Each grounding feature 9562*a-b* can be individually configured as a conductive post or a conductive socket. As illustrated, the grounding features 9562*a-b* are configured as conductive sockets defined in a bottom surface 9564*b* of an enclosure 9564 of the upper module 9552. When the upper and lower modules 9552, 9554 are in a stacked configuration, the conductive posts 9558*a-b* of the lower module 9554 can be retained in the corresponding conductive socket 9562*a-b* of the upper module 9552.

The post/socket configuration of the modules 9552, 9554 can improve alignment between the modules. For example, the grounding features 9558*a-b* can be sized and configured to engage the grounding features 9562*a-b* prior to engagement of a bottom bridge connector portion (not shown) of the upper module 9552 (e.g., bridge connector portion 9520 in FIG. 45A) and a top bridge connector portion (not shown) of the lower module 9554 (e.g., bridge connector portion 9536 in FIG. 46) such that proper alignment of the bridge connector portions is achieved during assembly of the modules 9552, 9554 into a stacked configuration. In various aspects, it may desirable to achieve a common ground between adjacent modules prior to engagement of the respective bridge connector portions of the adjacent modules to ensure user safety. Thus, the grounding features 9558*a-b* and 9562*a-b* can be configured to engage each other prior to the respective bridge connector portions.

In various aspects, as illustrated in FIG. 48A, the post/socket configuration can be implemented with rigid conductive posts 9558*a-b* on the lower module 9554 and springing conductive sockets 9562*a-b* on the upper module 9552 that are transitioned into a biased configuration upon receiving their corresponding posts 9588-*b*. Alternatively, as illustrated in FIG. 48B, the post/socket configuration can be implemented with a springing post 9566 on the lower module 9554 and a rigid socket 9568 on the upper module 9552. The springing sockets and/or springing posts can ensure that a proper common ground is achieved between the surgical modules 9552, 9554. A springing post can be a spring-loaded connector and a springing socket can be a spring-loaded socket connector.

Enemy Module Bridge Connector

In various aspects, an end user is permitted to assemble any suitable number of modules into a variety of different stacked configurations that support electrical energy flow therebetween. Each of the different types of modules provides different functionality, thereby allowing individuals to customize the functions provided by each surgical platform by customizing the modules that are included in each surgical platform. The modular energy system is assembled or is modified by an end user either prior to or during a surgical procedure. Since the manufacturer is not involved with the final assembly of a modular energy system, suitable precautions are taken to ensure proper stacking of an assembled modular energy system and/or alignment of modules within the modular energy system.

As discussed above, the one or more modules can be connected together in a variety of different stacked configurations to form various modular energy systems. When positioned in the variety of different stacked configurations, the surgical modules are configured to communicate and transmit power therebetween. It is contemplated that external wiring connections can be utilized in order to electrically couple the modules when stacked together to facilitate the transmission of communication signals and power. However, it is desirable that the modules be connectable together without the need for external wiring to facilitate safe assembly and disassembly by an end user. To that end, the modules can include bridge connectors that are configured to transmit power and/or communication signals between the modules in the modular energy system when the modules are assembled or engaged together.

In one general aspect, the present disclosure provides a connector positioned on the top and a socket on the bottom of a stackable energy module, which can carry communication and power through multiple units (i.e., modules). The connector shape facilitates mechanical alignment, then grounding, then electrical contact of a series of power and communication lines when multiple energy modules are assembled together into a modular energy system.

In another general aspect, the present disclosure provides a bridge circuit that is segmented into identical boards residing within each module and is connected by connectors shaped to align and connect a variable number of stacked modules together (including a header module).

In another general aspect, the present disclosure provides a module connector configured to have a first or stowed configuration and second or extended configuration. The modular connectors for energy modules (and/or other modules of a modular energy system) can carry both communication and power between modules, where the connector is configured to be transitioned between the stowed configuration, which has a first low profile, and the extended configuration, which provides for both an electrical and mechanical connection between modules.

In yet another general aspect, the present disclosure provides a surgical platform comprising a first surgical module and a second surgical module. The first surgical module is configured to be assembled in a stack configuration with the second surgical module. The first surgical module includes a first bridge connector portion, which comprises a first outer housing and first electrical connection elements. The second surgical module comprises a second bridge connector portion, which comprises a second outer housing and second electrical connection elements. The second outer housing is shaped and configured to engage the first outer housing during the assembly before second electrical connection elements engage the first electrical connection elements.

In yet another general aspect, the present disclosure provides a surgical platform comprising a first surgical module and a second surgical module. The first surgical module comprises a first enclosure comprising a bottom surface, a first bridge connector, wherein the first bridge connector comprises a recess, a first printed circuit board (PCB), and a first wire assembly connected to the first PCB. The first wire assembly extends from the first PCB to the first bridge connector and the first wire assembly is operably coupled to the first bridge connector. The second surgical module comprises a second enclosure comprising a top surface, a second bridge connector, a second PCB, and a second wire assembly connected to the second PCB. The second bridge connector extends away from the top surface and the second bridge connector is configured to be positioned in the recess of the first bridge connector of the first surgical module. The second wire assembly extends from the second PCB to the second bridge connector and the second wire assembly is operably coupled to the second bridge connector. When the second bridge connector is positioned in the first bridge connector, the second wire assembly is electrically coupled with the first wire assembly.

Figure 51:
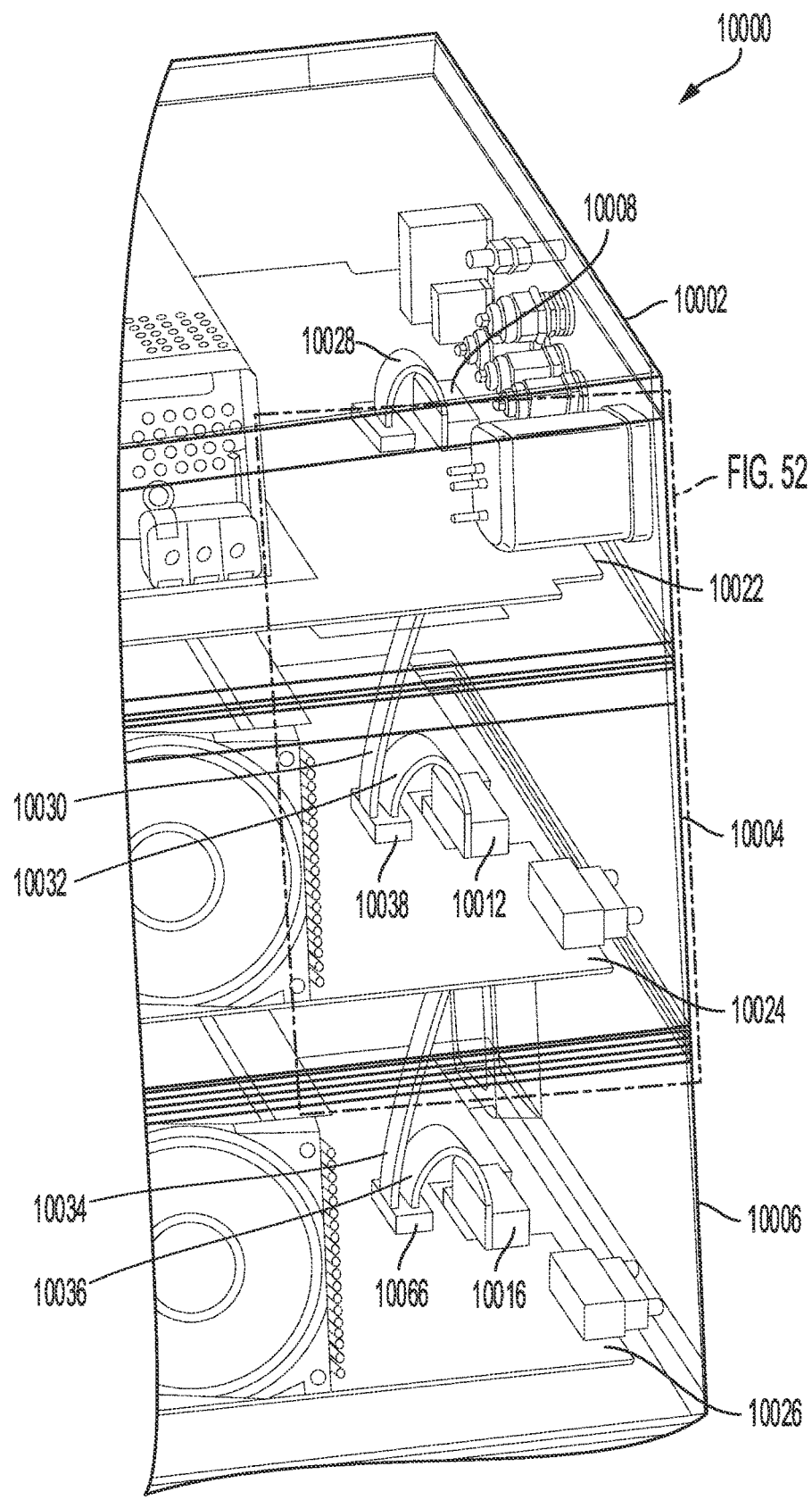
FIG. 51 illustrates a modular energy system, in accordance with at least one aspect of the present disclosure.
Figure 52:
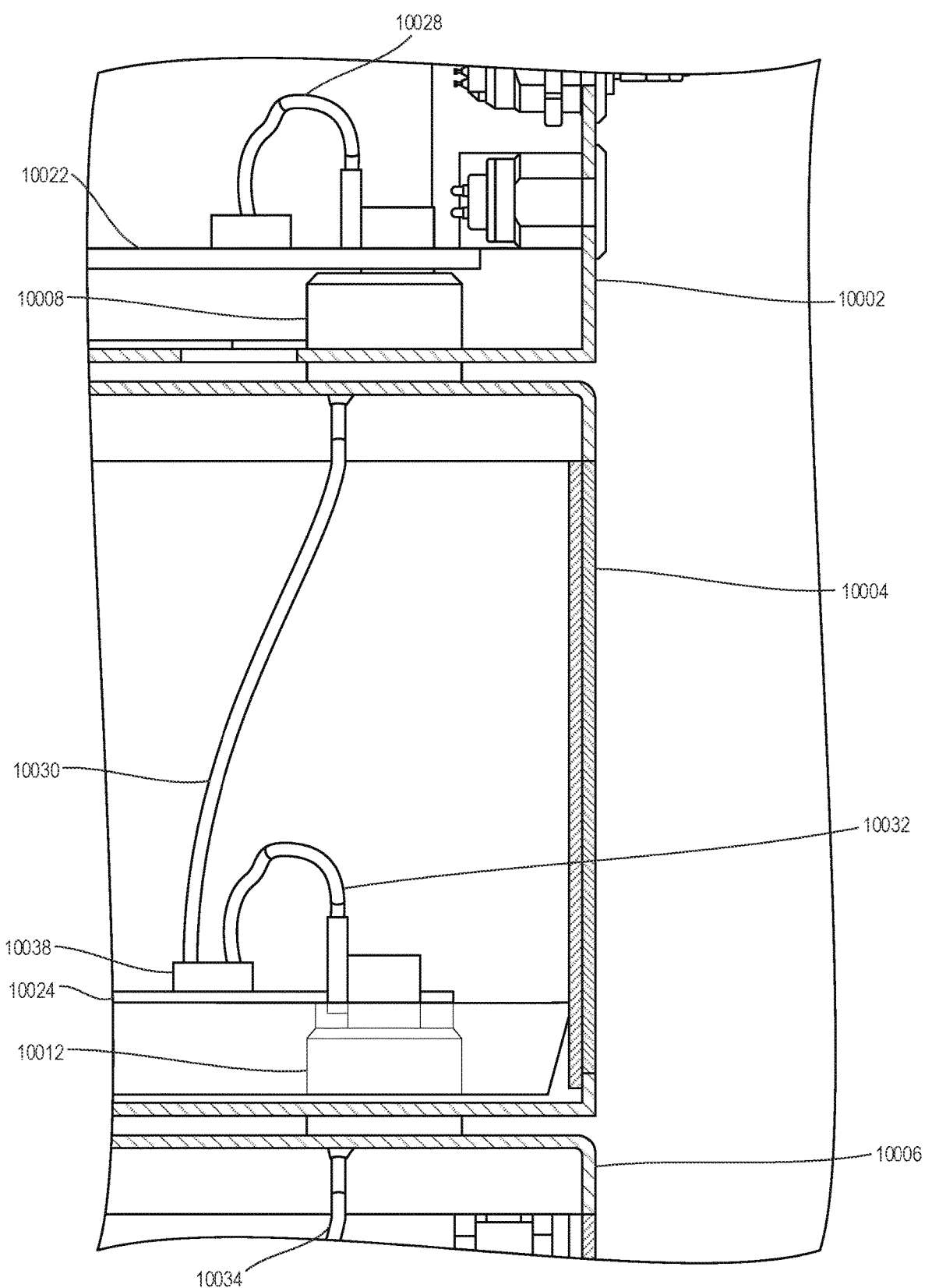
FIG. 52 illustrates various electrical connections in the modular energy system of FIG.

Referring now to FIGS. 51 and 52, a configuration is shown in which three surgical modules, a first module 10002, a second module 10004, and a third module 10006, are assembled together in a stacked configuration by an end user utilizing an internal wiring arrangement to facilitate the transmission of communication signals and power between modules in a modular energy system 10000. Each module 10002, 10004, and 10006, can be the same type of surgical module or different types of surgical modules. For example, each module 10002, 10004, and 10006, can be a header module, an energy module, a generator module, an imaging module, a smoke evacuation module, a suction/irrigation module, a communication module, a processor module, a storage array, a surgical device coupled to a display, a non-contact sensor module, or other modular device. These and other such modules are described above under the headings SURGICAL HUBS and MODULAR ENERGY SYSTEM.

Each module 10002, 10004, and 10006, can include a bridge connector. For example, the first module 10002 can comprise a lower bridge connector 10008, the second module 10004 can comprise an upper bridge connector 10010 (FIG. 53) and a lower bridge connector 10012, and the third module 10006 can comprise an upper bridge connector (not shown) and a lower bridge connector 10016. Each bridge connector, 10008, 10010, 10012, and 10016, can include an outer housing extending at least partially around electrical connection elements of the respective bridge connector.

Figure 53:
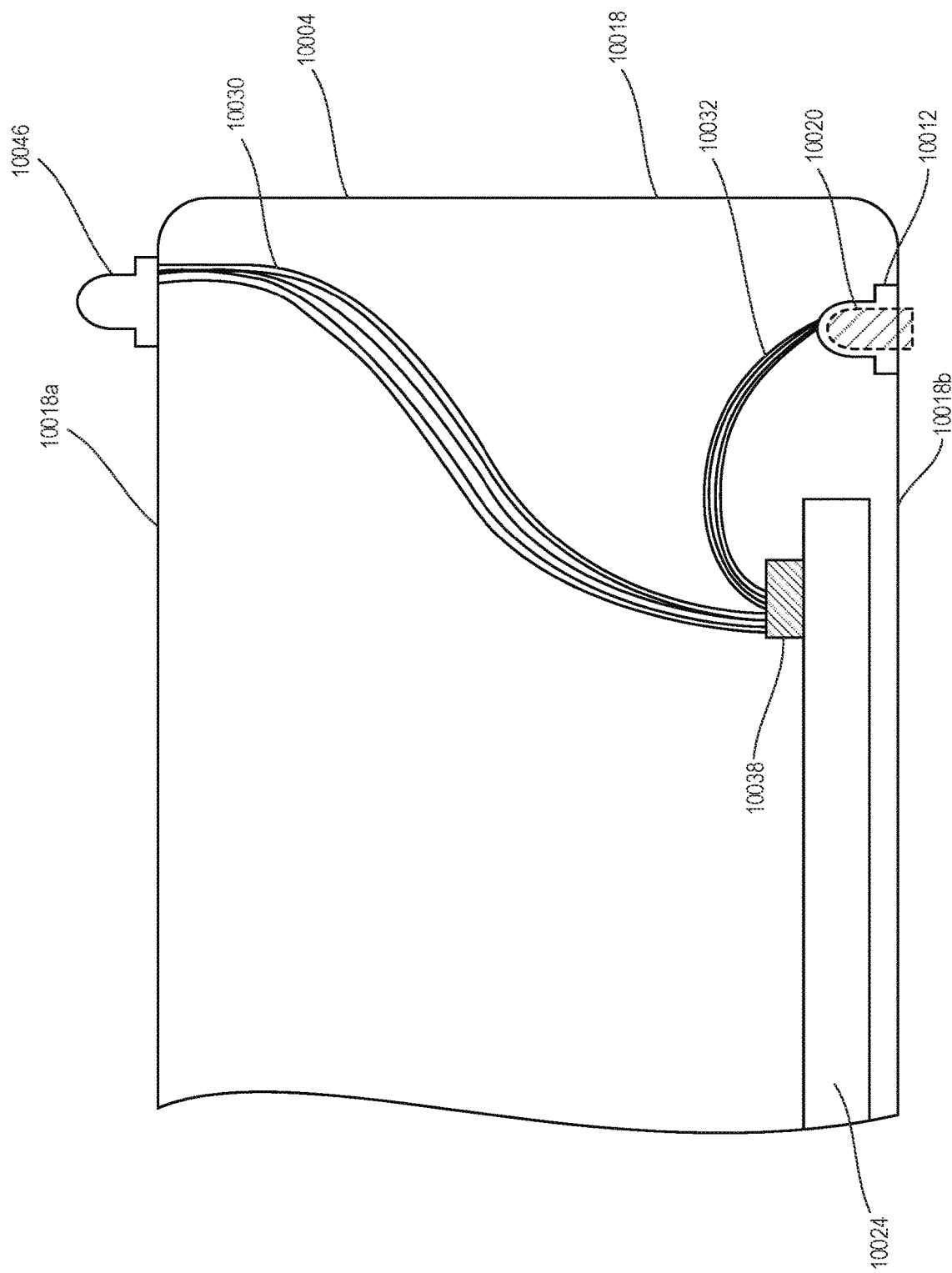
FIG. 53 illustrates a module of the modular energy system of FIG. 51.

Referring to FIG. 53, a detailed view of an embodiment of the second module 10004 is provided. It is understood the first module 10002 and the third module 10006 can be configured as the second module 10004 illustrated in FIG. 53. The upper bridge connector 10010 of the second module 10004 is mounted to a top surface 10018*a* of the enclosure 10018 and extends away from the second module 10004. The lower bridge connector 10012 of the second module 10004 is mounted to the bottom surface 10018*b* of the enclosure 10018 of the second module 10004. The lower bridge connector 10012 includes a recess 10020 that is shaped and configured to receive an upper bridge connector from a separate module. For example, when the second module 10004 is stacked on top of the third module 10006, the upper bridge connector of the third module 10006 is inserted into the recess 10020 of the lower bridge connector 10016 of the second module 10004, thus, aligning the second module 10004 with the third module 10006.

Referring to back to FIGS. 51 and 52, each module, 10002, 10004, and 10006, further includes a PCB. For example, the first module 10002 includes a first PCB 10022, the second module 10004 includes a second PCB 10024, and the third module 10006 includes a third PCB 10026.

Additionally, each module, 10002, 10004, and 10006, includes a flexible wire harness (e.g., flexible cable) electrically connected to the respective PCB, 10022, 10024, and 10026, by any suitable number of connections. For example, the first module 10002 includes a first flexible wire harness 10028 extending from the first PCB 10022 and operably coupled to the lower bridge connector 10008 of the first module 10002 to connect the first PCB 10022 with electrical connection elements of the lower bridge connector 10008. The first flexible wire harness 10028 is positioned within the first module 10002 and, thus, may facilitate quicker assembly of a modular energy system.

The second module 10004 includes a second flexible wire harness 10030 and a third flexible wire harness 10032 extending from the second PCB 10024. The second flexible wire harness 10030 is operably coupled to the upper bridge connector 10010 of the second module 10004 to connect the second PCB 10024 with electrical connection elements of the upper bridge connector 10010. The third flexible wire harness 10032 is operably coupled to the lower bridge connector 10012 of the second module 10004 to connect the second PCB 10024 with electrical connection elements of the lower bridge connector 10012. The second and third flexible wire harnesses 10030 and 10032 are positioned within the second module 10002 and, thus, may facilitate quick assembly of a modular energy system.

The third module 10006 includes a fourth flexible wire harness 10034 and a fifth flexible wire harness 10036 extending from the third PCB 10026. The fourth flexible wire harness 10034 is operably coupled to the upper bridge connector of the third module 10006 to connect the third PCB 10026 with electrical connection elements of the upper bridge connector of the third module 10006. The fifth flexible wire harness 10036 is operably coupled to the lower bridge connector 10016 of the third module 10006 to connect the third PCB 10026 with the electrical connection elements of the lower bridge connector 10016. The fourth and fifth flexible wire harnesses 10034 and 10036 are positioned within the third module 10002 and thus, may facilitate quick assembly of a modular energy system.

When an upper bridge connector of a lower module is positioned in a lower bridge connector of an upper module (e.g., the electrical connection elements of the bridge connectors are electrically coupled), the upper flexible wire harness connected to the upper bridge connector of the lower module is electrically coupled with the lower flexible wire harness connected to the lower bridge connector of the upper module. When coupled, power and communication signals are able to flow from the lower module to the upper module (and/or from the upper module to the lower module) by way of the internal flexible wire harnesses and the PCBs. For example, when the upper bridge connector 10014 of the third module 10006 is positioned in the lower bridge connector 10012 of the second module 10004, the fourth flexible wire harness 10034 is electrically coupled with the third flexible wire harness 10032. Thus, power and communications signals are able to flow from the third module 10006 to the second module 10004 by way of the third and fourth flexible wire harnesses, 10032 and 10034, and the respective PCBs, 10023 and 10026.

Referring back to FIGS. 51-53, in one instance, a board connector 10038 is mounted on the second PCB 10024 and a board connector 10066 is mounted on the third PCB 10026. The second flexible wire harness 10030 is configured to extend from the upper bridge connector 10010 and connect to the board connector 10038, while the third flexible wire harness 10032 is configured to extend from the lower bridge connector 10012 and connect to the board connector 10038. The fourth flexible wire harness 10034 is configured to extend from the upper bridge connector of the third module 10006 and connect to the board connector 10066, while the fifth flexible wire harness 10036 is configured to extend from the lower bridge connector 10016 and connect to the board connector 10066.

Similar to the scenario described above, when an upper module is connected with a lower module by way of respective bridge connectors, the upper and lower modules are able to communicate and transmit power therebetween by way of the PCBs, the board connectors, and the flexible wire harnesses. For example, referring to FIG. 52, power and communications signals are able to flow from the third module 10006 to the second module 10004 by way of the third and fourth flexible wire harnesses, 10032 and 10034, the board connectors, 10038 and 10066, and the respective PCBs, 10024 and 10026.

Figure 54:
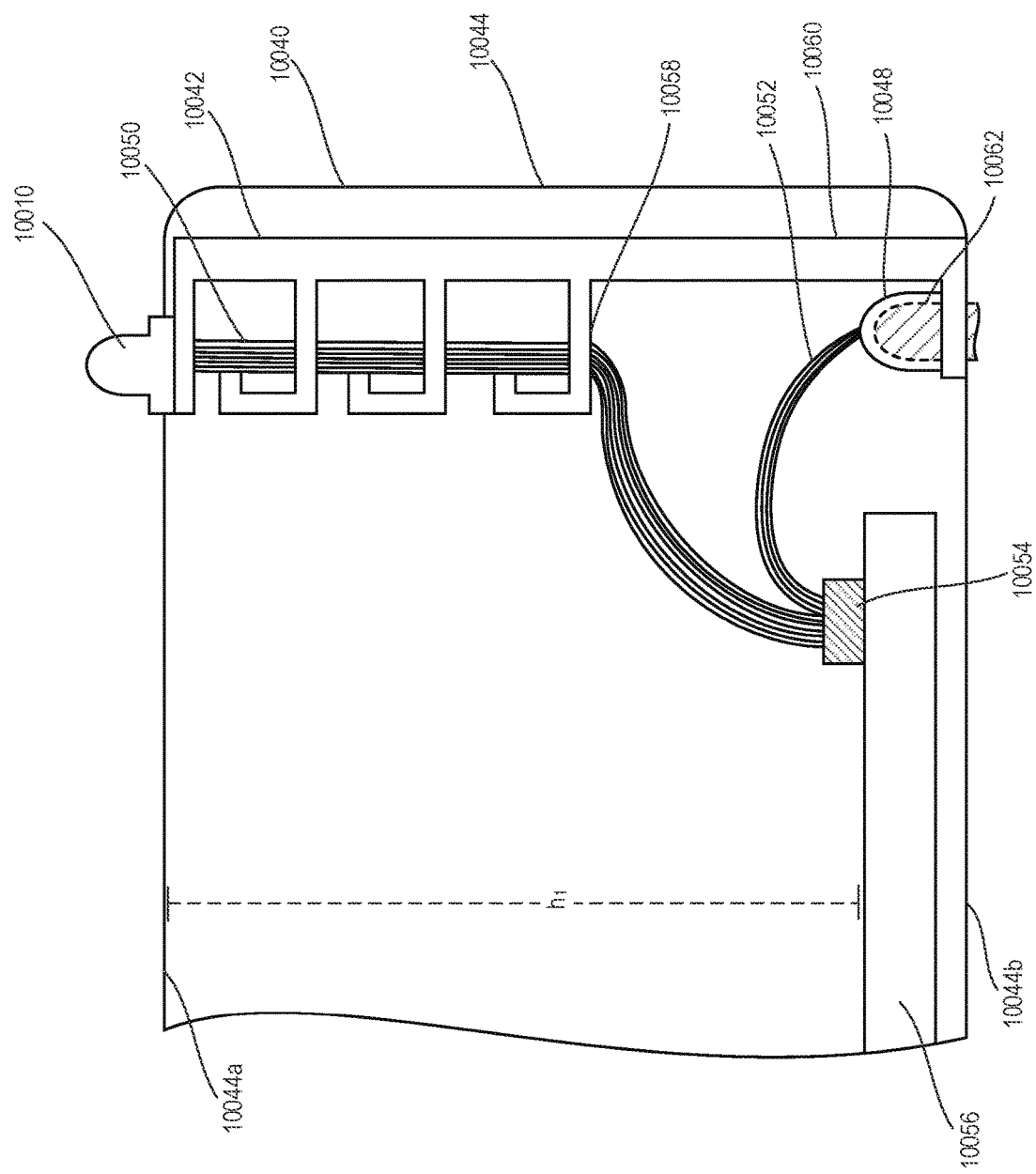
FIG. 54 illustrates a module of a modular energy system, which includes a rigid wire harness, in accordance with at least one aspect of the present disclosure.

Referring now to FIG. 54, a separate embodiment of a module 10040 is shown. The module 10040 illustrated in FIG. 54 is similar in many respects to the second module 10004 shown and described in FIGS. 51-53. However, instead of a flexible wire harness, a rigid wire harness 10042 is utilized. The rigid wire harness 10042 can be sized and configured to stand between a top surface 10044a of an enclosure 10044 of the module 10040 and a bottom surface 10044b of the enclosure 10044 of the module 10040. The rigid wire harness 10042 can extend the full, or at least substantially the full, height, $h_1$, of the module 10040. Further, the upper and lower bridge connectors, 10046 and 10048, are operably coupled (e.g., directly mated) to the rigid wire harness 10042 rather than to the enclosure 10044 of the module 10040. In at least one example, the upper and lower bridge connectors, 10046 and 10048, are integrated with the rigid wire harness 10042.

In the example of FIG. 54, upper wires 10050 extend from a board connector 10054 on the PCB 10056, along the rigid wire harness 10042, and connect to the upper bridge connector 10046. In addition, lower wires 10052 extend from the board connector 10054 and connect to the lower bridge connector 10048. The lower bridge connector 10048 includes a recess 10062 that is shaped and configured to receive an upper bridge connector from a separate module.

A series of holding members 10058 can extend from the rigid wire harness 10042, which are configured to wrap, or at least partially wrap, around the upper wires 10050 to support the upper wires 10050 within a predetermined distance from the rigid wire harness 10042. In the example of FIG. 54, the holding members 10058 extend from a backbone column 10060 that supports the upper and lower bridge connectors, 10046 and 10048.

The ability to mate the rigid wire harness 10042 with the upper bridge connector 10046 and lower bridge connector 10048 provides a distinct advantage when assembling the module 10040. As the rigid wire harness 10042 is one piece and extends the full, or at least substantially the full, height, h₁, of the module 10040, the rigid wire harness 10042 can be inserted into the module 10040 during assembly of the module 10040 and stand free. Once assembled into the module 10040, the upper and lower bridge conneeters, 10046, 10048, can be mated directly with the rigid wire harness 10042, thereby eliminating the need to mount the upper and lower bridge connectors, 10046, 10048, to the top and bottom surfaces, 10044a, 10044b, of the enclosure 10044, respectively, thus, reducing assembly time. The rigid wire harness 10042 can limit force applied to an enclosure 10044 of the module 10040 during assembly of a modular energy system and can reliably establish and/or maintain connections between bridge connectors.

Figure 70:
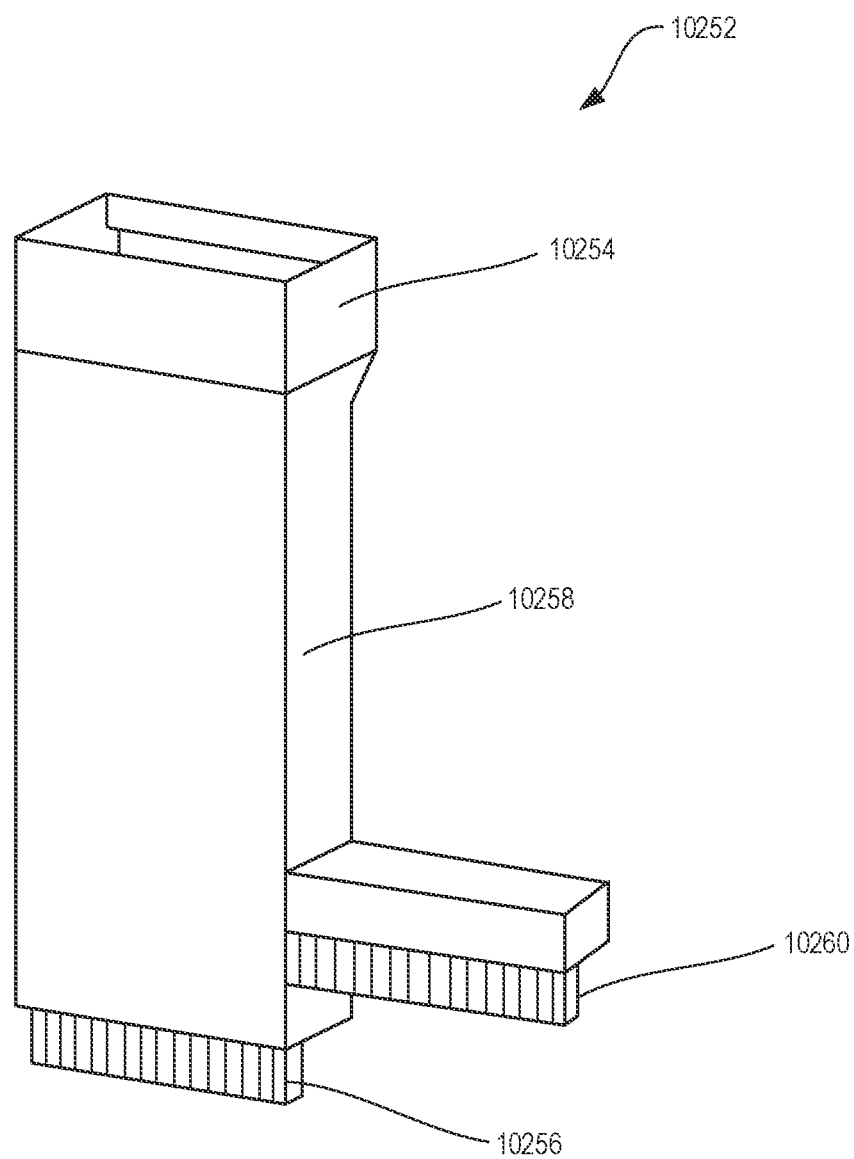
FIG. 70 illustrates a rigid connector, in accordance with at least one aspect of the present disclosure.

Referring to FIG. 70, in a separate embodiment, the flexible wire hardness or rigid wire harness can be replaced by a rigid connector 10252 as shown. The rigid connector 10252 can comprise an integrated upper bridge connector 10254, an integrated lower bridge connector 10256, a PCB extending between the bridge connectors, 10254 and 10256, and a PCB connector 10260. The PCB of the rigid connector 10252 can establish electrical and/or signal communication between the upper bridge connector 10254, the lower bridge connector 10256, and/or the PCB connector 10260. The PCB connector 10260 can be connected to a PCB of a module to establish electrical and/or signal communication between the rigid connector 10252 and the PCB of the module. Further, the rigid connector 10252 can comprise an outer housing 10258 that is over-molded around the PCB of the rigid connector 10252 and can be configured to mate to the enclosure of a module.

The rigid connector 10252 can be sized and configured to stand between a top surface of an enclosure of a module and a bottom surface of the enclosure of the module. The PCB connector 10252 can extend the full, or at least substantially the full, height of the module.

Figure 71:
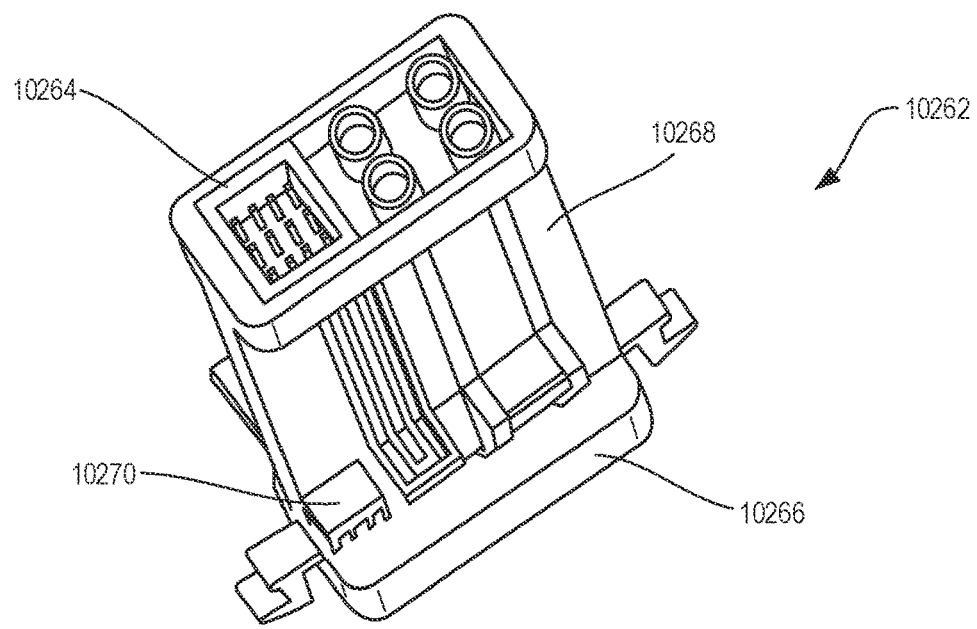
FIG. 71 illustrates a rigid connector, in accordance with at least one aspect of the present disclosure.
Figure 72:
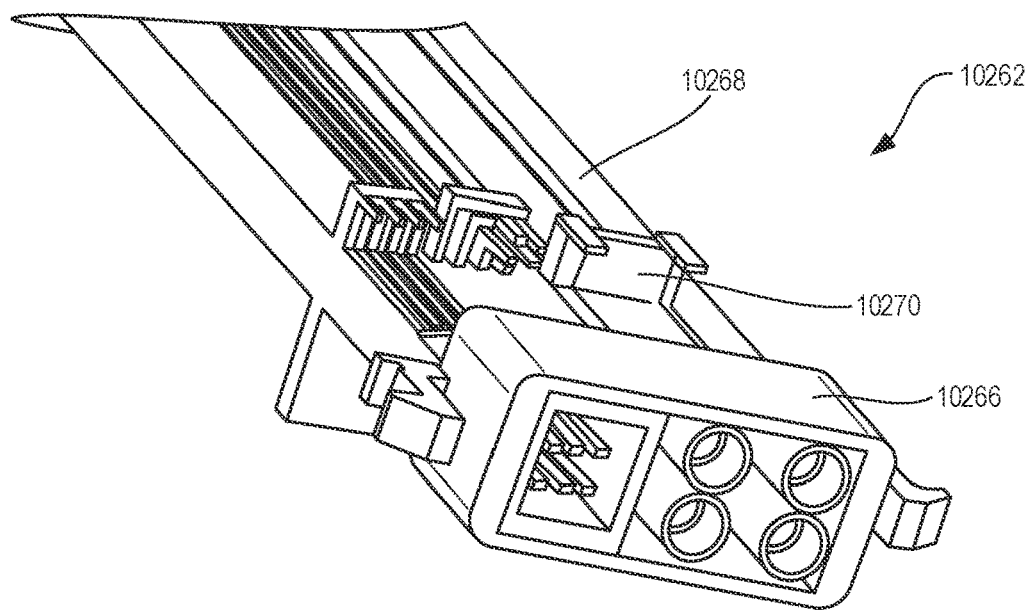
FIG. 72 illustrates a detailed view of the rigid connector of FIG. 71.

Referring to FIGS. 71-72, a separate embodiment of a rigid connector 10262 is provided. The rigid connector 10262 can comprise an integrated upper bridge connector 10264, an integrated lower bridge connector 10256, a PCB 10268 extending between the bridge connectors, 10264 and 10266, and a PCB connector 10270. The PCB 10268 can establish electrical and/or signal communication between the upper bridge connector 10264, the lower bridge connector 10266, and/or the PCB connector 10270. The PCB connector 10270 can be connected to a PCB of a module to establish electrical and/or signal communication between the rigid connector 10262 and the PCB of the module.

The rigid connector 10262 can be sized and configured to stand between a top surface of an enclosure of a module and a bottom surface of the enclosure of the module. The rigid connector 10262 can extend the full, or at least substantially the full, height of the module. The rigid connector 10252 in FIG. 70 and/or the rigid connector 10262 in FIGS. 71-72 can reduce assembly time.

In various aspects, as noted above, the modules of a modular energy system are connected via bridge connectors. Due to the weight of the modules, a user may find it difficult to align bridge connectors during stacking of the modules or assembly of the modular energy system. In certain instances, the user may damage the electrical connection elements of the bridge connectors during stacking. The bridge connectors, 10070 and 10074, illustrated in FIGS. 55-57 allow for modules to be stacked and connected together while being insensitive to the angle that male and female portions of the connectors initially mate. The bridge connector 10070 can be operably coupled to the modules as described herein. For example, the bridge connector 10070 can be the upper bridge connector on any one or more of the modules 10002, 10004, 10006, and 10040 in FIGS. 51-53, and the bridge connector 10074 can be the lower bridge connector on any one or more of the modules 10002, 10004, 10006, and 10040 in FIGS. 51-53.

Figure 55:
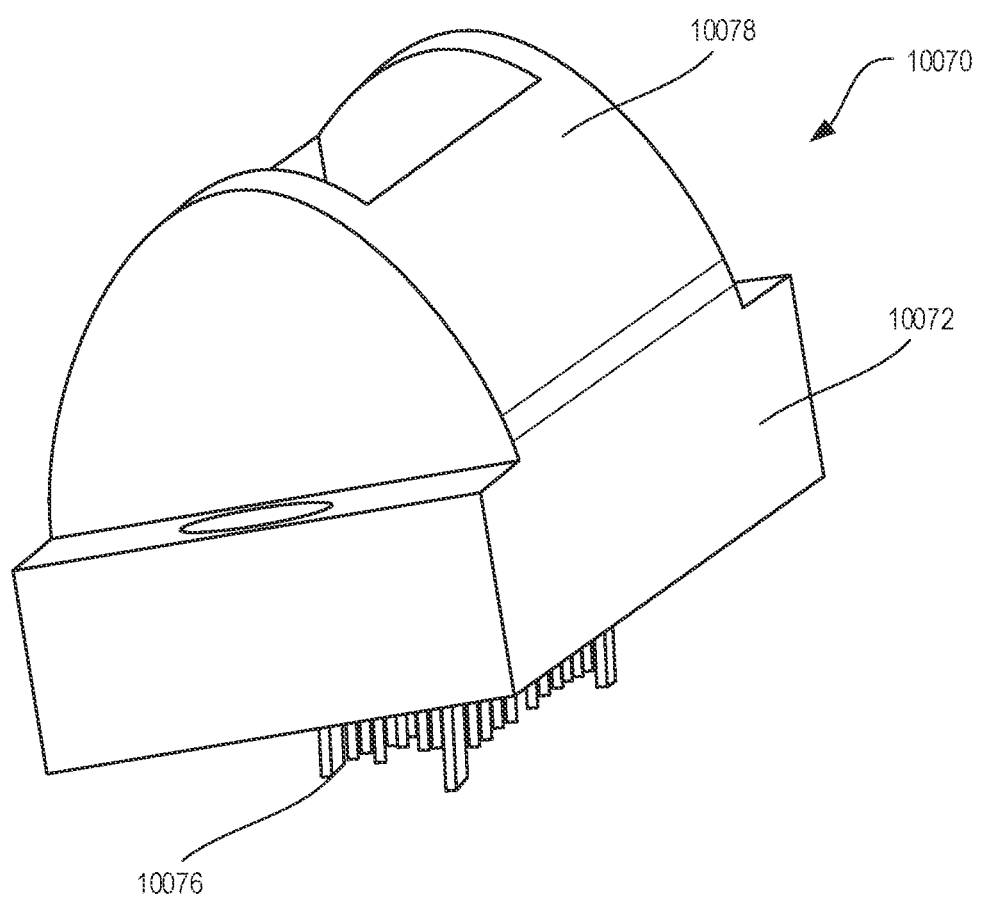
FIG. 55 is a perspective view of a male bridge connector of a modular energy system, in accordance with at least one aspect of the present disclosure.
Figure 56:
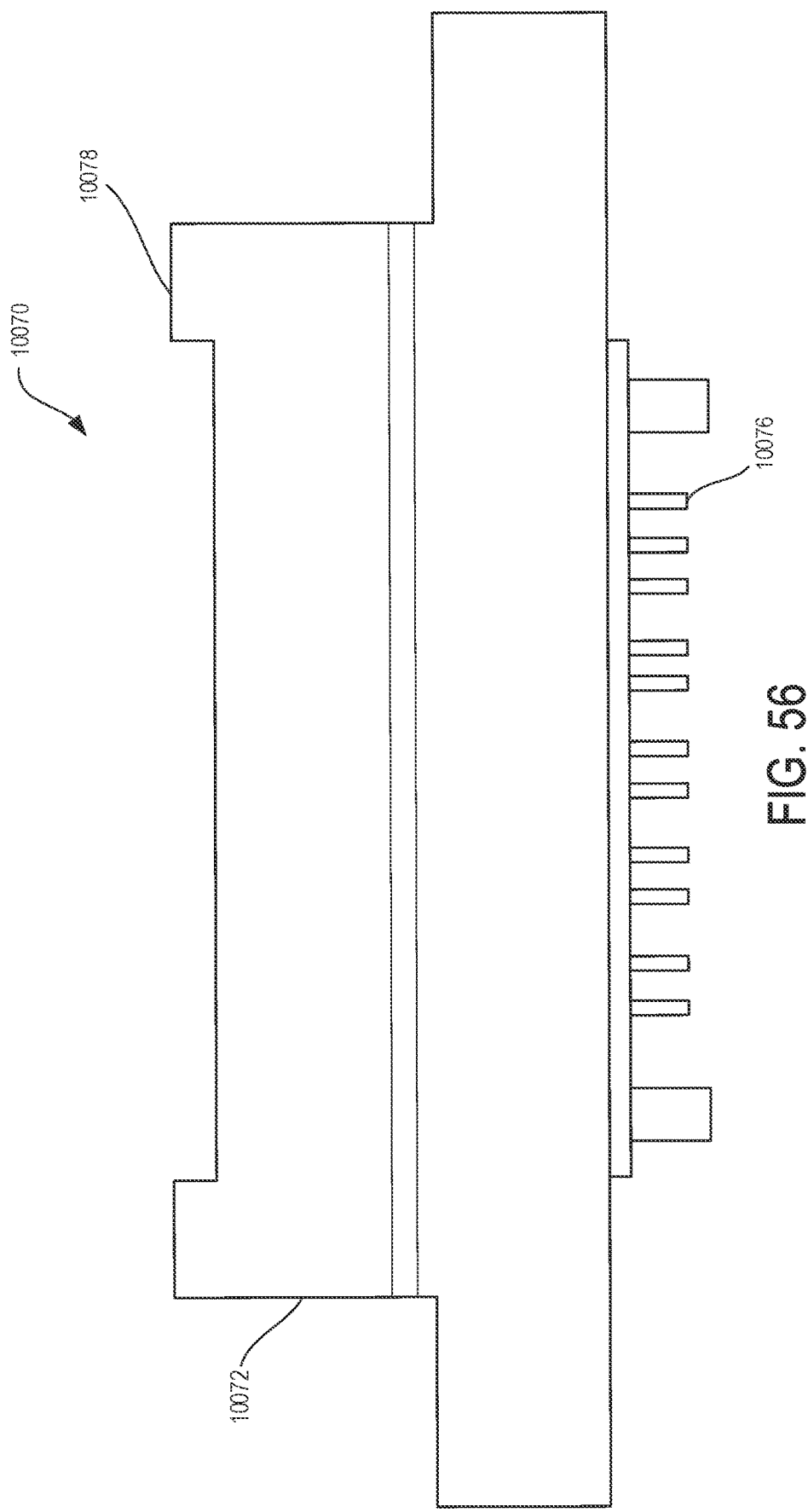
FIG. 56 is a cross-sectional view of the male bridge connector of FIG. 55.

As illustrated in FIGS. 55-56, the bridge connector 10070 includes an outer housing 10072 that extends at least partially around the electrical connection elements 10076 (e.g., pins). For example, the electrical connection elements 10076 can be recessed within the outer housing 10072. The outer housing 10072 is shaped and configured to engage an outer housing of a separate bridge connector during assembly of a stacked configuration of a modular energy system before the electrical connection elements 10076 engage the electrical connection elements of the separate bridge connector.

Figure 57:
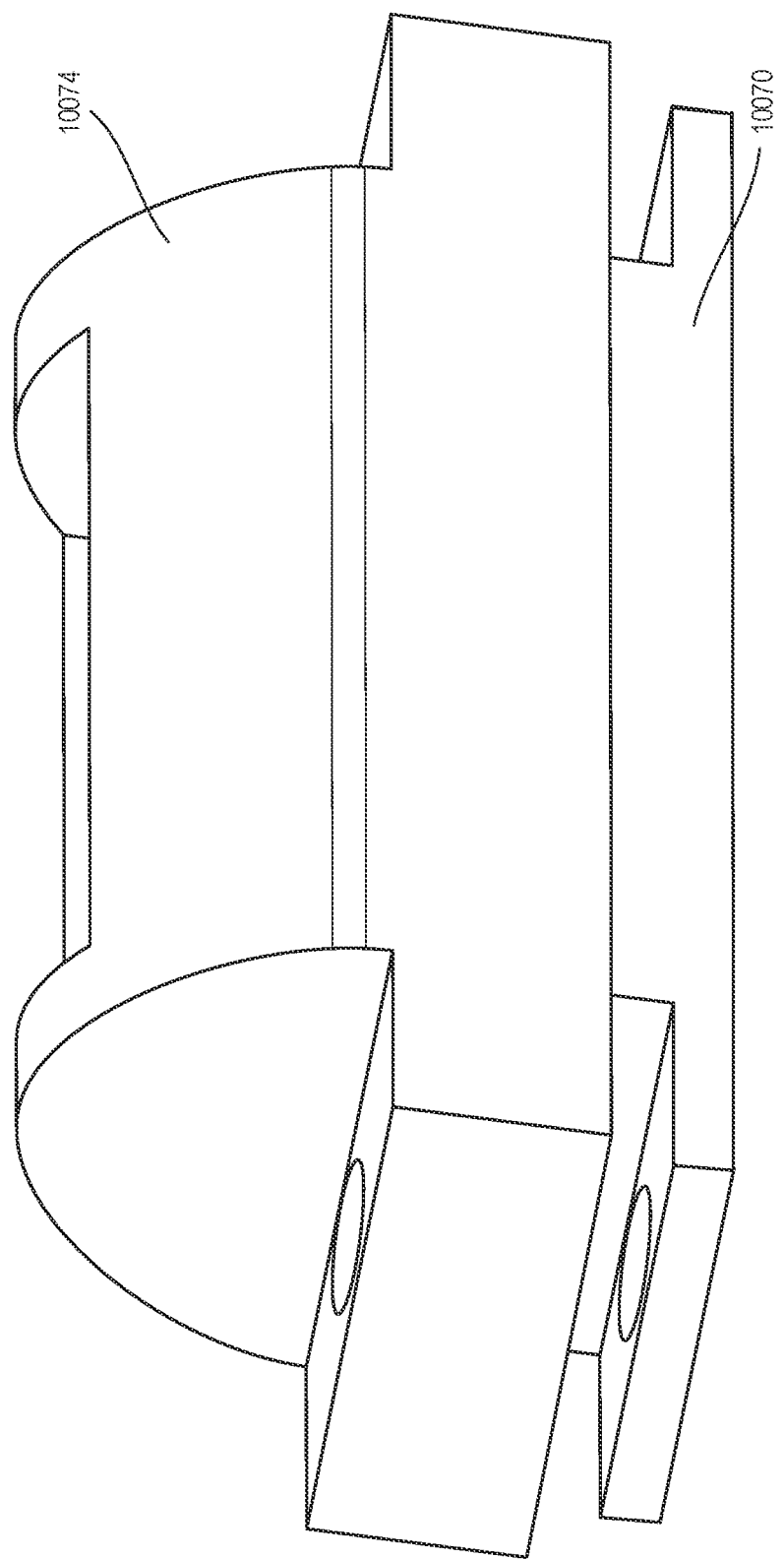
FIG. 57 is a perspective view of male and female bridge connectors of a modular energy system in an assembled configuration, in accordance with at least one aspect of the present disclosure.

As illustrated in FIGS. 55-56, the bridge connector 10070 is a male bridge connector. The bridge connector 10070 and a female bridge connector are shaped and configured to cooperate to properly align the electrical connection elements of the female bridge connector with the electrical connection elements 10076 during assembly of a stacked configuration of a modular energy system. For example, an assembled configuration of the bridge connector 10070 with a female bridge connector 10074 is illustrated in FIG. 57.

The outer housing 10072 is rectangular and rounded along the length of the outer housing 10072. In various aspects, the bridge connector 10070 protrudes from a top surface of a first module and a female bridge connector 10074 is recessed into a bottom surface of a separate module. The outer housing 10072 includes rounded or curved top faces 10078 that allow male and female bridge connectors to align even when modules are at a difficult angle with another. In other words, the outer housing 10072 is shaped and/or sized to guide the electrical connection elements 10076 of the bridge connector 10070 into a properly aligned engagement with the bridge connector 10074, thereby establishing electrical and/or signal communication between the modules and/or alignment between the modules. Further, an outer housing 10078 of the bridge connector 10074 can be shaped and/or sized to guide the electrical connection elements of the bridge connector 10074 into a properly aligned engagement with the bridge connector 10070, thereby establishing electrical and/or signal communication between the modules and/or alignment between the modules. The bridge connectors, 10070 and 10074, illustrated in FIGS. 55-57 can facilitate alignment of the respective electrical connection elements regardless of the angle that male and female portions of the connectors initially mate. Therefore, the modular energy system can be more rapidly assembled into a stacked configuration and the electrical connections therebetween can be more reliable.

As stated herein, the modules of a modular energy system can be connected via bridge connectors and, due to the weight of the modules, a user may find it difficult to keep the modules level during stacking. In certain instances, the user may pay more attention to the mechanical assembly of the modules (e.g., leveling) and less attention to the electrical connections between the modules. Thus, the electrical connection can be improper and/or damaged during stacking of the modules. Separating the mechanical assembly from the electrical assembly of the modules can facilitate faster assembly of the modular energy system and/or increase the reliability of electrical connections between modules in the modular energy system.

Figure 58:
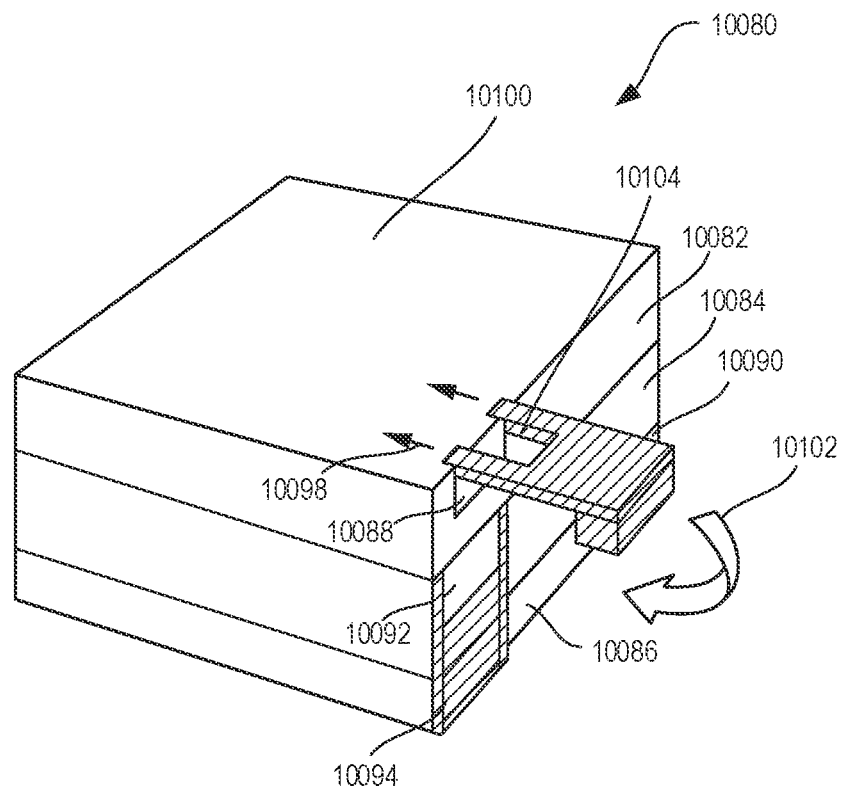
FIG. 58 illustrates a modular energy system, in accordance with at least one aspect of the present disclosure.
Figure 59:
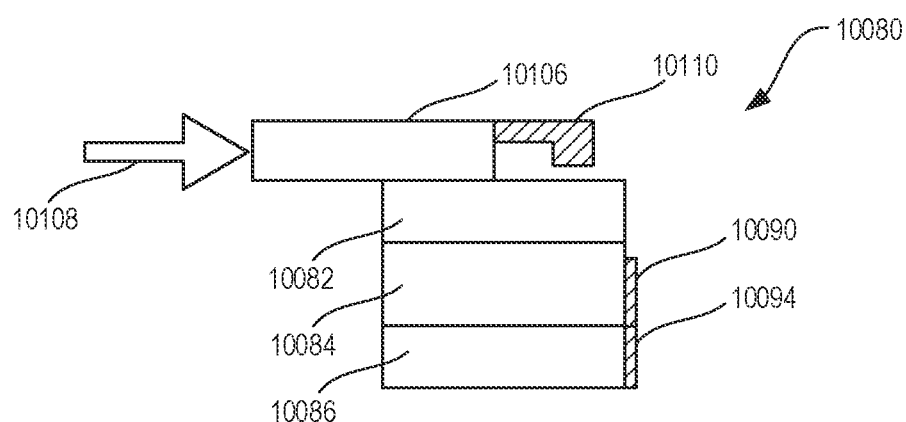
FIG. 59 illustrates various electrical connections in the modular energy system of FIG. 58.

Referring now to FIGS. 58 and 59, a configuration is shown in which three surgical modules, a first module 10082, a second module 10084, and a third module 10086, are assembled together in a stacked configuration by an end user utilizing a park and hide module connection to facilitate the transmission of communication signals and power between modules. Each module, 10082, 10084, and 10086, can be the same type of surgical module or different types of surgical modules. For example, each module 10082, 10084, 10086, can be a header module, an energy module, a generator module, an imaging module, a smoke evacuation module, a suction/irrigation module, a communication module, a processor module, a storage array, a surgical device coupled to a display, a non-contact sensor module, or other modular device. These and other such modules are described above under the headings SURGICAL HUBS and MODULAR ENERGY SYSTEM.

Each module, 10082, 10084, and 10086, can include a park and hide bridge connector. For example, the first module 10082 can comprise an upper bridge connector 10088 and a park and hide bridge connector 10090, the second module 10084 can comprise an upper bridge connector 10092 and a park and hide bridge connector 10094, and the third module 10086 can comprise an upper bridge connector. The bridge connectors, 10088, 10090, 10092, and 10094, are positioned on a surface of the respective module, 10082, 10084, 10086, which may not engage and/or face another module when assembled together in a stacked configuration. In other words, the bridge connectors, 10088, 10090, 10092, and 10094, can be accessible and be manipulated to establish or to de-establish electrical connections when the modules, 10082, 10084, and 10086, are in the stacked configuration.

The connectors, 10090 and 10094, can comprise three positions, a hide position, an extended position, and an engaged position. As illustrated in FIG. 58, the connector 10090 is in an extended position and can be moved into the hide position by translating the connector 10090 in the direction 10098. Thus, the connector 10090 can be hidden within the enclosure 10100 of the first module 10082 such that the connector 10090 can be protected from damage during and/or inhibited from interfering with stacking of the modular energy system 10080.

After stacking of the modular energy system 10080, the connector 10090 can be moved from the hide position, into the extended position as illustrated in FIG. 58, and thereafter into the engaged position by rotating the connector 10090 in the direction 10102. For example, the connector 10094 of the second module 10084 has been rotated into the engaged position and operably coupled to the upper bridge connector of the third module 10086, thereby establishing electrical and/or signal communication between the second module 10084 and the third module 10086. Separating the mechanical assembly from the electrical assembly of the modules utilizing a park and hide bridge connector can enable the user to more reliably establish the electrical connection and inhibit accidental damage of a connector.

Additionally, the connector 10090 can include an opening 10104 configured to enable access to the upper bridge connector 10088 while the connector 10090 is in the engaged position. Thus, referring to FIG. 59, an additional module 10106 can be added to the first three modules, 10082, 10084, and 10086, of the modular energy system 10080 by resting the additional module 10106 first on top of the first module 10082 and sliding the additional module 10106 across the top surface of first module 10092, in the direction indicated by the arrow 10108, until the additional module 10106 and the first module 10082 are assembled into the stacked configuration and/or aligned. Thereafter, a park and hide connector 10110 of the additional module 10106 can be rotated from the extended position as illustrated in FIG. 59 into the engaged position (not shown), thereby establishing electrical and/or signal communication between the first module 10082 and the additional module 10106.

Referring now to FIGS. 60 and 61, a configuration is shown in which two surgical modules, a first module 10112 and a second module 10114, are assembled together in a stacked configuration by an end user utilizing a jumper cable to facilitate the transmission of communication signals and power between modules. Each module, 10112 and 10114, can be the same type of surgical module or different types of surgical modules. For example, each module, 10112 and 10114, can be a header module, an energy module, a generator module, an imaging module, a smoke evacuation module, a suction/irrigation module, a communication module, a processor module, a storage array, a surgical device coupled to a display, a non-contact sensor module, or other modular device. These and other such modules are described above under the headings SURGICAL HUBS and MODULAR ENERGY SYSTEM.

Each module, 10112 and 10114, can include a bridge connector. For example, the first module 10112 can comprise a bridge connector 10116 and the second module 10114 can comprise a bridge connector 10118. The bridge connectors, 10016 and 10018, are positioned on a surface of the respective module 10112 and 10114, which may not engage and/or face another module when assembled together in a stacked configuration. For example, as illustrated in FIG. 60, the bridge connector 10116 is protruding from a back surface 10120a of the enclosure 10120 of the first module 10112 and the bridge connector 10118 is protruding from a back surface 10122a of an enclosure 10122 of the second module 10114. In other words, the bridge connectors, 10116 and 10118, can be accessible and manipulated to establish or to de-establish electrical connections between modules when in the stacked configuration.

The bridge connector 10116 and 10118 can be a male blade connector. A jumper cable 10124 can be operably coupled to the bridge connectors, 10116 and 10118, thereby establishing electrical and/or signal communication between the first module 10112 and the second module 10114. The jumper cable 10124 can comprise two ends, 10126 and 10128, and wires 10130 extending therebetween. In one aspect, each end, 10126 and 10128, is a female blade connector. The ends, 10126 and 10128, of the jumper cable 10124 can be configured to respectively engage the bridge connectors, 10016 and 10018, of the modules, 10112 and 10114, to electrically and/or communicatively couple the modules, 10112 and 10114.

Referring to FIG. 69, the jumper cable 10124 is connected to the bridge connector 10116 of the first module 10112. The bridge connector 10116 can comprise electrical elements 10136, which are electrically connected to wires 10132, and the wires 10132 can be electrically connected to a PCB (not shown) within the first module 10112 by any suitable number of connections.

Securing the modules together in the stacked configuration can prevent modules assembled in the stacked configuration from becoming misaligned while adding an additional module. Thus, various latches and latching mechanisms are provided to secure modules to one another.

For example, the first module 10112 can be stacked on top of the second module 10114 as illustrated in FIGS. 60 and 61. To secure the modules, 10112 and 10114, together, a flip-down latch 10142 of the first module 10112 can be rotated along direction 10144 from a first position as illustrated in FIG. 60 to a second position as illustrated in FIG. 61. The flip-down latch 10142 can engage a joining portion 10146 of the second module 10114, thereby establishing a mechanical connection between the modules, 10112 and 10114. The joining portion 10146 can be, for example, a recessed portion on the enclosure 10122a of the second module 10114. The joining portion 10146 can have features configured to engage and mate with the flip-down latch 10142. In various aspects, the modules, 10112 and 10114, can comprise two or more flip down latches.

Figure 62:
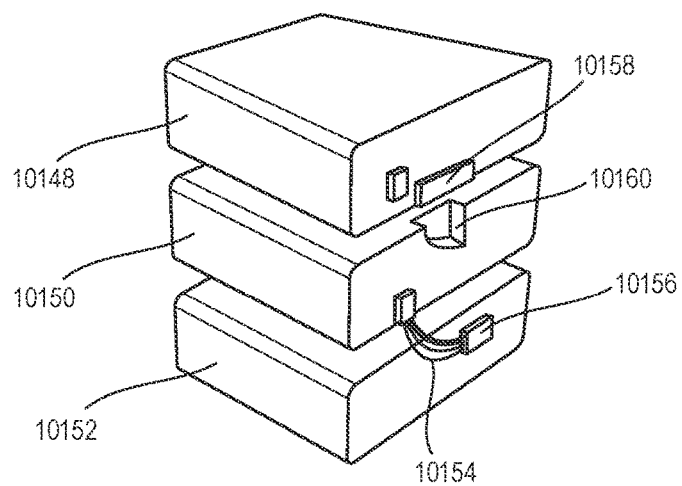
FIG. 62 illustrates a modular energy system comprising a latch, in accordance with at least one aspect of the present disclosure.

Referring to FIG. 62, a configuration is shown in which three modules, a first module 10148, a second module 10150, and a third module 10152, are assembled together in a stacked configuration by an end user. Thereafter, a cord assembly 10154 of the second module 10150 can be configured to engage a joining portion 10156 of the third module 10152, thereby mechanically connecting the modules, 10150 and 10152, together as illustrated in FIG. 62. In some examples, the cord assembly 10154 can also establish electrical and/or signal communication between the second module 10150 and the third module 10152. Similarly, a lever assembly 10158 of the first module 10148 can be configured to engage a joining portion 10160 of the second module 10150, thereby mechanically connecting the modules, 10148 and 10150, together. The lever assembly 10158 can also establish electrical and/or signal communication between the first module 10148 and the second module 10150. Accordingly, a modular energy system can comprise various latches and latching mechanisms that are the same or that are different as illustrated in FIG. 62.

Figure 63A:
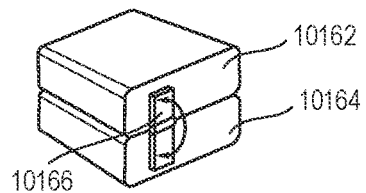
FIG. 63A illustrates a modular energy system comprising a latch assembly, in accordance with at least one aspect of the present disclosure.
Figure 63B:
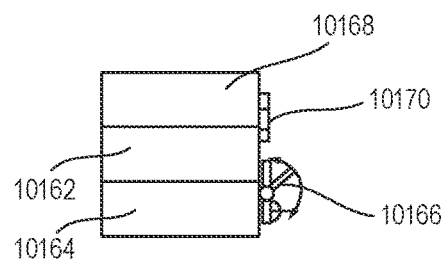
FIG. 63B illustrates a side view of the modular energy system of FIG. 63A.

Referring to FIGS. 63A and 63B, a configuration is shown in which the modules of a modular energy system can comprise a flip-down latch. For example, two modules, a first module 10162 and a second module 10164, are assembled together in a stacked configuration by an end user. The first module 10162 is connected to the second module 10164 by a flip-down latch 10166. Thereafter, an additional module 10168 can be stacked on top of the first module 10162 and secured to the first module 10162 by a flip-down latch 10170.

Figure 64A:
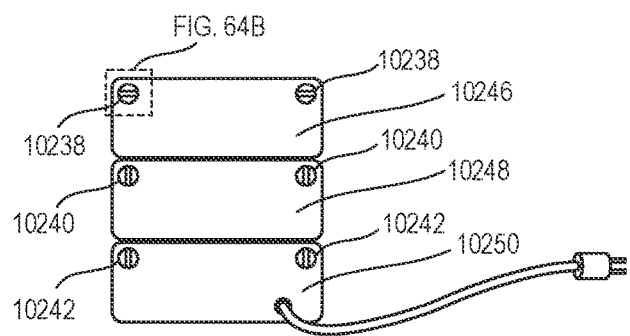
FIG. 64A illustrates a modular energy system comprising a latch assembly, in accordance with at least one aspect of the present disclosure.
Figure 64B:
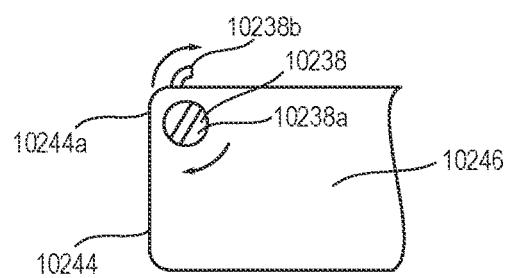
FIG. 64B illustrates a detail view of the modular energy system of FIG. 64A.

Referring to FIGS. 64A, 64B, 65, and 66, a configuration is shown in which the modules of a modular energy system can comprise a rotatable latch assembly configured to secure the modules together in the stacked configuration. In one aspect, as illustrated in FIGS. 64A and 64B, three modules, a first module 10246, a second module 10248, and a third module 10250, are assembled together in a stacked configuration by an end user. The first module 10246 comprises rotatable latch assemblies 10238, the second module 10248 comprises rotatable latch assemblies 10240, and the third module 10250 comprises rotatable latch assemblies 10242. The first module 10246 is connected to the second module 10248 by the rotatable latch assemblies 10240. The second module 10248 is connected to the third module 10250 by the rotatable latch assemblies 10242.

Each rotatable latch assembly, 10238, 10240, and 10242, comprises a handle and a hook assembly. For example, referring to FIG. 64B, rotatable latch assembly 10238 comprises handle 10238a and hook assembly 10240b. The handle 10238a can be rotated from a disengaged position where the hook assembly 10238b is positioned within the enclosure 10244 of the first module 10246 to an engaged positioned where the hook assembly 10238b protrudes from a top surface 10244a of the enclosure 10244 and is configured to engage a joining portion of an enclosure of a separate module. Thus, an upper module and a lower module can be secured together in a stacked configured when the rotatable latch assemblies of the lower module are configured in the engaged position. The upper and lower modules can be disassembled from a stacked configuration when the rotatable latch assemblies of the lower module are configured in the disengaged position.

In one aspect, as illustrated in FIG. 65, three modules, a first module 10172, a second module 10174, and a third module 10176, are assembled together in a stacked configuration by an end user. The first module comprises rotatable latch assembly 10178, the second module comprises rotatable latch assembly 10180, and the third module comprises rotatable latch assemblies 10182. The first module 10172 is connected to the second module 10174 by the rotatable latch assembly 10180. The second module 10174 is connected to the third module 10176 by the rotatable latch assembly 10182.

Each rotatable latch assembly, 10178, 10180, and 10182, comprises a handle and a hook assembly. For example, the rotatable latch assembly 10178 comprises a handle 10178a and a hook assembly 10178b. The handle 10178a can be rotated from a disengaged position where the hook assembly 10178b is positioned within the enclosure 10184 of the first module 10172 to an engaged positioned where the hook assembly 10178b protrudes from a top surface 10184a of the enclosure 10184 and is configured to engage a joining portion of an enclosure of a separate module. Thus, an upper module and a lower module can be secured together in a stacked configured when the rotatable latch assembly of the lower module is configured in the engaged position. The upper and lower modules can be disassembled from a stacked configuration when the rotatable latch assembly of the lower module is configured in the disengaged position.

Referring to FIG. 66, a configuration is shown in which three modules, a first module 10186, a second module 10188, and a third module 10190, are assembled together in a stacked configuration by an end user. The first module 10186 comprises a first latch assembly 10192 and a second latch assembly 10194. Upon moving the handle 10192a of the first latch assembly 10192 in the direction 10196, a hook assembly 10198 of the first latch assembly moves in the direction 10200 and engages the enclosure 10202 of the second module 10188, thereby mechanically securing the first module 10186 to the second module 10188. The second latch assembly 10194 operates in a similar manner to the first latch assembly 10192.

Similarly, the second module 10188 comprises a first latch assembly 10204 and a second latch assembly 10206. The latch assemblies, 10204 and 10206, can engage the enclosure 10208 of the third module 10190, thereby mechanically securing the second module 10188 to the third module 10190.

Referring to FIG. 67, a configuration is shown in which two modules, a first module 10210 and a second module 10212, are assembled together in a stacked configuration by an end user. The first module 10210 comprises a cord assembly 10214, which can be configured to engage with a corresponding connector or portion of another module (such as the second module 10212). Accordingly, the cord assembly 10214 can be transition between a first position 10216, in which the core assembly 10214 can be secured to the first module 10210 (and thus disengaged from the second module 10212), and a second position 10218. Upon configuring the cord assembly 10214 in the second position 10218, the first module 10210 can be mechanically secured to the second module 10212 by the cord assembly 10214. In one aspect, the cord assembly 10214 can also establish electrical and/or signal communication between the first module 10210 and the second module 10212. That is, the cord assembly 10214 can be attached to a PCB of the first module 10210 and connected to a bridge connector of the second module 10212. However, the cord assembly 10212 can be sized and configured to maintain the position of the first module 10210 with respect to the second module 10212.

Referring to FIG. 68, two modules, a first module 10220 and a second module 10222, are assembled together in a stacked configuration by an end user. The first module 10220 comprises a recess 10224 configured to receive a plug 10226 and the second module 10222 comprises a recess 10228 that is also configured to receive the plug 10226. The plug 10226 can be slidably disposed within or slidably connected to either the recess 10224 of the first module 10220 or the recess 10228 of the second module 10222. The plug 10226 can be moveable between a first position and a second position. In one aspect, in the first position, the plug 10226 can be solely within the recess 10228 of the second module 10222. The plug 10226 can be translated in the direction 10230 and into the recess 10226 in order to mechanically secure the first module 10220 and the second module 10222. In an alternative aspect, in the first position, the plug 10226 can be positioned within the recess 10224 of the first module 10220 and then translated to engage the corresponding recess 10228 of the second module 10222 to mechanically engage the first and second modules 10220, 10222 together.

In various aspects, the plug 10226 is electrically connected to a wire harness 10140 and comprises first electrical connection elements on an end 10236 of the plug 10226. The recess 10226 can comprise a bridge connector portion 10234 comprising second electrical connection elements. The plug 10226 can be translated in direction 10230 and can contact the second electrical connection elements, thereby establishing electrical and/or signal communication between the first module 10220 and the second module 10222.

In various aspects, the bridge connector can be electrically coupled to a flexible power supply (e.g., an H-bridge type power supply) that is configured to provide current and voltage feedback and control. The flexible power supply can be configured to a variety of different applications, including fixed pulsing power delivery, pulse-width modulation (PWM) pulsing power delivery, closed-loop control (i.e., based upon feedback provided to the power supply), delivery of AC and/or DC power, power mitigation (e.g., as is described in U.S. patent application titled POWER AND COMMUNICATION MITIGATION ARRANGEMENT FOR MODULAR SURGICAL ENERGY SYSTEM, filed concurrently herewith, which is hereby incorporated by reference herein), and/or separate patient isolation of hardware. These and other functions can be enabled for any module coupled to the flexible power supply through the connections between the opposing bridge connectors as the modules are engaged together.

EXAMPLES

Various aspects of the subject matter described herein are set out in the following numbered examples:

Example 1

A method for controlling an output of an energy module of a modular energy system, the energy module comprising a plurality of amplifiers and a plurality of ports coupled to the plurality of amplifiers, each of the plurality of amplifiers configured to generate a drive signal at a frequency range, each of the plurality of ports configured to drive an energy modality for a surgical instrument connected thereto according to each drive signal, the method comprising: determining to which port of the plurality of ports the surgical instrument is connected; selectively coupling an amplifier of the plurality of amplifiers to the port of the plurality of ports to which the surgical instrument is connected; and controlling the amplifier to deliver the drive signal for driving the energy modality to the surgical instrument through the port.

Example 2

The method of Example 1, wherein the energy modality comprises monopolar electrosurgical energy.

Example 3

The method of Example 2, wherein: the port comprises a first port; and the plurality of ports further comprises a second port coupled to the amplifier, the second port configured to be connected to a monopolar return pad configured to serve as an electrical ground for the monopolar electrosurgical energy.

Example 4

The method of Example 3, wherein the energy module further comprises an isolation transformer coupling the first port and the second port to the amplifier.

Example 5

The method of any one of Examples 1-4, wherein: the surgical instrument comprises a first surgical instrument; the port comprises a first port; and the plurality of ports further comprises a second port coupled to the amplifier, the second port configured to be connected to a second surgical instrument.

Example 6

The method of Example 5, further comprising: determining whether a fault condition is occurring where the drive signal is being delivered to the second port; and in the fault condition, deactivating the amplifier.

Example 7

A method for controlling an output of an energy module of a modular energy system, the energy module comprising a plurality of amplifiers, a plurality of ports coupled to the plurality of amplifiers, and a relay assembly, each of the plurality of amplifiers configured to generate a drive signal at a frequency range, each of the plurality of ports configured to drive an energy modality for a surgical instrument connected thereto according to each drive signal, the method comprising: controlling a first amplifier of the plurality of amplifiers to deliver a first drive signal to the surgical instrument connected to a port; controlling the relay assembly to couple a second amplifier of the plurality of amplifiers to the port; and controlling the second amplifier to deliver a second drive signal to the surgical instrument connected to the port.

Example 8

The method of Example 7, wherein the second drive signal is configured to drive monopolar electrosurgical energy deliverable by the surgical instrument.

Example 9

The method of Example 8, wherein: the port comprises a first port; and the plurality of ports further comprises a second port coupled to the amplifier, the second port configured to be connected to a monopolar return pad configured to serve as an electrical ground for the monopolar electrosurgical energy.

Example 10

The method of Example 9, wherein the energy module further comprises an isolation transformer coupling the first port and the second port to the amplifier.

Example 11

The method of any one of Examples 7-10, wherein: the surgical instrument comprises a first surgical instrument; the port comprises a first port; and the plurality of ports further comprises a second port selectively couplable to the amplifier via the relay assembly, the second port configured to be connected to a second surgical instrument.

Example 12

The method of Example 11, further comprising: determining whether a fault condition is occurring where the drive signal is being delivered to the second port; and in the fault condition, deactivating the amplifier.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A method for controlling an output of an energy module of a modular energy system, the energy module comprising a plurality of amplifiers and a plurality of ports coupled to the plurality of amplifiers, each of the plurality of amplifiers configured to generate a drive signal at a frequency range, each of the plurality of ports configured to drive an energy modality for a surgical instrument connected thereto according to each drive signal, wherein a first amplifier of the plurality of amplifiers is selectively couplable to a first port of the plurality of ports and selectively couplable to a second port of the plurality of ports, the energy module further comprising a first current sensing transformer associated with the first port and a second current sensing transformer associated with the second port, the method comprising:
   determining the surgical instrument is connected to the first port;
   selectively coupling the first amplifier to the first port based on determining the surgical instrument is connected to the first port;
   controlling the first amplifier to deliver the drive signal for driving the energy modality to the surgical instrument through the first port;
   sensing the drive signal by the first current sensing transformer;
   sensing the drive signal by the second current sensing transformer; and
   detecting that the amplifier is inadvertently delivering the drive signal for driving the energy modality to the second port based on sensing the drive signal by the second current sensing transformer.

2. The method of claim 1, wherein the energy modality comprises monopolar electrosurgical energy.

3. The method of claim 2, wherein:
   the plurality of ports further comprises a third port coupled to the amplifier, the third port configured to be connected to a monopolar return pad configured to serve as an electrical ground for the monopolar electrosurgical energy.

4. The method of claim 3, wherein the energy module further comprises an isolation transformer coupling the first port and the third port to the amplifier.

5. The method of claim 1, wherein:
   the surgical instrument comprises a first surgical instrument; and
   the second port is configured to be connected to a second surgical instrument.

6. The method of claim 5, further comprising:
   determining a fault condition is occurring based on sensing the drive signal by the second current sensing transformer.

7. The method of claim 1, further comprising selectively decoupling the first amplifier from the second port based on detecting that the amplifier is inadvertently delivering the drive signal for driving the energy modality to the second port.

8. The method of claim 1, further comprising deactivating the first amplifier based on detecting that the first amplifier is inadvertently delivering the drive signal for driving the energy modality to the second port.

9. A method for controlling an output of an energy module of a modular energy system, the energy module comprising a plurality of amplifiers, a plurality of ports coupled to the plurality of amplifiers, and a relay assembly, each of the plurality of amplifiers configured to generate a drive signal at a frequency range, each of the plurality of ports configured to drive an energy modality for a surgical instrument connected thereto according to each drive signal, the method comprising:
   controlling a first amplifier of the plurality of amplifiers to deliver a first drive signal to a first surgical instrument connected to a first port of the plurality of ports, the first drive signal configured to drive ultrasonic energy deliverable by the first surgical instrument;

controlling the relay assembly to selectively couple a second amplifier of the plurality of amplifiers to the first port;

controlling the second amplifier to deliver a second drive signal to the first surgical instrument connected to the first port, the second drive signal configured to drive monopolar electrosurgical energy deliverable by the first surgical instrument;

controlling a third amplifier of the plurality of amplifiers to deliver a third drive signal to the first surgical instrument connected to the first port, the third drive signal configured to drive bipolar electrosurgical energy deliverable by the first surgical instrument; and controlling a fourth amplifier of the plurality of amplifiers to deliver a fourth drive signal to a second surgical instrument connected to a second port of the plurality of ports.

10. The method of claim 9, wherein the plurality of ports further comprises a third port coupled to the second amplifier, the third port configured to be connected to a monopolar return pad configured to serve as an electrical ground for the monopolar electrosurgical energy.

11. The method of claim 10, wherein the energy module further comprises an isolation transformer coupling the first port and the third port to the second amplifier.

12. The method of claim 11, wherein: the plurality of ports further comprises a fourth port selectively couplable to the second amplifier via the relay assembly, the fourth port configured to be connected to a second third surgical instrument.

13. The method of claim 12, further comprising:

determining whether a fault condition is occurring where the second drive signal is being delivered to the fourth port; and in the fault condition, deactivating the second amplifier.

14. A method for controlling an output of an energy module of a modular energy system, the energy module comprising a plurality of amplifiers and a plurality of ports coupled to the plurality of amplifiers, each of the plurality of amplifiers configured to generate a drive signal at a frequency range, each of the plurality of ports configured to drive an energy modality for a surgical instrument connected thereto according to each drive signal, wherein a first amplifier of the plurality of amplifiers is selectively couplable to a first port of the plurality of ports and selectively couplable to a second port of the plurality of ports, the energy module further comprising a current sensing transformer associated with the first port, the method comprising:

determining the surgical instrument is connected to the first port;

selectively coupling the first amplifier to the first port based on determining the surgical instrument is connected to the first port;

controlling the first amplifier to deliver the drive signal for driving the energy modality to the surgical instrument through the first port;

sensing, by the current sensing transformer, the drive signal is not being delivered through the first port; and determining that a fault condition has occurred based on sensing the drive signal is not being delivered through the first port.

15. The method of claim 14, further comprising deactivating the first amplifier based on determining that a fault condition has occurred.

* * * * *